US009115193B2

(12) United States Patent
Norris

(10) Patent No.: US 9,115,193 B2
(45) Date of Patent: *Aug. 25, 2015

(54) VMP-LIKE SEQUENCES OF PATHOGENIC *BORRELIA* SPECIES AND STRAINS

(71) Applicant: BOARD OF REGENTS, THE UNIVERSITY OF TEXAS SYSTEM, Austin, TX (US)

(72) Inventor: Steven J. Norris, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/257,613

(22) Filed: Apr. 21, 2014

(65) Prior Publication Data

US 2014/0220605 A1 Aug. 7, 2014

Related U.S. Application Data

(60) Continuation of application No. 13/645,950, filed on Oct. 5, 2012, now Pat. No. 8,722,871, which is a division of application No. 13/324,357, filed on Dec. 13, 2011, now Pat. No. 8,283,458, which is a division of application No. 12/962,154, filed on Dec. 7, 2010, now Pat. No. 8,076,470, which is a division of application No. 10/539,956, filed as application No. PCT/US03/41182 on Dec. 22, 2003, now Pat. No. 7,847,084.

(60) Provisional application No. 60/435,077, filed on Dec. 20, 2002.

(51) Int. Cl.

| | |
|---|---|
| *C07H 21/02* | (2006.01) |
| *C07H 21/04* | (2006.01) |
| *A61K 39/02* | (2006.01) |
| *C07K 14/20* | (2006.01) |
| *G01N 33/569* | (2006.01) |
| *A61K 39/00* | (2006.01) |

(52) U.S. Cl.
CPC .......... *C07K 14/20* (2013.01); *G01N 33/56911* (2013.01); *A61K 39/00* (2013.01); *A61K 39/02* (2013.01); *G01N 2333/20* (2013.01)

(58) Field of Classification Search
CPC ........ C07H 21/02; C07H 21/04; A61K 39/00; A61K 39/02; A61K 39/0225
USPC ......... 536/23.1, 23.7; 424/93.1, 184.1, 185.1, 424/190.1, 200.1, 234.1
See application file for complete search history.

(56) References Cited

U.S. PATENT DOCUMENTS

| | | | | |
|---|---|---|---|---|
| 4,554,101 | A | 11/1985 | Hopp | 530/324 |
| 4,578,770 | A | 3/1986 | Mitani | 250/559.2 |
| 4,596,792 | A | 6/1986 | Vyas | 514/21 |
| 4,599,230 | A | 7/1986 | Milich et al. | 424/189.1 |
| 4,599,231 | A | 7/1986 | Milich et al. | 424/189.1 |
| 4,601,903 | A | 7/1986 | Frasch | 424/250.1 |
| 4,608,251 | A | 8/1986 | Mia | 424/185.1 |
| 4,721,617 | A | 1/1988 | Johnson | 424/234.1 |
| 4,801,540 | A | 1/1989 | Hiatt et al. | 435/411 |
| 5,155,022 | A | 10/1992 | Naqui et al. | 435/7.32 |
| 5,178,859 | A | 1/1993 | Simon et al. | 435/139.1 |
| 5,187,065 | A | 2/1993 | Schutzer | 435/7.32 |
| 5,217,872 | A | 6/1993 | Dorward et al. | 435/7.32 |
| 5,217,874 | A | 6/1993 | Guadagno et al. | 435/28 |
| 5,246,844 | A | 9/1993 | Norris et al. | 435/480 |
| 5,279,938 | A | 1/1994 | Rosa | 435/6 |
| 5,283,175 | A | 2/1994 | Weaver et al. | 435/6 |
| 5,304,718 | A | 4/1994 | Ward et al. | 800/266 |
| 5,324,630 | A | 6/1994 | LeFebvre et al. | 435/6 |
| 5,385,826 | A | 1/1995 | Schell et al. | 435/7.32 |
| 5,434,077 | A | 7/1995 | Simon et al. | 435/243 |
| 5,436,000 | A | 7/1995 | Barbour et al. | 424/93.2 |
| 5,571,718 | A | 11/1996 | Dunn et al. | 435/252.3 |
| 6,437,116 | B1 | 8/2002 | Norris et al. | 536/23.7 |
| 6,475,492 | B1 | 11/2002 | Philipp et al. | 424/234.1 |
| 6,610,301 | B1 | 8/2003 | Motz et al. | 424/190.1 |
| 6,660,274 | B2 | 12/2003 | Philipp | 424/234.1 |
| 6,719,983 | B2 | 4/2004 | Norris et al. | 536/23.1 |

(Continued)

FOREIGN PATENT DOCUMENTS

| | | |
|---|---|---|
| WO | WO 91/13630 | 9/1991 |
| WO | WO 97/31123 | 8/1997 |

(Continued)

OTHER PUBLICATIONS

"*Borrelia afzelii* strain ACAI clone 2622 VLsE (vlsE) mRNA, partial cds," XP002679764, database accession No. AY100629, Mar. 19, 2003.

Balmelli and Piffatetti, "Analysis of the genetic polymorphism of *Borrelia burgdorferi* sensu lato by multilocus enzyme electrophoresis," *Int. J. Syst. Bacteriol.*, 46:167-172, 1996.

Barbour and Garon, "Linear plasmids of the bacterium *Borrelia burdorferi* have covalently closed ends," *Science*, 237:409-411, 1987.

Barbour et al., "Structural analysis of the variable major proteins of *Borrelia hermsii*," *J. Exp. Med.*, 158:2127-2140, 1983.

(Continued)

*Primary Examiner* — Rodney P Swartz
(74) *Attorney, Agent, or Firm* — Parker Highlander PLLC

(57) ABSTRACT

The present invention relates to DNA sequences encoding Vmp-like polypeptides of pathogenic *Borrelia*, the use of the DNA sequences in recombinant vectors to express polypeptides, the encoded amino acid sequences, application of the DNA and amino acid sequences to the production of polypeptides as antigens for immunoprophylaxis, immunotherapy, and immunodiagnosis. Also disclosed are the use of the nucleic acid sequences as probes or primers for the detection of organisms causing Lyme disease, relapsing fever, or related disorders, and kits designed to facilitate methods of using the described polypeptides, DNA segments and antibodies.

27 Claims, 16 Drawing Sheets

(56) References Cited

U.S. PATENT DOCUMENTS

| | | | |
|---|---|---|---|
| 6,740,744 B2 | 5/2004 | Norris et al. | 536/23.1 |
| 6,878,816 B2 | 4/2005 | Norris et al. | 536/23.1 |
| 7,135,176 B2 | 11/2006 | Norris et al. | 424/139.1 |
| 7,847,084 B2 * | 12/2010 | Norris | 536/23.7 |
| 8,076,470 B2 * | 12/2011 | Norris | 536/23.7 |
| 8,283,458 B2 | 10/2012 | Norris | 536/23.7 |
| 2007/0117970 A1 | 5/2007 | Norris et al. | 424/185.1 |
| 2013/0102057 A1 | 4/2013 | Norris | 536/23.7 |

FOREIGN PATENT DOCUMENTS

| | | |
|---|---|---|
| WO | WO 99/00413 | 1/1999 |
| WO | WO 00/65064 | 11/2000 |

OTHER PUBLICATIONS

Barbour et al., "Tandem insertion sequence-like elements define the expression site for variable antigen genes of *Borrelia hermsii*," *Infect. Immun.*, 59:390-397, 1991.
Barbour et al., "Variable antigen genes of the relapsing fever agent *Borrelia hermsii* are activated by promoter addition," *Mol. Microbiol.*, 5:489-493, 1991.
Barbour et al., "Variable major proteins of *Borrelia hermsii*," *J. Exp. Med.*, 156:1312-1324, 1982.
Barbour, "Immunochemical analysis of Lyme disease spirochetes," *Yale J. Biomed.*, 57:581-586, 1984.
Barbour, "Plasmid analysis of *Borrelia burgdorferi*, the Lyme disease agent," *J. Clin. Microbiol.*, 26(3):475-478, 1988.
Barstad et al., "Variable major proteins of *Borrelia hermsii*, Epitope mapping and partial sequence analysis of CNBr peptides," *J. Exp. Med.*, 161:1302-1314, 1985.
Barthold et al., "Suspectibility of laboratory rats to isolates of *Borrelia burgorferi* from different geographic area," *Am. J. Trop. Med. Hyg.*, 42:596-600, 1990.
Barthold, "Antigenic stability of *Borrelia burgdorferi* during chronic infections of immunocompetent mice," *Infect. Immun.*, 61:4955-4961, 1993.
Benach et al., "A murine IgM monoclonal antibody binds an antigenic determinant in outer surface protein A, an immunodominant basic protein of the lyme disease spirochete," *The Journal of Immunology*, 140:265-272, 1988.
Brandt et al. "Immunogenic integral membrane proteins of *Borrelia burgdorferi* are lipoproteins," *Infect. Immun.*, 58(4):983-991, 1990.
Burgdorfer et al., "Lyme disease, a tick-borne spirochetosis?,", *Science*, 216:1317-1319, 1982.
Burman et al., "The variable antigens Vmp7 and Vmp21 of the relapsing fever bacterium *Borrelia hermsii* are structurally analogous to the VSG proteins of the African trypanosome," *Molecular Mocrobiology*, 4(10);1715-1726, 1990.
Cadavid et al., "Variability of a bacterial surface protein and disease expression in a possible mouse model of systemic Lyme borreliosis," *J Exp Med*, 179(2):631-42, 1994.
Carroll and Gheradini, "Membrane protein variations assoicated with in vitro passage of *Borrelia burgdorferi*," *Infect. Immun.*, 64:392-398, 1996.
Carter et al., "A family of surface-exposed proteins of 20 kilodaltons in the genus *Borrelia*," *Infect. Immun.*, 62:2792-2799, 1994.
Casjens et al., "Linear chromosomes of Lyme disease agent spirochetes: genetic diversity and conservation of gene order," *J. Bacteriol.*, 177:2769-2780, 1995.
Cluss and Boothby, "Thermoregulation of protein synthesis in *Borrelia burgdorferi*," *Infect. Immun.*, 58(4):1038-1042, 1990.
Database UniProt Online, "Complement C3 precursor (HSE-MSF) 'Contains: Complement C3 beta chain; Complement C3 alpha chain; C3a anaphlyatoxin; Complement C3b alpha' chain; Complement C3c fragment; Complement C3dg fragment; Complement C3g fragment; Complement C3d fragment; Complement C, isoform Short; C3f fragment!. 671 7," Database Accession No. P01027, 1986.
Dever et al., "In vitro antimocrobial susceptibility testing of *Borrelia burgdorferi*: a microdilution MIC method and time-kill studies," *J. Clin. Microbiol.*, 30:2692-2697, 1992.

Donelson, "Mechanisms of antigenic variation in *Borrelia hermsii* and African trypanosomes," *J. Biol. Chem.*, 270:7783-7786, 1995.
Extended European Search Report and Search Opinion issued in European Application No. 10011690.4, mailed Nov. 13, 2012.
Fawcett et al., "Detetion of antibodies to the recombinant p39 protein of *Borrelia burgdorferi* using enzyme immunoassay and immunoblotting," *J. Rheumatology*, 20(4):734-738, 1993.
Fuchs et al., "Molecular analysis and expression of a *Borrelia burgdorferi* gene encoding a 22kDa protein (pC) in *E. coli*," *Mol. Microbiol.*, 6:503-509, 1992.
GenBank Acession No. AAB09432, 1996.
GenBack Acession No. AAB17737, 1996.
GenBack Acession No. AAC45733, 1997.
Grodzicki and Steere, "Comparison of immunoblotting and indirect enzyme-linked immunosorbent assay using different antigen preparations for diagnosing early lyme disease," *J. Infect. Dis.*, 157(4):790-797, 1988.
Hagblom et al., "Intragenic recombination leads to pilus antigenic variation in *Neisseria gonorrhoeae*," *Nature*, 315:156-158, 1985.
Howe et al., "A single recombinant plasmid expressing two major outer surface proteins of the lyme disease spirochete," *Science*, 227:645-646, 1985.
Howe et al., "Organization of genes encoding two outer membrane proteins of the lyme disease agent *Borrelia burgdorferi* within a single transcriptional unit," *Infect. Immun.*, 54:207-212, 1986.
Hudson et al., "Increased expression of *Borrelia burgdorferi* vlsE in response to human endothelial cell membranse," *Mol. Microbiol.*, 41:229-239, 2001.
Hughes and Johnson, "Methylated DNA in *Borrelia* species," *J. Bacteriol.*, 172:6602-6604, 1990.
Hyde et al., "Detection of antigens in urine of mice and humans infected with *Borrelia burgdorferi*, etiologic agent of lyme disease," *Journal of Clinical Microbiology*, 27(1):58-61, 1989.
Indest et al. "Analysis of *Borrelia burgdorferi* vlsE gene expression and recombination in the tick vector," *Infect. Immun.*, 69:7083-7090, 2001.
Jiang et al., "Cross-antigenicity between the major surface proteins (ospA and ospB) and other proteins of *Borrelia burgdorferi*," *J. Immun.*, 144(1):284-289, 1990.
Johnson et al., "Infection of Syrian hamsters with lyme disease spirochetes," *J. Clin. Microbiol.*, 20:1099-1101, 1984.
Karlsson, "Western immunoblot and flagellum enzyme-linked immunosorbent assay for serodiagnosis of lyme borreliosis," *J. Clin. Microbiol.*, 28(9):2148-2150, 1990.
Kawabata et al., "Genetic and immunological analyses of VIs (VMP-like sequences) of *Borrelia burgdorferi*," *Microbial Pathogenesis*, 24:155-165, 1998.
Kitten and barbour, "Juxtaposition of expressed variable antigen genes with a conserved telomere in the bacterium *Borrelia hermsii*," *Proc. Natl. Acad. Sci. USA*, 87:6077-6081, 1990.
Kitten and Barbour, "The relapsing fever agent *Borrelia hermsii* has multiple copies of its chromosome and linear plasmids," *Genetics*, 132:311-324, 1992.
Kitten et al., "Intragenic recombination and a chimeric outer membrane protein in the relapsing fever agent *Borrelia hermsii*," *J. Bacteriol.*, 175(9):2516-2522, 1993.
Koomey et al., "Effects of *recA* mutations on pilus antigenic variation and phase transitions in *Neisseria gonorrhoeae*," *Genetics*, 117:391-398, 1987.
Kupsch et al., "Variable opacity (Opa) outer membrane proteins account for the cell tropisms displayed by *Neisseria gonorrhoeae* for human leukocytes and epithelial cells," *EMBO. J.*, 12:641-650, 1993.
Lambden et al., "Biological properties of two distinct pilus types produced by isogenic variants of *Neisseria gonorrhoeae* P9," *J. Bacteriol.*, 141:393-396, 1980.
LaFebvre et al., "Characterization of *Borrelia burgdorferi* isolates by restriction endonuclease analysis and DNA hybridizaiton," *Journal of Clinical Microbiology*, 27(4):636-639, 1989.
Liang and Philipp, "Anaylsis of antibody response to invariable regions on VIsE, the variable surface antigen of *Borrelia burgdorferi*," *Infect. Immun.*, 67:6702-6706, 1999.

(56) References Cited

OTHER PUBLICATIONS

Liang et al, "Antigenic conservation of an immunodominant invariable region of the LvsE lipoprotein among European pathogenic genospecies of *Borrelia burgdorferi* SL," *J. Infect. Dis.*, 182:1455-1462, 2000.

Liang et al., "An immunodominant conserved region within the variable domain ov VlsE, the variable surface antigen of *Borrelia burgdorferi*," *J. Immunol.*, 163:5566-5573, 1999.

Liang et al., "Characterization of a *Borrelia burgdorferi* VlsE invariable region useful in canine lyme disease serodiagnosis by enzyme-linked immunosorbent assay," *J. Clinical Microbiology*, 38(11):4160-4166, 2000.

Liang et al., "Sensitive and specific serodiagnosis of lyme disease by enzyme-linked immunosorbent assay with a peptide based on an immunodominant conserved region of *Borrelia burgdorferi* VlsE," *J. Clinical Microbiology*, 37(12):3990-3996, 1999.

Livey et al., "Evidence for lateral transfer and recombination in PspC variation in Lyme disease *Borrelia*," *Mol Microbiol.*, 18:257-269, 1995.

Luft et al., "Biochemical and immunological characterization of the surface proteins of *Borrelia burgdorferi*," *Infect. Immun.*, 57(11):3637-3645, 1989.

Marconi et al., "Analysis of the distribution and molecular heterogeneity of the ospD gene among the Lyme disease spriochetes: evidence for lateral gene exchange," *J. Bacteriol.*, 176:4572-4582, 1994.

Marconi, et al., "Variability of osp genes and gene products among species of Lyme disease spirochetes," *Infect. Immun.*, 61:2611-2617, 1993.

Margolis et al., "Homology between *Borrelia burgdorferi* OspC and members of the family of *Borrelia hermsii* variable major proteins," *Gene*, 143:105-110, 1994.

Moody et al., "Lyme borreliosis in a laboratory animals: effect of host species in vitro passage of *Borrelia burgdorferi*," *Am. J. Trop. Med. Hyg.*, 43(1):87-92, 1990.

Norris et al., "High- and low-infectivity phenotypes of clonal populations of in vitro-cultured *Borrelia burgdorferi*," *Infect. Immun.*, 63:2206-2212, 1995.

Norris et al., "Low-passage-associated proteins of *Borrelia burgdoreferi* B31: characterization and molecular cloning of OspD, a surface-exposed, plasmid-encoded lipoprotein," *Infect. Immun.*, 60:4662-4672, 1992.

Office Action issued in European Application No. 03 800 145.9, mailed Jul. 9, 2008.

Office Action issued in European Application No. 03 800 145.9, mailed Mar. 22, 2010.

Office Action issued in European Application No. 03 800 145.9, mailed Dec. 6, 2006.

Office Action issued in European Application No. 10 011 690.4, mailed Dec. 5, 2013.

Office Action issued in U.S. Appl. No. 10/539,956, mailed Jun. 16, 2009.

Office Action issued in U.S. Appl. No. 10/539,956, mailed Jun. 23, 2008.

Office Action issued in U.S. Appl. No. 10/539,956, mailed Mar. 31, 2010.

Office Action issued in U.S. Appl. No. 12/962,154, mailed Mar. 25, 2011.

Office Action issued in U.S. Appl. No. 13/324,357, mailed Jan. 27, 2012.

Office Action issued in U.S. Appl. No. 13/645,950, mailed Jan. 30, 2013.

PCT International Search Report issused in International Application No. PCT/US03/41182, mailed Oct. 15, 2004.

Pennington et al., "Arthritis severity and spirochete burden are determined by serotype in the *Borrelia turicatae*-mouse model of Lyme disease," *Infect Immunology*, 65(1):285-92, 1997.

Persing et al., "Genetic stability of *Borrelia burgdorferi* recovered from chronically infected immunocompetent mice," *Infect. Immun.*, 62:3521-3527, 1994.

Plasterk et al., "Transposition of structural genes to an expression sequence on a linear plasmid causes antigenic variation in the bacterium *Borrelia hermsii*," *Nature*, 318:257-263, 1985.

Purser and Norris, "Correlation between plasmid content and infectivity in *Borrelia burgdorferi*," *Proc. Natl. Acad. Sci. USA*, 97:13865-13870, 2000.

Restrepo and Barbour, "Antigen diversity in the bacterium *B. hermsii* through 'somatic' mutations in rearranged *vmp* genes," *Cell*, 78:867-876, 1994.

Restrepo et al., "Activation of a *vmp* pseudogene in *Borrelia hermsii*: an alternate mechanism of antigenic variation during relapsing fever," *Mol. Microbiol.*, 13:287-299, 1994.

Restrepo et al., "Subtelomeric expression regions of *Borrelia hermsii* linear plasmids are highly polymorphic," *Mol. Microbiol.*, 6:3299-3311, 1992.

Rosa et al., "Directed insertion of a selectable market into a circular plasmid of *Borrelia burgdorferi*," *J. Bacteriol.*, 178:5946-5953, 1996.

Rosa et al., "Recombination between genes encoding major surface proteins A and B of *Borrelia burgdorferi*," *Mol. Microbiol.*, 6:3031-3040, 1992.

Sadziene et al., "Antibody-resistant mutations of *Borrelia burgdorferi*: in vitro selection and characterization," *J. Exp. Med.*, 176:799-809, 1992.

Sadziene et al., "*Borrelia burgdorferi* mutant lacking osp: biological and immunological characterization," *Infection and Immunity*, 63(4):1573-1580, 1995.

Samuels, et al., "Genetic transformation of the lyme disease agent *Borrelia burgdorferi* with coumarin-resistant gyrB," *J. Bacteriol.*, 176:6045-6049, 1994.

Schwan and Simpson, "Factors influencing the antigenic reactivity of *Borrelia burgdorferi* the lyme disease spirochete," *Scand J. Infect. Dis.*, 77:94-101, 1991.

Schwan et al., "Changes in antigenic reactivity of *Borrelia burgdorferi* the lyme disease spirochete, during persistent infection in mice," *Can. J. Microbiol.*, 37:450-454, 1991.

Schwan et al., "Changes in infectivity and plasmid profile of the lyme disease sporochete, *Borrelia burgdorferi*, as a result of in vitro cultivation," *Infect. Immun.*, 56:1831-1836, 1988.

Scriba et al., "The 39-kilodalton protein of *Borrelia burgdorferi*: a target for bactericidal human monoclonal anitbodies," *Infect. Immun.*, 61(10):4523-4526, 1993.

Segel et al., "Antigenic variation of gonococcal pilus involves assembly of separated silent gene segments," *Proc. Natl. Acad. Sci. USA*, 83:2177-2181, 1986.

Seifert and So, "Genetic mechanisms of bacterial antigenic variation," *Microbiol. Rev.*, 52:327-336, 1988.

Simpson et al., "Reactivity of human lyme borreliosis sera with a 39-kilodalton antigen specific to *Borrelia burgdorferi*," *J. Clin. Microbiol.*, 28(6):1329-1337, 1990.

Simpson et al., "Antibody to a 39-kilodalton *Borrelia burgdorferi* antigen (P39) as a marker for infection in experimentally and naturally innoculated animals," *J. Clinical Microb.*, 29(2):236-243, 1991.

Stevenson et al., Expression and gene sequence of outer surface protein C of *Borrelia burgdorferi* reisolated from chronically infected mice, *Infect. Immun.*, 62:3568-3571, 1994.

Stoenner et al., "Antigenic variation of *Borrelia hermsii*," *J. Exp. Med.*, 156:1297-1311, 1982.

Supplementary European Search Report issued in European Application No. 03 800 145.9, mailed Apr. 21, 2006.

Szczepanski and Benach, "Lyme borreliosis: host responses to *Borrelia burgdorferi*," *Microb. Rev.*, 55(1):21-34, 1991.

Thiessen et al., "Evolution of the *Borrelia burgdorferi* outer surface protein OspC," *J. Bacteriol.*, 177:3036-3044, 1995.

Walker et al., "Physical map of the genome of *Treponema pallidum* subsp. *pallidum* (Nichols)," *J. Bacteriol.*, 177:1797-1804, 1995.

Wallich et al., "The *Borrelia burgdorferi* flagellum-associated 41-kilodalton antigen (flagellin): molecular cloning, expression and amplification of the gene," *Infect. Immun.*, 58(6):1711-1719, 1990.

Wang et al., "Analysis of a VMP-like sequence (vls) locus in *Borrelia garinii* and Vls homologues among four *Borrelia burgdorferi* sensu lato species," *FEMS Microbiol. Lett.*, 199:39-45, 2001.

(56) References Cited

OTHER PUBLICATIONS

Wang et al., "Characterization of the vls antigenic variation loci of the Lyme disease spirochaetes *Borrelia garinii* Ip90 and *Borrelia afzelii* ACAI," *Molecular Microbiology*, 47(5):1407-17, 2003.

Wang, et al., "Characteristics of the *vls* Locus of *Borrelia garinii* Ip90," Abstracts of the General Meeting of the American Society for Microbiology 100th General Meeting, 100:275, 2000.

Wilske et al., "Antigenic variation and strain heterogeneity in *Borrelia* spp.," *Res. Microbiol.*, 143:583-596, 1992.

Wise and Weaver, "Detection of the lyme disease bacterium, *Borrelia burgdorferi*, by using the polymerase chain reaction and a nonradioisotopic gene probe," *Journal of Clinical Microbiology*, 29(7):1523-1526, 1991.

Wu and Tokunaga, "Biogenesis of lipoproteins in bacteria," *Curr. Top. Microbiol. Immunol.*, 125:127-157, 1986.

Xu and Johnson, "Analysis and comparison of plasmid profile of *Borrelia burgdorferi* sensu lato strains," *J. Clin. Microbiol.*, 33:2679-2685, 1995.

Xu et al., "Correlation of plasmids with infectivity of *Borrelia burgdorferi* senso stricto type strain B31," *Infect. Immun.*, 64:3870-3876, 1996.

Zhang and Norris, "Genetic variation of the *Borrelia burgdorferi* gene vslE involves cassette-specific, segmental gene conversation," *Infect. Immun.*, 66:3698-3704, 1998.

Zhang and Norris, "Kinetics and in vitro induction of genetic variation of vlsE in *Borrelia burgdorferi*," *Infect. Immun.*, 66:3689-3697, 1998.

Zhang et al., "Antigenic variation in lyme disease borreliae by promiscuous recombination of VMP-like sequence cassettes," *Cell*, 89:275-285, 1997.

\* cited by examiner

VMP-LIKE SEQUENCES OF PATHOGENIC *BORRELIA* SPECIES AND STRAINS

CROSS-REFERENCE TO RELATED APPLICATIONS

This application is a continuation of U.S. patent application Ser. No. 13/645,950, filed Oct. 5, 2012, now U.S. Pat. No. 8,722,871, issued May 13, 2014, which is a divisional of U.S. patent application Ser. No. 13/324,357, filed Dec. 13, 2011, now U.S. Pat. No. 8,283,458, issued Oct. 9, 2012, which is a divisional of U.S. patent application Ser. No. 12/962,154, filed Dec. 7, 2010, now U.S. Pat. No. 8,076,470, issued Dec. 13, 2011, which is a divisional of U.S. patent application Ser. No. 10/539,956, filed on Apr. 6, 2006, now U.S. Pat. No. 7,847,084, issued on Dec. 7, 2010, which is a U.S. national phase application under 35 U.S.C. §371 of International Application No. PCT/US03/041182, filed Dec. 22, 2003, which claims priority to U.S. Provisional Patent Application No. 60/435,077, filed Dec. 20, 2002. The entire text of each of the above-referenced disclosures is specifically incorporated by reference.

This invention was made with government support under AI37277 awarded by the National Institutes of Health. The government has certain rights in the invention.

BACKGROUND OF THE INVENTION

A. Field of the Invention

The invention relates to the field of molecular biology; in particular, to immunogenic compositions and recombinant VMP-like genes useful for treatment and diagnosis of Lyme disease. Also included are methods for the determination of virulence factors in Lyme disease.

B. Description of Related Art

Lyme disease is a bacterial infection caused by pathogenic spirochetes of the genus *Borrelia*. The infection can occur in humans, dogs, deer, mice and other animals, and is transmitted by arthropod vectors, most notably ticks of the genus *Ixodes*. *Borrelia burgdorferi*, the most common cause of Lyme disease in North America, was first cultured in 1982. *B. garinii* and *B. afzelii* are the most common infectious agents of Lyme disease in Europe, and another species, *B. japonicum*, has been described in Japan. These organisms are closely related and cause similar manifestations with multiple stages: an expanding rash at the site of the tick bite (erythema migrans); fever, lymphadenopathy, fatigue, and malaise; effects of disseminated infection, including carditis, meningoradiculitis, and polyarthritis; and chronic manifestations including arthritis and neurologic disorders.

Lyme disease is often difficult to diagnose because of shared manifestations with other disorders, and it can also be refractory to treatment during late stages of the disease. It is most common in areas such as suburban regions of upstate New York and Connecticut, where large populations of deer and white-footed mice serve as the principal mammalian hosts and reservoirs of infection. Approximately 20,000 cases of Lyme disease in humans are reported per year in the United States, and it is also a significant veterinary problem due to a high infection rate of dogs and other domestic animals in endemic regions.

The pathogenic *Borrelia* that cause Lyme disease are able to persist for years in patients or animals despite the presence of an active immune response. Antigenic variation is a mechanism by which members of the genus *Borrelia* may be able to evade the host immune response (Zhang, 1997). Antigenic variation has been defined as changes in the structure or expression of antigenic proteins that occurs during infection at a frequency greater than the usual mutation rate (Borst and Geaves, 1987; Robertson and Meyer, 1992; Seifert and So, 1988).

Relapsing fever is another disease caused by pathogenic *Borrelia*. It has both epidemic and endemic forms. The epidemic form is caused by *B. recurrentis* and is transmitted between humans by lice. It was a major source of morbidity and mortality during World War I, but has been rare since then due largely to public health measures. Endemic relapsing fever is an epizootic infection caused by several *Borrelia* species, including *B. hermsii*. It occurs sporadically among hunters, spelunkers, and others who come in contact with infected soft-bodied ticks of the genus *Ornithidorus*. Relapsing fever is characterized by two or more episodes or "relapses" of high bacteremia (up to $10^8$/ml). The first wave of infection is caused by Borreliae expressing a certain Variable Major Protein (VMP) on their surface (e.g. Vmp21). The gene encoding this VMP is located at a promoter site in the expression plasmid, whereas over 24 nonexpressed copies of different VMP genes are present on the so-called silent plasmid. When the host develops antibodies against the expressed VMP, the organisms of that serotype are destroyed and the patient improves. However, a small proportion of organisms have undergone antigenic switching to a different serotype. Nonreciprocal recombination occurs between the expression plasmid and the silent plasmid, resulting in the insertion of a different VMP gene in the expression site (e.g., Vmp7). The organisms expressing Vmp7 are not affected by the anti-Vmp21 antibodies, and therefore multiply in the host and cause a second episode of the disease. Up to five of these 3-5 day episodes can occur, separated by 1-2 week intervals.

Such well-demarcated episodes of infection do not occur during Lyme disease, and fewer organisms are present in the blood at any stage. However, there are reasons to suspect that similar mechanisms of antigenic variation may occur in *B. afzelii* and other Lyme disease Borreliae such as *B. garinii* and *B. burgdorferi*. The infection, if untreated, commonly persists for months to years despite the occurrence of host antibody and cellular responses; this observation indicates effective evasion of the immune response. Lyme disease may be disabling (particularly in its chronic form), and thus there is a need for effective therapeutic and prophylactic treatment.

Genetic loci analogous to the VMP antigenic variation system have been detected in North American and European Lyme disease *Borrelia* by Southern hybridization and PCR analysis (Wang et al., 2001). In addition, sequences from fragments of vls (VMP-like sequence) silent cassettes have been reported for the *Borrelia burgdorferi* strains 297 and N40, and the *Borrelia garinii* strains Ip90 and A87S (Liang and Philipp, 1999; Wang et al., 2001), (S. Feng and S. W. Barthold, unpublished data). VMP-like sequences of *B. burgdorferi* have been described and patented in U.S. Pat. No. 6,437,116.

Open reading frames in a *B. burgdorferi* plasmid that encode hypothetical proteins resembling the VMP proteins of relapsing fever organisms have been identified (Zhang et al., 1997). The inventors have found that the presence of the plasmid containing these VMP-like sequences in *B. burgdorferi* clones correlates strongly with infectivity (Zhang et al., 1997; Purser and Norris, 2000). Thus it is likely that the proteins encoded by the VMP-like sequences are important in immunoprotection and pathogenesis. Proteins encoded by the VMP-like sequences of *B. burgdorferi* may provide protection when used either alone or in combination with other antigens. They may also be useful for immunodiagnosis.

Greater than 90% of Lyme disease patients beyond the erythema migrans stage from North America and Europe express antibodies against VlsE (Liang et al., 1999; Liang et al., 2000). In addition, mice infected experimentally with *Borrelia afzelii* and *Borrelia garinii* strains express anti-VlsE antibodies (Liang et al., 2000). Finally, a protein product of ~35 kDa expressed by *Borrelia garinii* Ip90 reacts with antibodies against IR6, a peptide corresponding to invariant region 6 of the VlsE cassette region (Liang et al., 1999a). Portions of several vls silent cassettes from *Borrelia garinii* strain A87S have been published (Wang et al., 2001). Further, several amino acid sequences of *Borrelia garinii* Ip90 have been previously characterized by Liang et al. (1999a).

There is a commercial demand for vaccines and diagnostic kits for Lyme disease, both for human and veterinary use. Several companies have active research and development programs in these areas.

SUMMARY OF THE INVENTION

Partial and complete DNA sequences have been determined for several recombinant clones containing DNA encoding VMP-like sequences. The identification and characterization of these sequences now allows: (1) identification of the expressed gene(s) or DNA segments containing open reading frames in several Borreliae; (2) expression of these gene(s) by a recombinant vector in a host organism such as *E. coli*; (3) immunization of laboratory animals with the resulting polypeptide, and determination of protective activity against Borreliae infection; (4) use of antibodies against the expressed protein to identify the reactive polypeptide(s) in Borreliae cells; (5) use of the expressed protein(s) to detect antibody responses in infected humans and animals; (6) determination of the presence, sequence differences, and expression of the VMP-like DNA sequences in other Lyme disease Borreliae.

The invention is contemplated to be useful in the immunoprophylaxis, diagnosis, or treatment of Lyme disease, relapsing fever, or related diseases in humans or animals. It is expected that recombinant or native proteins expressed by the VMP-like genes (or portions thereof) will be useful for (a) immunoprophylaxis against Lyme disease, relapsing fever, or related disorders in humans and animals; (b) immunotherapy of existing Lyme disease, relapsing fever, or related illnesses, by way of immunization or injection of antibodies directed against VMP-like proteins; and (c) immunodiagnosis of Lyme disease, relapsing fever, or related diseases, including their use in kits in which the VMP-like proteins are the sole antigen or one of multiple antigens. The DNA may be employed in: (a) production of recombinant DNA plasmids or other vectors capable of expressing recombinant polypeptides; and (b) design and implementation of nucleic acid probes or oligonucleotides for detection and/or amplification of VMP-like sequences. The latter is expected to have application in the diagnosis of infection with *Borrelia* organisms.

Another aspect of the invention is the method for identification of possible virulence factors. This approach entails subtractive hybridization of target DNA from high infectivity organisms with driver DNA from low-infectivity strains or clones. This procedure greatly enriches for sequences which differ between the high- and low-infectivity strains and thus may encode proteins important in virulence. Of particular utility is the use of closely related isogenic clones that differ in their infectivity; in this case, the DNA differences should be restricted more stringently to those related to infectivity.

The invention is considered to include DNA segments corresponding to 10, 20, 30, and 40 base pairs of the VMP-like sequences; DNA segments inclusive of the entire open reading frames of the VMP-like sequences; shorter DNA segments containing portions of these open reading frames; amino acid sequences corresponding to both conserved and variable regions of the VMP-like sequences; recombinant vectors encoding an antigenic protein corresponding to the above amino acid sequences; recombinant cells where extrachromosomal DNA expresses a polypeptide encoded by the DNA encoding *Borrelia* VMP-like sequences; a recombinant Borreliae or *E. coli* cell containing the DNA encoding VMP-like sequences; methods of preparing transformed bacterial host cells using the DNA encoding the VMP-like polypeptides; methods using the plasmid or another vector to transform the bacterial host cell to express Borreliae polypeptides encoded by the DNA sequences; and methods for immunization of humans or animals with the native Borreliae polypeptides, polypeptides expressed by recombinant cells that include DNA encoding the VMP-like polypeptides, or synthetic peptides that include VMP-like sequences.

Also included in the invention are primer sets capable of priming amplification of the VMP-like DNA sequences; kits for the detection of Borreliae nucleic acids in a sample, the kits containing a nucleic acid probe specific for the VMP-like sequences, together with a means for detecting a specific hybridization with the probe; kits for detection of antibodies against the VMP-like sequences of Borreliae and kits containing a native, recombinant, or synthetic VMP-like polypeptide, together with means for detecting a specific binding of antibodies to the antigen.

A preferred embodiment of the present invention is an isolated nucleic acid comprising a nucleotide sequence that encodes an antigenic peptide of *Borrelia garinii* or *B. afzelii*. More preferably, the present invention provides an isolated nucleic acid that encodes at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150, 175, 200 or more contiguous amino acids of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:91, SEQ ID NO:93, SEQ ID NO:95, and SEQ ID NO:97. Further, the invention contemplates any range derivable between any of the above-described integers.

In another embodiment, the present invention provides an isolated nucleic acid comprising 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 150, 175, 200, 300, 400, 500 or more contiguous nucleotides of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:28, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:88, SEQ ID NO:89, SEQ ID NO:90, SEQ ID NO:92, SEQ ID NO:94, and SEQ ID NO:96. Further, the invention contemplates any range derivable between any of the above-described integers.

In yet another embodiment, the isolated nucleic acid comprises a complement to or a degenerate variant of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68. 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 150, 175, 200, 300, 400, 500 or more contiguous nucleotides of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:28, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:88, SEQ ID NO:89, SEQ ID NO:90, SEQ ID NO:92, SEQ ID NO:94, and SEQ ID NO:96. Further, the invention contemplates any range derivable between any of the above-described integers.

In some embodiments the isolated nucleic acid is a DNA molecule. In other embodiments the isolated nucleic acid is an RNA molecule.

In certain embodiments the invention provides an isolated nucleic acid obtained by amplification from a template nucleic acid using a primer selected from the group consisting of SEQ ID NO:21, SEQ ID NO:22, SEQ ID NO:23, SEQ ID NO:24, SEQ ID NO:25, SEQ ID NO:26, SEQ ID NO:27, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, and SEQ ID NO:107.

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like.

A preferred embodiment of the present invention is an isolated polypeptide comprising 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150, 175, 200 or more contiguous amino acids of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:91, SEQ ID NO:93, SEQ ID NO:95, and SEQ ID NO:97. Further, the invention contemplates any range derivable between any of the above-described integers.

In one aspect, the present invention provides for an isolated polypeptide or an isolated nucleic acid encoding a polypeptide having between about 70% and about 75%; or more preferably between about 75% and about 80%; or more preferably between about 80% and 90%; or even more preferably between about 90% and about 99% of amino acids that are identical to the amino acids of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:91, SEQ ID NO:93, SEQ ID NO:95, and SEQ ID NO:97 or fragments thereof. The percent identity or homology is determined with regard to the length of the relevant amino acid sequence. Therefore, if a polypeptide of the present invention is comprised within a larger polypeptide, the percent homology is determined with regard only to the portion of the polypeptide that corresponds to the polypeptide of the present invention and not the percent homology of the entirety of the larger polypeptide.

In addition, the present invention encompasses fragments of polypeptides or nucleic acids encoding fragments of polypeptides that have between about 70% and about 75%; or more preferably between about 75% and about 80%; or more preferably between about 80% and 90%; or even more preferably between about 90% and about 99% of amino acids that are identical to the amino acids of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:91, SEQ ID NO:93, SEQ ID NO:95, and SEQ ID NO:97 even if the particular fragment itself does not have between about 70% and about 75%; or more preferably between about 75% and about 80%; or more preferably between about 80% and 90%; or even more preferably between about 90% and about 99% amino acid homology with the polypeptides of the present invention.

In another embodiment the invention provides an isolated polypeptide that binds immunologically with antibodies raised against an antigenic polypeptide of *Borrelia garinii* or *B. afzelii*. In a preferred embodiment the antibodies are raised against an antigenic polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150, 175, 200 or more contiguous amino acids of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:91, SEQ ID NO:93, SEQ ID NO:95, and SEQ ID NO:97. Further, the invention contemplates any range derivable between any of the above-described integers.

The polypeptides of the present invention may be fused with other proteins or peptides. Such fusion polypeptides may be useful for purification or immunodetection purposes, for example. In a preferred embodiment the polypeptides of the invention are expressed as fusions with β-galactosidase, avidin, ubiquitin, *Schistosoma japonicum* glutathione S-transferase, multiple histidines, epitope-tags and the like.

Another aspect of the invention comprises vectors that comprise a nucleic acid encoding all or part of a polypeptide of the present invention. The vectors may, for example, be cloning or expression vectors.

In certain embodiments, it is contemplated that particular advantages will be gained by positioning the nucleic acid sequences of the present invention under the control of a promoter. The promoter may be the promoter that is normally associated with the nucleic acid sequence in its natural environment or it may be a recombinant or heterologous promoter. As used herein, a recombinant or heterologous promoter is intended to refer to a promoter that is not normally associated with a vls gene in its natural environment. Such promoters may include those normally associated with other *Borrelia* polypeptide genes, or promoters isolated from any other bacterial, viral, eukaryotic, or mammalian cell. Naturally, it will be important to employ a promoter that effectively directs the expression of the nucleic acid in the particular cell being used.

The promoters employed may be constitutive, or inducible, and can be used under the appropriate conditions to direct high level or regulated expression of the introduced nucleic acid. In preferred embodiments the promoters are lac, T7, Ara, CMV, RSV LTR, the SV40 promoter alone, or the SV40 promoter in combination with the SV40 enhancer.

Another embodiment is a method of preparing a protein composition comprising growing a recombinant host cell comprising a vector that encodes a polypeptide of the present invention under conditions permitting nucleic acid expression and protein production followed by recovering the protein so produced. The host cell, conditions permitting nucleic acid expression, protein production and recovery, will be known to those of skill in the art, in light of the present disclosure of the vls gene. The recombinant host cell may be a prokaryotic cell or a eukaryotic cell.

VMP-like related proteins and functional variants are also considered part of the invention. Thus it is expected that truncated and mutated versions of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:91, SEQ ID NO:93, SEQ ID NO:95, and SEQ ID NO:97 will afford more convenient and effective forms of polypeptides for treatment regimens. Thus, any functional version of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:91, SEQ ID NO:93, SEQ ID NO:95, and SEQ ID NO:97, such as truncated species or homologs, and mutated versions of VMP-like protein are considered as part of the invention.

Another aspect of the invention comprises the recombination of the 14 silent vls cassettes of *B. afzelii* in numerous combinations, providing for example a cocktail of peptide compositions for use as immunogens to develop vaccines for use in Lyme disease and related conditions. Likewise, the 11 silent vls cassettes of *B. garinii* and the 15 silent vls cassettes of *B. burgdorferi* may be recombined in numerous combinations. It is further contemplated by the present invention that these cassettes may be recombined among strains, as well as species of *Borrelia*, providing a cocktail of peptide compositions for use as immunogens to develop vaccines for use in Lyme disease and related conditions.

Pharmaceutical compositions prepared in accordance with the present invention find use in preventing or ameliorating conditions associated with *Borrelia* infections, particularly Lyme disease.

Such methods generally involve administering a pharmaceutical composition comprising an effective amount of a VMP-like antigen of *Borrelia*, such as SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:91, SEQ ID NO:93, SEQ ID NO:95, and SEQ ID NO:97 or various epitopes thereof.

In certain embodiments of the invention a vaccine may comprise a polynucleotide encoding an antigenic polypeptide. In more specific embodiments the polynucleotide may have a sequence of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:28, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:88, SEQ ID NO:89, SEQ ID NO:90, SEQ ID NO:92, SEQ ID NO:94, and SEQ ID NO:96 or various fragments thereof. The vaccines of the present invention may comprise multiple polypeptides and/or polynucleotides.

It will also be understood that, if desired, the nucleic acid segment or gene encoding a VMP-like protein could be administered in combination with further agents, such as, proteins or polypeptides or various pharmaceutically active agents. There is virtually no limit to other components which may also be included, given that the additional agents do not cause a significant adverse effect upon contact with the target cells or host tissues.

Therapeutic kits comprising a polypeptide or nucleic acid of the present invention comprise another aspect of the invention. Such kits will generally contain, in suitable container means, a pharmaceutically acceptable formulation of a polypeptide or nucleic acid of the present invention. The kit may have a single container means that contains a polypeptide or nucleic acid of the present invention or it may have distinct container means for the polypeptide or nucleic acid of the present invention and other reagents that may be included within such kits.

The components of the kit may be provided as liquid solution(s), or as dried powder(s). When the components are provided in a liquid solution, the liquid solution is an aqueous solution, with a sterile aqueous solution being particularly preferred. When reagents or components are provided as a dry powder, the powder can be reconstituted by the addition of a suitable solvent. It is envisioned that the solvent may also be provided in another container means.

In another embodiment, the invention provides diagnostic kits. The diagnostic kits may comprise reagents for detecting VMP-like polypeptides or anti-VMP-like antibodies in a sample, such as required for immunoassay. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, a number of exemplary labels are known in the art and all such labels may be employed in connection with the present invention. The kits may contain antibody-label conjugates either in fully conjugated form, in the form of intermediates, or as separate moieties to be conjugated by the user of the kit.

The container means will generally include at least one vial, test tube, flask, bottle, syringe or other container means, into which the antigen or antibody may be placed, and preferably suitably aliquoted. Where a second binding ligand is provided, the kit will also generally contain a second vial or other container into which this ligand or antibody may be placed. The kits of the present invention will also typically include a means for containing the antibody, antigen, and reagent containers in close confinement for commercial sale. Such containers may include injection or blow-molded plastic containers into which the desired vials are retained.

In another aspect, the present invention contemplates an antibody that is immunoreactive with a polypeptide of the invention. An antibody can be a polyclonal or a monoclonal antibody. In a preferred embodiment, an antibody is a monoclonal antibody.

Antibodies, both polyclonal and monoclonal, specific for VMP-like polypeptides and particularly those represented by SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:91, SEQ ID NO:93, SEQ ID NO:95, and SEQ ID NO:97 or variants and epitopes thereof, may be prepared using conventional immunization techniques, as will be generally known to those of skill in the art.

In related embodiments, the invention provides methods of using the antibodies of the invention. In preferred embodiments, the antibodies may be used in immunochemical procedures, such as ELISA and Western blot methods. In other embodiments, the antibodies may be used in purifying native or recombinant VMP-like polypeptides, inhibition studies, and immunolocalization studies.

Table 1 below provides the SEQ ID NO, the GenBank accession number, if any, and a brief description of the sequences described herein.

TABLE 1

| SEQ ID NO. | GENBANK NO. | DESCRIPTION |
|---|---|---|
| SEQ ID NO: 1 | U76405 | *B. burgdorferi* vlsE gene allele vlsE1 |
| SEQ ID NO: 2 | AAC45733 | Translation of *B. burgdorferi* vlsE1 gene |
| SEQ ID NO: 3 | L04788 | *B. hermsii* vmp17 gene |
| SEQ ID NO: 4 | AAA22963 | Translation of *B. hermsii* vmp17 gene |
| SEQ ID NO: 5 | AY100629 | RT-PCR product of *B. afzelii* strain ACAI clone 2622 vlsE |
| SEQ ID NO: 6 | AAM77200 | Translation of AY100629 |
| SEQ ID NO: 7 | AY100630 | RT-PCR product of *B. afzelii* strain ACAI clone 2624a vlsE |
| SEQ ID NO: 8 | AAM77201 | Translation of AY100630 |
| SEQ ID NO: 9 | AY100631 | RT-PCR product of *B. afzelii* strain ACAI clone 2624b vlsE |
| SEQ ID NO: 10 | AAM77202 | Translation of AY100631 |
| SEQ ID NO: 11 | AY100632 | RT-PCR product of *B. afzelii* strain ACAI clone 2625 vlsE |
| SEQ ID NO: 12 | AAM77203 | Translation of AY100632 |
| SEQ ID NO: 13 | AY100634 | RT-PCR product of *B. garinii* strain Ip90 clone 17 vlsE |
| SEQ ID NO: 14 | AAM77204 | Translation of AY100634 |
| SEQ ID NO: 15 | AY100635 | RT-PCR product of *B. garinii* strain Ip90 clone 20 vlsE |
| SEQ ID NO: 16 | AAM77205 | Translation of AY100635 |
| SEQ ID NO: 17 | AY100636 | RT-PCR product of *B. garinii* strain Ip90 clone 21 vlsE |
| SEQ ID NO: 18 | AAM77206 | Translation of AY100636 |
| SEQ ID NO: 19 | AY100637 | RT-PCR product of *B. garinii* strain Ip90 clone 23 vlsE |
| SEQ ID NO: 20 | AAM77207 | Translation of AY100637 |
| SEQ ID NO: 21 | N/A | Primer 4540 (Wang et al., 2001) |
| SEQ ID NO: 22 | N/A | Primer 4548 (Wang et al., 2001) |
| SEQ ID NO: 23 | N/A | Primer 4545 (Wang et al., 2001) |
| SEQ ID NO: 24 | N/A | Primer 4587 (Wang et al., 2001) |
| SEQ ID NO: 25 | N/A | Primer 4588 (Wang et al., 2001) |
| SEQ ID NO: 26 | N/A | Primer 4470 (Wang et al., 2001) |
| SEQ ID NO: 27 | N/A | Primer 4471 (Wang et al., 2001) |
| SEQ ID NO: 28 | AY100633 | *B. garinii* vls silent cassette locus |
| SEQ ID NO: 29 | AY100633 | *B. garinii* upstream ORF |
| SEQ ID NO: 30 | AAN87823 | Translation of *B. garinii* upstream ORF |
| SEQ ID NO: 31 | AY100633 | *B. garinii* 5' vlsE homolog |
| SEQ ID NO: 32 | AAN87824 | Translation of *B. garinii* 5' vlsE homolog |
| SEQ ID NO: 33 | AY100633 | *B. garinii* vls1 |
| SEQ ID NO: 34 | AAN87825 | Translation of *B. garinii* vls1 |
| SEQ ID NO: 35 | AY100633 | *B. garinii* vls2 |
| SEQ ID NO: 36 | AAN87826 | Translation of *B. garinii* vls2 |
| SEQ ID NO: 37 | AY100633 | *B. garinii* vls3 |
| SEQ ID NO: 38 | AAN87827 | Translation of *B. garinii* vls3 |
| SEQ ID NO: 39 | AY100633 | *B. garinii* vls4 |
| SEQ ID NO: 40 | AAN87828 | Translation of *B. garinii* vls4 |
| SEQ ID NO: 41 | AY100633 | *B. garinii* vls5 |
| SEQ ID NO: 42 | AAN87829 | Translation of *B. garinii* vls5 |
| SEQ ID NO: 43 | AY100633 | *B. garinii* vls6 |
| SEQ ID NO: 44 | AAN87830 | Translation of *B. garinii* vls6 |
| SEQ ID NO: 45 | AY100633 | *B. garinii* vls7 |
| SEQ ID NO: 46 | AAN87831 | Translation of *B. garinii* vls7 |
| SEQ ID NO: 47 | AY100633 | *B. garinii* vls8 |

TABLE 1-continued

| SEQ ID NO. | GENBANK NO. | DESCRIPTION |
|---|---|---|
| SEQ ID NO: 48 | AAN87832 | Translation of B. garinii vls8 |
| SEQ ID NO: 49 | AY100633 | B. garinii vls9 |
| SEQ ID NO: 50 | AAN87833 | Translation of B. garinii vls9 |
| SEQ ID NO: 51 | AY100633 | B. garinii vls10 |
| SEQ ID NO: 52 | AAN87834 | Translation of B. garinii vls10 |
| SEQ ID NO: 53 | AY100633 | B. garinii vls11 |
| SEQ ID NO: 54 | AAN87835 | Translation of B. garinii vls11 |
| SEQ ID NO: 55 | AY100633 | B. garinii truncated gene |
| SEQ ID NO: 56 | AAN87823 | Translation of B. garinii truncated gene |
| SEQ ID NO: 57 | AY100628 | vls silent cassette locus of B. afzelii |
| SEQ ID NO: 58 | AY100628 | B. afzelii vls1 |
| SEQ ID NO: 59 | AAN87809 | Translation of B. afzelii vls1 |
| SEQ ID NO: 60 | AY100628 | B. afzelii vls2 |
| SEQ ID NO: 61 | AAN87810 | Translation of B. afzelii vls2 |
| SEQ ID NO: 62 | AY100628 | B. afzelii vls3 |
| SEQ ID NO: 63 | AAN87811 | Translation of B. afzelii vls3 |
| SEQ ID NO: 64 | AY100628 | B. afzelii vls4 |
| SEQ ID NO: 65 | AAN87812 | Translation of B. afzelii vls4 |
| SEQ ID NO: 66 | AY100628 | B. afzelii vls5 |
| SEQ ID NO: 67 | AAN87813 | Translation of B. afzelii vls5 |
| SEQ ID NO: 68 | AY100628 | B. afzelii vls6 |
| SEQ ID NO: 69 | AAN87814 | Translation of B. afzelii vls6 |
| SEQ ID NO: 70 | AY100628 | B. afzelii vls7 |
| SEQ ID NO: 71 | AAN87815 | Translation of B. afzelii vls7 |
| SEQ ID NO: 72 | AY100628 | B. afzelii vls8 |
| SEQ ID NO: 73 | AAN87816 | Translation of B. afzelii vls8 |
| SEQ ID NO: 74 | AY100628 | B. afzelii vls9a |
| SEQ ID NO: 75 | AAN87817 | Translation of B. afzelii vls9a |
| SEQ ID NO: 76 | AY100628 | B. afzelii vls10 |
| SEQ ID NO: 77 | AAN87818 | Translation of B. afzelii vls10 |
| SEQ ID NO: 78 | AY100628 | B. afzelii vls11 |
| SEQ ID NO: 79 | AAN87819 | Translation of B. afzelii vls11 |
| SEQ ID NO: 80 | AY100628 | B. afzelii vls12 |
| SEQ ID NO: 81 | AAN87820 | Translation of B. afzelii vls12 |
| SEQ ID NO: 82 | AY100628 | B. afzelii vls13 |
| SEQ ID NO: 83 | AAN87821 | Translation of B. afzelii vls13 |
| SEQ ID NO: 84 | AY100628 | B. afzelii vls14 |
| SEQ ID NO: 85 | AAN87822 | Translation of B. afzelii vls14 |
| SEQ ID NO: 86 | AY100628 | B. afzelii conserved protein |
| SEQ ID NO: 87 | AAN87823 | Translation of B. afzelii conserved protein |
| SEQ ID NO: 88 | N/A | Nucleotides 1-2775 of AY100633 (B. garinii) |
| SEQ ID NO: 89 | N/A | Nucleotides 3823-5897 of AY100633 (B. garinii) |
| SEQ ID NO: 90 | N/A | Fragment of B. garinii vls5 |
| SEQ ID NO: 91 | N/A | Amino acids 1-184 of AAN87829 (B. garinii) |
| SEQ ID NO: 92 | N/A | Fragment of B. garinii vls8 |
| SEQ ID NO: 93 | N/A | Amino acids 56-195 of AAN87832 (B. garinii) |
| SEQ ID NO: 94 | N/A | Expressed ORF in pBG-10-1 |
| SEQ ID NO: 95 | N/A | Protein sequence expressed by pBG-10-1 |
| SEQ ID NO: 96 | N/A | Expressed ORF in pBA-13-1 |
| SEQ ID NO: 97 | N/A | Protein sequence expressed by pBA-13-1 |
| SEQ ID NO: 98 | N/A | Primer |
| SEQ ID NO: 99 | N/A | Primer |
| SEQ ID NO: 100 | N/A | Primer |
| SEQ ID NO: 101 | N/A | Primer |
| SEQ ID NO: 102 | N/A | Primer |
| SEQ ID NO: 103 | N/A | Primer |
| SEQ ID NO: 104 | N/A | Primer |
| SEQ ID NO: 105 | N/A | Primer |
| SEQ ID NO: 106 | N/A | 17-bp direct repeat of B. burgdorferi |
| SEQ ID NO: 107 | N/A | EcoRI linker |

BRIEF DESCRIPTION OF THE DRAWINGS

(FIG. 1A) B. garinii Ip90. The cross-hatched bar indicates the location of P7-1 clone (Liang and Philipp, 1999) in the vls locus of Ip90. The locations of the telomeric repeat sequences (TRS) and the vlsE-like sequence are shown. (FIG. 1B) B. afzelii ACAI. The location and orientation of the vls cassettes and other features of this region are indicated as described above.

FIGS. 2A-2B. Alignment of predicted amino acid sequences of vls silent cassettes of B. afzelii ACAI (FIG. 2A) and B. garinii Ip90 (FIG. 2B) with the cassette region of B. burgdorferi B31 vlsE. Alignment for B. afzelii ACAI is based on cassette 1 and for B. garinii Ip90 based on cassette 10. The underlined residues at the end of cassette 9 in panel A are a continuation of the cassette following a frameshift. Identical amino acid sequences are shown as periods. The variable regions are indicated by shaded boxes and the lines under the shaded boxes represent the corresponding variable regions of B. burgdorferi B31. Gaps and predicted stop codons are indicated as dashes and asterisks, respectively. Cassette 1 (SEQ ID NO:59), cassette 2 (SEQ ID NO:61), cassette 3 (SEQ ID NO:63), cassette 4 (SEQ ID NO:65), cassette 5 (SEQ ID NO:67), cassette 6 (SEQ ID NO:69), cassette 7 (SEQ ID NO:71), cassette 8 (SEQ ID NO:73), cassette 9 (SEQ ID NO:75), cassette 10 (SEQ ID NO:77), cassette 11 (SEQ ID NO:79), cassette 12 (SEQ ID NO:81), cassette 13 (SEQ ID NO:83), cassette 14 (SEQ ID NO:85), cassette B31 vlsE (SEQ ID NO:108).

FIGS. 4A-4B. Alignment of the predicted amino acid sequences based on RT-PCR products from vlsE variants of B. afzelii ACAI (FIG. 4A) and B. garinii Ip90 (FIG. 4B). Alignments for B. afzelii ACAI and B. garinii Ip90 are based on the sequences of clones 2622 and 17, respectively. The variable regions labeled VR-I through VR-VI (FIG. 4A) and VR-II through VR-V (FIG. 4B) are indicated by boxes. Only portions of VR-I and VR-VI are shown for ACAI. Identical amino acid sequences and gaps are shown as periods and dashes, respectively. Solid and dotted bars indicate the predicted minimum and maximum possible recombination events, respectively, resulting in the given vlsE variant. Solid lines indicate 100% sequence identity between the given position in the variant and silent cassette(s) indicated. Dashed lines mark the limits of maximum recombination. Asterisks above certain residues indicate sites of possible point mutations, as explained in the text. In regions where more than one silent cassette matches the variant amino acid sequence, the matches were further analyzed at the nucleotide level. ACAI VlsE Clone 2622 (SEQ ID NO:109), ACAI VlsE Clone 2624a (SEQ ID NO:110), ACAI VlsE Clone 2624b (SEQ ID NO:111), ACAI VlsE Clone 2625 (SEQ ID NO:112), Ip90 VlsE Clone 17 (SEQ ID NO:113), Ip90 VlsE Clone 20 (SEQ ID NO:114), Ip90 VlsE Clone 21 (SEQ ID NO:115), Ip90 VlsE Clone 23 (SEQ ID NO:116).

DETAILED DESCRIPTION OF ILLUSTRATIVE EMBODIMENTS

Figure 1A:
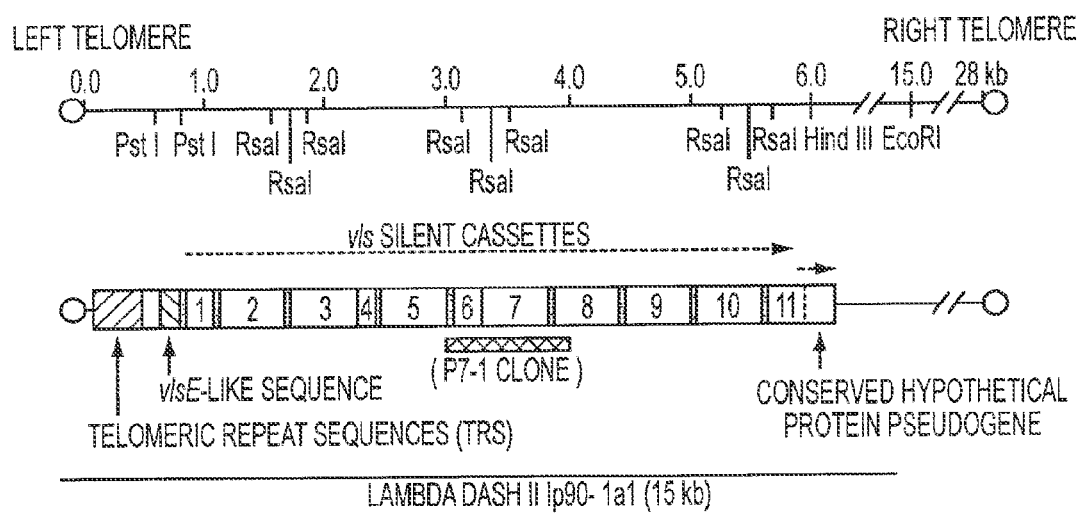
FIGS. 1A-1B. Arrangement of vls silent cassette regions of B. garinii Ip90 and B. afzelii ACAI. The orientation of the silent cassettes is indicated by a dashed arrow. Direct repeats are indicated by heavily weighted lines between silent cassettes. The location and orientation of conserved hypothetical protein genes are indicated at the 3' end of each locus. Restriction sites used for cloning and sequencing are also shown.

The present work discloses the identification and characterization of an elaborate genetic system in the Lyme disease spirochete *Borrelia* that promotes extensive antigenic variation of a surface-exposed lipoprotein, VlsE.

Hybridization with the *B. burgdorferi* B31 vls silent cassette sequence in recombinant plasmid pJRZ53 was used in identifying the plasmids and DNA fragments containing vls sequences in *B. garinii* Ip90 and *B. afzelii* ACAI. The pJRZ53 probe hybridized exclusively to plasmids with an approximate size of 28 kb in both ACAI and Ip90. DNA fragments from these *B. garinii* Ip90 and *B. afzelii* ACAI plasmids were inserted into a recombinant lambda bacteriophage vector (lambda-DashI) and sequenced. The results showed *B. garinii* Ip90 to consist of 11 vls silent cassettes and *B. afzelii* ACAI of 14 vls silent cassettes.

With the exception of the junctions at vls3/4 and vls6/7, the 11 vls silent cassettes of Ip90 are flanked by 18 bp direct repeat sequences in the 6 kb region. However, several of these cassettes (vls1, vls4, vls6, and vls11) are truncated (189 to 288 bp in length) relative to the other, full-length cassettes ranging in size from 573 to 594 bp. Unlike Ip90 and B31, the ACAI vls locus is located on an internal EcoRI fragment of a 28-kb linear plasmid, and its location relative to the plasmid telomeres is not known. The ACAI vls locus contained 13 complete and 1 partial silent cassettes with each cassette being flanked by an 18 bp direct repeat sequence.

These silent cassettes share 90% to 97% nucleotide sequence identity with one another within the Ip90 vls locus and 84% to 91% within the ACAI vls locus. Amino acid similarity to the B31 silent cassettes ranges from 51% to 62% for the Ip90 vls silent cassettes and from 50% to 65% for the ACAI vls silent cassettes. The nucleotide sequence and predicted amino acid sequence of vlsE in *B. burgdorferi* is provided in SEQ ID NO:1 and SEQ ID NO:2, respectively. The vlsE expression sites of Ip90 and ACAI have not been isolated, but transcripts of vlsE have been detected by reverse transcriptase PCR for both Ip90 and ACAI. In addition, the occurrence of sequence variation within the vlsE cassette region of these transcripts was verified. Mice infected experimentally with *B. garinii* and *B. afzelii* strains have been shown to express anti-VlsE antibodies (Liang et. al., 2000a). Additionally, a protein product of ~35 kDa expressed by *B. garinii* Ip90 reacts with antibodies against IR6, a peptide corresponding to invariant region 6 of the VlsE cassette region (Liang et. al., 1999a). The characteristics of the vls loci present in *B. garinii* Ip90 and *B. afzelii* ACAI are therefore similar to those found in *B. burgdorferi* B31.

Genetic variation involved in multi-gene families has been described in several other pathogenic microorganisms (Borst and Geaves, 1987; Borst et al., 1995; Donelson, 1995). In the context of combinatorial recombination, the genetic variation at the vlsE site is similar to that of the pilin-encoding genes of *Neisseria gonorrhoeae* (Seifert and So, 1988). The gonococcal pilus is primarily composed of repeating subunits of an 18-kilodalton pilin protein and is required for adherence of the bacterium to a variety of human cells (Swanson and Koomey, 1989). While the complete pilin genes are expressed only at two expression sites (pilE1 and pilE2), multiple silent copies (pilS) containing portions of the pilin genes are found over a wide range on the gonococcal chromosome (Haas and Meyer, 1986). Through multiple combinatorial recombination events, a single gonococcal clone expressing one pilin stereotype can give rise to a large number of progeny that express antigenically distinctive pilin variants (Meyer et al., 1982; Hagblom et al., 1985; Segal et al., 1986). The recombination between the expression and silent loci occurs predominantly through a non-reciprocal gene conversion mechanism (Haas and Meyer, 1986; Koomey et al., 1987).

The coding sequences of the *Neisseria* pilin variants are divided into constant, semi-variable, and hypervariable regions (Haas and Meyer, 1986), which are analogous to the conserved and variable regions of the Vls cassettes. The constant regions and a conserved DNA sequence (Sma/Cla repeat) located at the 3' end of all pilin loci are thought to pair the regions involved in recombination events (Wainwright et al., 1994). In this context, the 18-bp direct repeats and the conserved regions of the vls cassettes in *B. garinii* and *B. afzelii* may play a similar role in recombination events. The silent loci of gonococcal pilin genes contain different regions of the complete pilin genes (Haas and Meyer, 1986), whereas the silent vls cassettes of *Borrelia* represent only the central cassette region of the vlsE gene.

Non-reciprocal recombinations also occur between the expressed and the silent genes encoding variant surface glycoproteins (Vsgs) in African trypanosomes (Donelson, 1995). Based on similarities between the vls locus and the multi-gene families of the other pathogenic microorganisms and experimental data (Zhang and Norris, 1998b), it is likely that a unidirectional gene conversion mechanism is also active in the Vls locus. The exact mechanism of vls recombination remains to be determined.

Variation of Borreliae surface proteins such as VlsE may also affect the organism's virulence and its ability to adapt to different micro-environments during infection of the mammalian host. Recent studies of a *Borrelia* turicatae mouse infection model that resembles Lyme disease showed that one serotype expressing VmpB exhibited more severe arthritic manifestations, whereas another expressing VmpA had more severe central nervous system involvement. The numbers of Borreliae present in the joints and blood of serotype B-infected mice were much higher than those of mice infected with serotype A, consistent with a relationship between Vmp serotype and disease severity. Antigenic variation of *Neisseria* pilin (Lambden et al., 1980; Rudel et al., 1992; Nassif et al., 1993; Jonsson et al, 1994) and Opa proteins (Kupsch et al, 1993) is known to affect adherence of the organisms to human leukocytes and epithelial cells.

A. Antigenic Variation in *B. hermsii*

A complex antigenic variation mechanism has been characterized in *Borrelia hermsii*, a relative of *B. afzelii* and *B. garinii* that causes relapsing fever (Balmelii and Piffatetti, 1996; Barbour, 1993; Donelson, 1995). Surface-exposed lipoproteins called variable major proteins (Vmps) are encoded by homologous genes located in 28- to 32-kb linear plasmids with covalently closed telomeres (Barbour and Garon, 1987; Kitten and Barbour, 1990). The vmp genes have been subdivided into two groups: small and large (Restrepo et al., 1992). Large vmp genes such as vmp7 and vmp17 and small vmp genes such as vmp1 and vmp3 are approximately 1 kb and 0.6 kb in size, respectively. Each organism contains both small and large vmp genes in an unexpressed (silent) form in the so-called storage plasmids (Plasterk et al., 1985). Only one vmp gene located near one of the telomeres of a different plasmid (called the expression plasmid) is expressed in each organism (Kitten and Barbour, 1990; Barbour et al., 1991a). The nucleotide sequence and predicted amino acid sequence of an expressed vmp gene of *B. hermsii* are provided in SEQ ID NO:3 and SEQ ID NO:4, respectively. Antigenic variation occurs when the expressed vmp is replaced completely or partially by one of the silent vmp genes at the telomeric expression site through interplasmic recombination (Meier et al., 1985; Plasterk et al., 1985; Barbour et al., 1991b), intraplasmic recombination (Restrepo et al., 1994), and post-switch rearrangement (Restrepo and Barbour, 1994). The antigenic switch occurs spontaneously at a frequency of $10^{-3}$ to $10^{-4}$ per generation (Stoenner et al., 1982).

B. Identification of vls

The present invention discloses a repetitive DNA sequence ~500 bp in length, which is present in multiple, nonidentical copies in a 28-kb linear plasmid of infectious *Borrelia burgdorferi*, *Borrelia garinii*, and *Borrelia afzelii*, the causative agents of Lyme disease. These DNA sequences encode polypeptides that have sequence similarity to the Variable Major Proteins (VMPs) of relapsing fever Borreliae (such as *B. hermsii*). VMPs are highly antigenic surface proteins, which the relapsing fever Borreliae are able to change through a genetic recombination mechanism, thereby evading the immune response. Antibodies against a particular VMP protein are protective, resulting in rapid clearance of bacteria of the corresponding serotype. In *Borrelia burgdorferi*, *Borrelia garinii*, and *Borrelia afzelii*, VMP-like sequences (vls) are present on a 28-kb linear plasmid, and this plasmid appears to encode virulence factor(s) required for infectivity.

C. ELISAs

ELISAs may be used in conjunction with the invention. In an ELISA assay, proteins or peptides incorporating *Borrelia* Vls antigenic sequences are immobilized onto a selected surface, preferably a surface exhibiting a protein affinity such as the wells of a polystyrene microtiter plate. The antigenic proteins or peptides may be isolated or comprised within larger polypeptides. For example, an antigenic Vls peptide may be comprised within a larger polypeptide that also includes a moiety that is useful for anchoring the polypeptide to the selected surface. The anchoring moiety may be an amino acid sequence. Virtually any amino acid sequence may be added to the antigenic Vls sequence so long as it does not confound the results of the ELISA assay. Those of skill in the art would know how to select amino acid sequences that are antigenically neutral with regard to antibodies in the biological sample (including, but not limited to, whole blood, plasma, serum, cerebrospinal fluid, other body fluids, or tissue extracts) that is being tested.

After washing to remove incompletely adsorbed material, it is desirable to bind or coat the assay plate wells with a nonspecific protein that is known to be antigenically neutral with regard to the biological sample such as bovine serum albumin (BSA), casein or solutions of powdered milk. This allows for blocking of nonspecific adsorption sites on the immobilizing surface and thus reduces the background caused by nonspecific binding of antibodies in the biological sample onto the surface.

After binding of antigenic material to the well, coating with a non-reactive material to reduce background, and washing to remove unbound material, the immobilizing surface is contacted with the antisera or clinical or biological sample to be tested in a manner conducive to immune complex (antigen/antibody) formation. Such conditions preferably include diluting the sample with diluents such as BSA, solution or phosphate buffered saline (PBS)/Tween®. These added agents also tend to assist in the reduction of nonspecific background. The layered biological sample preparation is then allowed to incubate in the well for from about 1 to about 4 hr, at temperatures preferably on the order of about 25° to about 37° C. Following incubation with the diluted or undiluted biological sample, the antisera-contacted surface is washed so as to remove non-immunocomplexed material. A preferred washing procedure includes washing with a solution such as PBS/Tween®.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease, alkaline phosphatase or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

Alternatively, the ELISA assay may be performed where antibodies that bind immunologically to *Borrelia* Vls antigenic sequences are immobilized onto a selected surface. After binding of the antibody to the surface, coating with a non-reactive material to reduce background, and washing to remove unbound material, the immobilizing surface is contacted with the biological sample to be tested in a manner conducive to immune complex (antigen/antibody) formation. Following formation of specific immunocomplexes between the test sample and the bound antibody, and subsequent washing, immunocomplex formation may be determined using a second, labeled antibody. This approach enables the detection of an antigen in a biological sample.

D. Epitopic Core Sequences

The present invention is also directed to protein or peptide compositions, free from total cells and other peptides, which comprise a purified protein or peptide which incorporates an epitope that is immunologically cross-reactive with one or more anti-*Borrelia* VMP-like antibodies.

As used herein, the term "incorporating an epitope(s) that is immunologically cross-reactive with one or more anti-VMP-like antibodies" is intended to refer to a peptide or protein antigen which includes a primary, secondary or tertiary structure similar to an epitope located within a *Borrelia* VMP-like polypeptide. The level of similarity will generally be to such a degree that polyclonal antibodies directed against the *Borrelia* VMP-like polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of *Borrelia* VMP-like epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 5 to about 50 amino acids in length, and more preferably about 8 to about 40 amino acids in length. Such peptides may be isolated or comprised within a larger polypeptide. It is proposed that shorter antigenic *Borrelia* VMP-like-derived peptide sequences will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitope peptide directed to *Borrelia* VMP-like and *Borrelia* VMP-like-related sequences. It is proposed that these regions represent those which are most likely to promote T-cell or B-cell stimulation in an animal, and, hence, elicit specific antibody production in such an animal.

An epitopic core sequence, as used herein, is a relatively short stretch of amino acids that is "complementary" to, and therefore will bind, antigen binding sites on vls protein-specific antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence expected by the present disclosure would generally be on the order of about 5 amino acids in length, with sequences on the order of 8 or 25 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins. Computerized peptide sequence analysis programs (e.g., DNAStar® software, DNAStar, Inc., Madison, Wis.) may also be useful in designing synthetic *Borrelia* VMP-like peptides and peptide analogs in accordance with the present disclosure. In addition, epitope mapping may be performed, in which overlapping peptides corresponding to all regions of the protein are synthesized and tested for reactivity with antibodies directed against vls sequences. Reactivity of serum from animals or humans infected with Lyme disease *Borrelia*, and nonreactivity with serum from animals or patients that do not have Lyme disease would help to define those peptides that react sensitively and specifically with antibodies against Lyme disease *Borrelia*.

An epitopic core sequence may be comprised within a larger polypeptide. For example, an epitopic core sequence of the present invention may be comprised in a larger polypeptide, which also comprises a moiety that is useful for anchoring the polypeptide to the selected surface. The anchoring moiety may be an amino acid sequence. These polypeptides would be particularly useful in the various immunoassay methods of the present invention. In a particular example, a peptide or polypeptide of the present invention may have a cysteine added at one end of the amino acid sequence to permit the addition of biotin. The biotinylated peptides or polypeptides could then be captured on streptavidin-coated surfaces. Those of skill in the art would know how to identify which polypeptides react sensitively and specifically with antibodies against Lyme disease *Borrelia*. For example, reactivity of serum from animals or humans infected with Lyme disease *Borrelia*, and nonreactivity with serum from animals or patients that do not have Lyme disease would help to define those polypeptides that react sensitively and specifically with antibodies against Lyme disease *Borrelia*.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

E. Antibodies

Means for preparing and characterizing antibodies are well known in the art. An antibody can be a polyclonal or a monoclonal antibody.

The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of antiantisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvant and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified LCRF protein, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages, but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described, and those using polyethylene glycol (PEG), such as 37% (v/v) PEG. The use of electrically induced fusion methods is also appropriate.

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

F. Immunoprecipitation

The antibodies of the present invention are particularly useful for the isolation of antigens by immunoprecipitation. Immunoprecipitation involves the separation of the target antigen-antibody complexes from a complex mixture, and is used to discriminate or isolate minute amounts of protein. For the isolation of membrane proteins cells must be solubilized into detergent micelles. Nonionic detergents are preferred, since other agents, such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g., enzyme-substrate pairs.

G. Western Blots

The compositions of the present invention will find great use in immunoblot or western blot analysis. The anti-Borrelia VMP-like antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

H. Vaccines

An important aspect of the invention is the recognition that Borrelia VMP-like sequences recombine at the vlsE site, with the result that antigenic variation is virtually limitless. Multiclonal populations therefore can exist in an infected patient so that immunological defenses are severely tested if not totally overwhelmed. Thus there is now the opportunity to develop more effective combinations of immunogens for protection against Borrelia infections or as preventive inoculations such as in the form of cocktails of multiple antigenic variants based on a series of combinatorial VMP-like antigens.

VMP-like protein preparations may be administered in several ways, either locally or systemically in pharmaceutically acceptable formulations. Amounts appropriate for administration are determined on an individual basis depending on such factors as age and sex of the subject, as well as physical condition and weight. Such determinations are well within the skill of the practitioner in the medical field.

Other methods of administration may include injection of Borrelia VMP-like DNAs into vaccine recipients (human or animal) driven by an appropriate promoter such as CMV, (so called DNA vaccines). Such preparations could be injected subcutaneously or intramuscularly, administered orally, or introduced into the skin on metal particles propelled by high-pressure gas. DNA vaccination techniques are currently well past the initial development stage and have shown promise as vaccination strategies.

The present invention contemplates vaccines for use in both active and passive immunization embodiments. Immunogenic compositions, proposed to be suitable for use as a vaccine, may be prepared most directly from immunogenic Borrelia VMP-like peptides prepared in a manner disclosed herein. Preferably the antigenic material is extensively dialyzed to remove undesired small molecular weight molecules and/or lyophilized for more ready formulation into a desired vehicle.

The preparation of vaccines which contain Borrelia VMP-like peptide or polypeptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly. Vaccines may also be adminstered orally. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10 to about 95% of active ingredient, preferably about 25 to about 70%.

The *Borrelia* VMP-like-derived peptides or polypeptides of the present invention may be formulated into the vaccine as neutral or salt forms. It is anticipated that many VMP-like-derived peptides or polypeptides with different sequences could be incorporated into a single vaccine, in effect producing a combinatorial vaccine. Pharmaceutically-acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable oil vehicles such as mannide mono-oleate (Aracel A) or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies. The course of the immunization may be followed by assays for antibodies for the supernatant antigens. The assays may be performed by labeling with conventional labels, such as radionucleotides, enzymes, fluorescents, and the like. These techniques are well known and may be found in a wide variety of patents, such as U.S. Pat. Nos. 3,791,932; 4,174,384 and 3,949,064, as illustrative of these types of assays.

I. Nucleic Acids

The present invention provides the nucleotide sequences of the vls gene in *B. garinii* and *B. afzelii*. It is contemplated that the isolated nucleic acids of the present invention may be put under the control of a promoter. The promoter may be the promoter that is naturally associated with the vls gene or it may be a recombinant or heterologous promoter. As used herein, a recombinant or heterologous promoter is intended to refer to a promoter that is not normally associated with a DNA segment encoding a *Borrelia* VMP-like peptide in its natural environment. Such promoters may include promoters normally associated with other genes, and/or promoters isolated from any viral, prokaryotic (e.g., bacterial), eukaryotic (e.g., fungal, yeast, plant, or animal) cell.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 2001. The promoters employed may be constitutive, or inducible, and can be used under the appropriate conditions to direct high level expression of the introduced DNA segment, such as is advantageous in the large-scale production of recombinant proteins or peptides. Appropriate promoter/expression systems contemplated for use in high-level expression include, but are not limited to, the *Pichia* expression vector system (Pharmacia LKB Biotechnology), a baculovirus system for expression in insect cells, or any suitable yeast or bacterial expression system.

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of *Borrelia* VMP-like peptides or epitopic core regions, such as may be used to generate anti-Borrelia VMP-like antibodies, also falls within the scope of the invention. DNA segments that encode *Borrelia* VMP-like peptide antigens from about 10 to about 100 amino acids in length, or more preferably, from about 20 to about 80 amino acids in length, or even more preferably, from about 30 to about 70 amino acids in length are contemplated to be particularly useful.

In addition to their use in directing the expression of *Borrelia* VMP-like peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least about a 10, 11, 12, 13, 14, 15, 16, 17, 18, or 19 nucleotide long contiguous sequence that has the same sequence as, or is complementary to, an about 10, 11, 12, 13, 14, 15, 16, 17, 18, 19 nucleotide long contiguous DNA segment of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:28, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:88, SEQ ID NO:89, SEQ ID NO:90, SEQ ID NO:92, SEQ ID NO:94, and SEQ ID NO:96 will find particular utility. Longer contiguous identical or complementary sequences, e.g., those of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68. 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 150, 175, 200, 300, 400, 500, (including all intermediate lengths) and those up to and including full-length sequences will also be of use in certain embodiments.

The ability of such nucleic acid probes to specifically hybridize to *Borrelia* VMP-like-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68. 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 150, 175, 200, 300, 400, 500 or more, identical or complementary to the DNA sequence of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:28, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:88, SEQ ID NO:89, SEQ ID NO:90, SEQ ID NO:92, SEQ ID NO:94, and SEQ ID NO:96, are particularly contemplated as hybridization probes for use in, e.g., Southern and Northern blotting. Smaller fragments will generally find use in hybridization embodiments, wherein the length of the contiguous complementary region may be varied, such as between about 10-14 and up to about 100 nucleotides, but larger contiguous complementary stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 15 to about 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as PCR™, by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., conditions of high stringency where one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating *Borrelia* VMP-like-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses.

Of course, for some applications, for example, where one desires to prepare mutants employing a mutant primer strand hybridized to an underlying template or where one seeks to isolate *Borrelia* VMP-like-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

Isolated nucleic acids encoding vls or vls-related genes are contemplated to be particularly useful in connection with this invention. Any recombinant vls combining any of the vlsE expression site loci and/or silent vls cassette would likewise be very useful with the methods of the invention.

Isolation of the DNA encoding VMP-like polypeptides allows one to use methods well known to those of skill in the art, and as herein described, to make changes in the codons for specific amino acids such that the codons are "preferred usage" codons for a given species. Thus for example, preferred codons will vary significantly for bacterial species as compared with mammalian species; however, there are preferences even among related species. Shown below is a preferred codon usage table for humans. Isolation of spirochete DNA encoding VMP-like proteins will allow substitutions for preferred human codons, although expressed polypeptide product from human DNA is expected to be homologous to bacterial VMP-like proteins and so would be expected to be structurally and functionally equivalent to VMP-like proteins isolated from a spirochete. However, substitutions of preferred human codons may improve expression in the human host, thereby improving the efficiency of potential DNA vaccines. This method may also be useful in achieving improved expression of the recombinant VMP-like protein in E. coli or any of a variety of prokaryotic and eukaryotic cells.

To prepare a VMP-like gene segment or cDNA one may follow the teachings disclosed herein and also the teachings of any patents or scientific documents specifically referenced herein. One may obtain a rVMP- or other related-encoding DNA segments using molecular biological techniques, such as polymerase chain reaction (PCR™) or screening of a cDNA or genomic library, using primers or probes with sequences based on the above nucleotide sequence. Such single- or double-stranded DNA segments may be readily prepared by, for example, directly synthesizing the fragments by chemical means, by application of nucleic acid reproduction technology, such as the PCR™ technology of U.S. Pat. Nos. 4,683,195 and 4,683,202 (herein incorporated by reference). The practice of these techniques is a routine matter for those of skill in the art, as taught in various scientific texts (see e.g., Sambrook et al., 2001), incorporated herein by reference. Certain documents further particularly describe suitable mammalian expression vectors, e.g., U.S. Pat. No. 5,168,050, incorporated herein by reference. The VMP-like genes and DNA segments that are particularly preferred for use in certain aspects of the present methods are those encoding VMP-like and VMP-related polypeptides.

It is also contemplated that one may clone other additional genes or cDNAs that encode a VMP-like or VMP-related peptide, protein or polypeptide. The techniques for cloning DNA molecules, i.e., obtaining a specific coding sequence from a DNA library that is distinct from other portions of DNA, are well known in the art. This can be achieved by, for example, screening an appropriate DNA library which relates to the cloning of a Ws gene such as from the variable region of that gene. The screening procedure may be based on the hybridization of oligonucleotide probes, designed from a consideration of portions of the amino acid sequence of known DNA sequences encoding related *Borrelia* proteins. The operation of such screening protocols is well known to those of skill in the art and are described in detail in the scientific literature, for example, see Sambrook et al., 2001.

Techniques for introducing changes in nucleotide sequences that are designed to alter the functional properties of the encoded proteins or polypeptides are well known in the

TABLE 2

Codon Frequency in *Homo sapiens*

| Codon | $v^b$ | Total #$^a$ | Codon | $v^b$ | Total #$^a$ | Codon | $v^b$ | Total #$^a$ | Codon | $v^b$ | Total #$^a$ |
|---|---|---|---|---|---|---|---|---|---|---|---|
| UUU | 16.6 | 72711 | UCU | 14.0 | 62953 | UAU | 12.3 | 55039 | UGU | 9.5 | 42692 |
| UUC | 21.4 | 95962 | UCC | 17.7 | 79482 | UAC | 17.0 | 76480 | UGC | 12.8 | 57368 |
| UUA | 6.3 | 28202 | UCA | 10.7 | 48225 | UAA | 0.7 | 2955 | UGA | 1.2 | 5481 |
| UUG | 11.5 | 51496 | UCG | 4.4 | 19640 | UAG | 0.5 | 2181 | UGG | 13.5 | 59982 |
| CUU | 11.7 | 52401 | CCU | 16.7 | 74975 | CAU | 9.6 | 43193 | CGU | 4.6 | 20792 |
| CUC | 19.5 | 87696 | CCC | 20.0 | 89974 | CAC | 14.6 | 65533 | CGC | 11.0 | 49507 |
| CUA | 6.3 | 28474 | CCA | 16.2 | 72711 | CAA | 11.4 | 51146 | CGA | 5.9 | 26551 |
| CUG | 40.6 | 182139 | CCG | 6.9 | 30863 | CAG | 33.7 | 151070 | CGG | 11.3 | 50682 |
| AUU | 15.7 | 70652 | ACU | 12.8 | 57288 | AAU | 16.6 | 74401 | AGU | 11.1 | 49894 |
| AUC | 23.7 | 106390 | ACC | 21.1 | 94793 | AAC | 21.1 | 94725 | AGC | 19.1 | 85754 |
| AUA | 6.7 | 30139 | ACA | 14.7 | 66136 | AAA | 23.2 | 104221 | AGA | 10.8 | 48369 |
| AUG | 22.6 | 101326 | ACG | 6.7 | 30059 | AAG | 33.9 | 152179 | AGG | 10.9 | 48882 |
| GUU | 10.6 | 47805 | GCU | 18.7 | 83800 | GAU | 22.0 | 98712 | GCU | 11.2 | 50125 |
| GUC | 15.6 | 70189 | GCC | 29.2 | 130966 | GAC | 27.0 | 121005 | GGC | 24.0 | 107571 |
| GUA | 6.6 | 29659 | GCA | 15.3 | 68653 | GAA | 27.8 | 124852 | GGA | 16.9 | 75708 |
| GUG | 30.0 | 134750 | GCG | 7.5 | 33759 | GAG | 40.8 | 182943 | GGG | 16.7 | 74859 |

Coding GC 52.96%
1st letter GC 55.98%
2nd letter GC 42.29%
3rd letter GC 60.60%
$^a$Total 4489120
$^b$v = Frequency per 1000

The definition of a "VMP-like sequence" or "VMP-related gene" as used herein, is a gene that hybridizes, under relatively stringent hybridization conditions (see, e.g., Sambrook et al., 2001), to DNA sequences presently known to include related gene sequences.

art, e.g., U.S. Pat. No. 4,518,584, incorporated herein by reference, which techniques are also described in further detail herein. Such modifications include the deletion, insertion or substitution of bases, which may or may not result in changes in the amino acid sequence. Changes may be made to increase the activity of a protein, to increase its biological stability or half-life, to change its glycosylation pattern, and the like. All such modifications to the nucleotide sequences are encompassed by this invention.

I. Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 3

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG CGU |
| Serine | Ser | S | AGC | AGU | UCA | UCC | UCG UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

J. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 1 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

H. Expression of VMP-like Proteins

A particular aspect of this invention provides novel ways in which to utilize VMP-like DNA segments and recombinant vectors comprising vls DNA segments. As is well known to those of skill in the art, many such vectors are readily available, one particular detailed example of a suitable vector for expression in mammalian cells is that described in U.S. Pat. No. 5,168,050, incorporated herein by reference. However, there is no requirement that a highly purified vector be used, so long as the coding segment employed encodes a VMP-like protein and does not include any coding or regulatory sequences that would have an adverse effect on cells. Therefore, it will also be understood that useful nucleic acid sequences may include additional residues, such as additional non-coding sequences flanking either of the 5' or 3' portions of the coding including, for example, promoter regions, or may include various internal sequences, i.e., introns, which are known to occur within genes.

After identifying an appropriate VMP-encoding gene or DNA molecule, it may be inserted into any one of the many vectors currently known in the art, so that it will direct the expression and production of the VMP-like protein when incorporated into a host cell. In a recombinant expression vector, the coding portion of the DNA segment is positioned under the control of a promoter. The promoter may be in the form of the promoter which is naturally associated with a VMP-encoding gene, as may be obtained by isolating the 5' non-coding sequences located upstream of the coding segment, for example, using recombinant cloning and/or PCR™ technology, in connection with the compositions disclosed herein.

The use of recombinant promoters to achieve protein expression is generally known to those of skill in the art of molecular biology, for example, see Sambrook et al., (2001).

For the expression of VMP-like proteins, once a suitable (full-length if desired) clone or clones have been obtained, whether they be cDNA based or genomic, one may proceed to prepare an expression system for the recombinant preparation of VMP-like proteins. The engineering of DNA segment(s) for expression in a prokaryotic or eukaryotic system may be performed by techniques generally known to those of skill in recombinant expression. It is believed that virtually any expression system may be employed in the expression of VMP-like proteins.

VMP-like proteins may be successfully expressed in eukaryotic expression systems, however, it is also envisioned that bacterial expression systems may be preferred for the preparation of VMP-like proteins for all purposes. The DNA or cDNA encoding VMP-like proteins may be separately expressed in bacterial systems, with the encoded proteins being expressed as fusions with beta-galactosidase, ubiquitin, Schistosoma japonicum glutathione S-transferase, green fluorescent protein, polyhistidine and the like. It is believed that bacterial expression will ultimately have advantages over eukaryotic expression in terms of ease of use and quantity of materials obtained thereby.

It is proposed that transformation of host cells with DNA segments encoding VMP-like proteins will provide a convenient means for obtaining VMP-like peptides. Both cDNA and genomic sequences are suitable for eukaryotic expression, as the host cell will, of course, process the genomic transcripts to yield functional mRNA for translation into protein.

It is similarly believed that almost any eukaryotic expression system may be utilized for the expression of VMP-like proteins, e.g., baculovirus-based, glutamine synthase-based or dihydrofolate reductase-based systems could be employed. However, in preferred embodiments, it is contemplated that plasmid vectors incorporating an origin of replication and an efficient eukaryotic promoter, as exemplified by the eukaryotic vectors of the pCMV series, such as pCMV5, will be of most use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes VMP-like protein, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

Translational enhancers may also be incorporated as part of the vector DNA. Thus the DNA constructs of the present invention should also preferable contain one or more 5' non-translated leader sequences which may serve to enhance expression of the gene products from the resulting mRNA transcripts. Such sequences may be derived from the promoter selected to express the gene or can be specifically modified to increase translation of the RNA. Such regions may also be obtained from viral RNAs, from suitable eukaryotic genes, or from a synthetic gene sequence.

Such "enhancer" sequences may be desirable to increase or alter the transcription of translational efficiency of the resultant mRNA. The present invention is not limited to constructs where the enhancer is derived from the native 5'-nontranslated promoter sequence, but may also include non-translated leader sequences derived from other non-related promoters such as other enhancer transcriptional activators or genes.

It is contemplated that virtually any of the commonly employed host cells can be used in connection with the expression of VMPs in accordance herewith. Examples include cell lines typically employed for eukaryotic expression such as 239, AtT-20, HepG2, VERO, HeLa, CHO, WI38, BHK, COS-7, RIN and MDCK cell lines.

It is contemplated that VMP-like protein may be "overexpressed", i.e., expressed in increased levels relative to its natural expression in *Borrelia* cells, or even relative to the expression of other proteins in a recombinant host cell containing VMP-encoding DNA segments. Such overexpression may be assessed by a variety of methods, including radiolabeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural VMP-producing animal cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding a VMP-like peptide has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

It will be understood that recombinant VMP-like proteins may differ from naturally produced VMP-like proteins in certain ways. In particular, the degree of post-translational modifications, such as, for example, lipidation, glycosylation and phosphorylation may be different between the recombinant VMP-like and the VMP-like polypeptide purified from a natural source, such as *Borrelia.*

After identifying an appropriate DNA molecule by any or a combination of means as described above, the DNA may then be inserted into any one of the many vectors currently known in the art and transferred to a prokaryotic or eukaryotic host cell where it will direct the expression and production of the so-called "recombinant" version of the protein. The recombinant host cell may be selected from a group consisting of *S. mutans, E. coli, S. cerevisiae. Bacillus* sp., *Lactococci* sp., *Enterococci* sp., or *Salmonella* sp. In certain preferred embodiments, the recombinant host cell will have a recA phenotype.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. The use of these constitutive promoters will ensure a high, constant level of expression of the introduced genes. The level of expression from the introduced genes of interest can vary in different clones, probably as a function of the site of insertion of the recombinant gene in the chromosomal DNA. Thus, the level of expression of a particular recombinant gene can be chosen by evaluating different clones derived from each transfection study; once that line is chosen, the constitutive promoter ensures that the desired level of expression is permanently maintained. It may also be possible to use promoters that are subject to regulation, such as those regulated by the presence of lactose analog or by the expression of bacteriophage T7 DNA polymerase.

Technology for introduction of DNA into cells is well-known to those of skill in the art. Five general methods for delivering a gene into cells have been described: (1) chemical methods; (2) physical methods such as microinjection, electroporation and the gene gun; (3) viral vectors; (4) receptor-mediated mechanisms; and (5) direct injection of purified DNA into human or animals.

G. Liposomes and Nanocapsules

The formation and use of liposomes is generally known to those of skill in the art (see for example, Couvreur et al., *Pharm Res.:* 8(9), 1079-86, 1991, which describes the use of liposomes and nanocapsules in the targeted antibiotic therapy of intracellular bacterial infections and diseases). Recently, liposomes were developed with improved serum stability and circulation half-times of substances, including DNA (Gabizon and Papahadjopoulos, *Proc Natl Acad Sci USA.,* 85(18): 6949-53, 1988; Allen and Chonn, *FEBS Lett.,* 223(1): 42-6, 1987). The following is a brief description of this and other DNA delivery modes.

Nanocapsules can generally entrap compounds in a stable and reproducible way (Henry-Michelland et al., *Int J Pharm.,* 35: 121-127, 1987). To avoid side effects due to intracellular polymeric overloading, such ultrafine particles (sized around 0.1 mm) should be designed using polymers able to be degraded in vivo. Biodegradable polyalkyl-cyanoacrylate nanoparticles that meet these requirements are contemplated for use in the present invention, and such particles may be are easily made, as described (Couvreur, *J. Pharm Belg.,* 39(4): 249-54, 1984; Couvreur et al., *Bull Mem Acad R Med Belg.,* 143(7-9): 378-88, 1988).

Liposomes are formed from phospholipids that are dispersed in an aqueous medium and spontaneously form multilamellar concentric bilayer vesicles (also termed multilamellar vesicles (MLVs). MLVs generally have diameters ranging from 25 μm to 4 μm. Sonication of MLVs results in the formation of small unilamellar vesicles (SUVs) with diameters in the range of 200 to 500 Å, containing an aqueous solution in the core.

The following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

L. Pharmaceutical Compositions

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Experimental Procedures

Bacterial Strains

*B. garinii* Ip90 was initially isolated from ticks collected in eastern Russia (Kriuchechnikov et al., 1988). *B. afzelii* ACAI was cultured from a patient in Sweden with acrodermatitis chronica atrophicans (Asbrink et al., 1984). Both strains were graciously provided by Dr. Alan Barbour, University of California at Irvine School of Medicine, and had been passed through C3H/HeN mice to assure infectivity. Strains were passaged in vitro fewer than 5 times following mouse infection.

DNA Cloning and Sequencing

Plasmid DNA was purified from the *Borrelia* strains as described previously (Purser and Norris, 2000). λ DASH II libraries of plasmid DNA fragments were prepared as described by Zhang et al. (Zhang et al., 1997), with minor modifications. Thirty micrograms of plasmid DNA was treated with 30 units of mung bean nuclease at 30° C. for 30 min to hydrolyze hairpin loops in telomeres, and an EcoRI linker (5'-CCGGAATTCCGG-3'; SEQ. ID. NO:107) was then ligated to the treated plasmid DNA using $T_4$ DNA ligase at 15° C. overnight. This preparation was then digested to completion with EcoRI, and the resulting DNA fragments were fractionated by agarose gel electrophoresis. EcoRI-treated DNA fragments ranging in size from 8 kb to 25 kb were used to create libraries in EcoRI pre-treated λ DASH II vector arms as described in the manufacturer's instructions (Stratagene, La Jolla, Calif., USA). Recombinant phages were screened by plaque hybridization using *B. burgdorferi* B31 vls silent cassette clone pJRZ53 (Zhang et al., 1997) as probe; hybridization with pJRZ53 was confirmed by secondary phage plaque screening as well as Southern blot hybridization. Selected phage clones were expanded, phage were purified, and DNA was prepared by standard techniques. The λ phage clones Ip90.1A1 and ACAI.2A1, each containing a 15 kb *borrelia* DNA insert, were selected for analysis.

To sequence the DNA insert of Ip90.1A1, the phage DNA was digested with EcoRI and HindIII and a 6 kb EcoRI/HindIII fragment containing vls-like sequence was then cloned into pBluescript II SK(−) (Stratagene). The plasmid DNA of the pBluescript clone was digested with EcoRI and HindIII, and the 6 kb DNA fragment was isolated by agarose gel electrophoresis followed by electroelution, partially digested with DNase I and cloned into EcoRV treated pBluescript II SK (−) to create random DNase I library as described previously (Zhang et al., 1997). Clones with insert DNA ranging in size from 500 to 1,000 bp from the DNase I library were selected for sequencing using primers specific for the vector T7 and T3 sequences. To facilitate sequencing of the ACAI.2A1 clone, the phage DNA was treated with XbaI and EcoRI, and one 8 kb EcoRI/XbaI fragment containing vls-like sequence was isolated from an agarose gel. This 8 kb EcoRI/XbaI fragment was digested separately with RsaI and PstI and then cloned into pBluescript II SK (−) to generate RsaI and PstI libraries. Clones from both libraries were selected for sequencing at the Department of Microbiology and Molecular Genetics Sequencing Facility. Primer walking and PCR (see below) were utilized as needed to fill gaps, establish clone order, and confirm and extend the sequences. DNA sequences were assembled using DNASTAR software (DNASTAR, Inc., Madison, Wis.).

Southern Hybridization

Fifty nanograms of DNA was digested with the indicated restriction enzymes, subjected to agarose electrophoresis in 1×TAE buffer at 100V for 2 hr, and transferred to Amersham Hybond N+ membranes using standard alkaline transfer techniques. Hybridization with pJRZ53 as probe was performed by enhanced chemiluminescence techniques following the manufacturer's protocol (Amersham Gene Images, Amersham, Piscataway, N.J., USA).

PCR and RT-PCR

PCR was utilized to amplify vls sequences beyond the end of the 8 kb EcoRI/XbaI fragment from ACAI, and thereby extend the sequence beyond the cloned region. The specific primer 4540 (5'-CCA GCA AAC AAC TTC CCC GCC-3'—SEQ ID NO:21), based on a variable region, and the nonspecific primer 4548 (5'-ATC CTT AAA CTC CGC CCC ATC ATC-3'—SEQ ID NO:22), based on an invariant 5' region of the vls silent cassettes of ACAI, were used as primers. Primer 4545 (5'-GAG TGC TGT GGA GAG TGC TGT TGA TGA G-3'—SEQ ID NO:23), based on the direct repeat sequence, was also used in some PCR studies. *B. afzelii* ACAI plasmid DNA was used as the template in these reactions.

RT-PCR was used to detect transcription of vlsE in *B. garinii* Ip90 and *B. afzelii* ACAI. Forward primer 4587 (5'-GGG GAT AAA GGG GAT TGT TGAT GCT GC-3'—SEQ ID NO:24) and reverse primer 4588 (5'-GCA AAC TGC CCA TCC TTA GCC ATT CC-3'—SEQ ID NO:25) were designed based on the invariable regions of vls silent cassettes of Ip90; the forward primer 4470 (5'-AAG GGG ATT GCG AAG GGG ATA AAG G-3'—SEQ ID NO:26) and reverse primer 4471 (5'-TTA GCA GCA AACTTT CCA TCC TTA GCC-3'—SEQ ID NO:27) were used for ACAI. Total RNA was isolated from late log-phase cultures of Ip90 and ACAI using an RNA purification kit (Amersham). RT-PCR was carried out using the Promega Access RT-PCR kit according to manufacturer's instructions. Briefly, reverse transcription was carried out for 50 min at 48° C. followed by an initial denaturation at 94° C. for 3 min, and 30 cycles consisting of denaturation at 94° C. for 30 sec, annealing at 68° C. for 1.5 min, and extension at 68° C. for 1.5 min.

Cloning and Sequencing vlsE RT-PCR Products

As mentioned above, both *B. afzelii* ACAI and *B. garinii* Ip90 used in these studies were first cloned by colony formation and then passaged through mice. To determine whether vlsE sequence variation was present following mouse infection, *B. afzelii* ACAI was grown from a frozen stock and cloned by colony formation on BSKY plates (Dever et al., 1992). RT-PCR of individual clones was performed as described in a previous section, and cDNA was ligated into pCR 2.1 TOPO TA cloning vector (Invitrogen, Carlsbad, Calif., USA). Each vlsE variant was sequenced with the M13 forward and reverse primers. *B. garinii* Ip90 RNA was isolated from an uncloned population following mouse infection, and thus contained a mixture of variants. RT-PCR and cDNA cloning were performed using the method described for ACAI. Sequences were aligned with the multiple alignment program (Smith et al., 1996). The alignment output was formatted using Boxshade 3.21 (Hofmann and Baron, 1996).

Accession Numbers

The sequence of the vls silent cassette region of *B. afzelii* ACAI is provided at the United States National Center for Biomedical Information with GenBank accession number AY100628 (SEQ ID: NO:57). The *B. garinii* Ip90 silent cassette region is listed as AY100633 (SEQ ID NO:28). The RT-PCR product sequences obtained are listed as AY100629-AY100632 (SEQ ID: NOS:5-12) and AY100634-AY100637 (SEQ ID NOS:13-20) for ACAI and Ip90, respectively.

Example 2

Identification of vls Loci in *B. garinii* Ip90 and *B. afzelii* ACAI

Hybridization with the *B. burgdorferi* B31 vls silent cassette sequence in recombinant plasmid pJRZ53 was used as a means of identifying the plasmids and DNA fragments containing vls sequences in *B. garinii* Ip90 and *B. afzelii* ACAI. The pJRZ53 probe hybridized exclusively to plasmids with an approximate size of 28 kb in both ACAI and Ip90. Following treatment of plasmid preparations with restriction enzymes, the major hybridizing DNA segments were identified as a 15 kb EcoRI fragment of ACAI DNA and a 20 kb EcoRI fragment of Ip90 plasmid DNA. Libraries of plasmid DNA EcoRI fragments were prepared in Lambda Dash II using a technique that permits the cloning of telomere-containing as well as internal fragments through treatment of the hairpin loop telomeres with mung bean nuclease followed by ligation with EcoRI linkers (Zhang et al., 1997). The phage libraries were screened by hybridization with pJRZ53, and clones Ip90.1A1 and ACAI.2A1, each containing 15 kb of insert DNA, were used for further analysis.

Example 3

Organization of vls Silent Cassette Loci

The overall organization of the vls silent cassette loci of Ip90 and ACAI is shown in FIG. 1. As was the case in *B. burgdorferi* B31, the silent cassette loci in each strain was composed of a contiguous array of multiple cassettes. The loci in Ip90 and ACAI consisted largely of contiguous, uninterrupted open reading frames, with one frameshift present at the 3' end of cassette 9 in ACAI. The B31 vls silent cassette locus contained one stop codon and two frame shifts (Zhang et al., 1997).

Example 4

Structure of the Ip90 vls Silent Cassette Locus

In Ip90, the vls array consisted of 11 regions with homology to the vls cassettes of B31 (FIG. 1A). With the exception of the junctions at vls3/4 and vls6/7, the 11 vls silent cassettes are flanked by 18 bp direct repeat sequences in the 6 kb region. However, several of these cassettes (vls1, vls4, vls6, and vls11) were truncated (189 to 288 bp in length) relative to the other, full-length cassettes ranging in size from 573 to 594 bp. By comparison with the vls expression cassette of B31, cassette 1 is truncated at the 3' region, containing only 92 amino acid codons; cassette 4 lacks 125 codons in its 5' region; cassette 6 contains only 89 codons and is missing most of the 3' region; and cassette 11 has 86 codons, but is missing the 3' region. A portion of the silent cassette locus from the last 3 bp of cassette 5 to the first 165 bp of cassette 8 is identical to the P7-1 clone previously characterized by Liang et al. (Liang and Philipp, 1999) (FIG. 1A). The 3' end of the Ip90 silent cassette locus possessed a truncated pseudogene of a conserved hypothetical protein belonging to gene family 144 of *B. burgdorferi* B31(TIGR, 2002).

The 5' end of the locus also contained a region homologous to the 5', unique (non-cassette) portion of B31 expression site, vlsE (FIG. 1A). However, this gene segment is lacking a promoter region and the first 59 codons of vlsE, and also contains segments that are non-homologous to B31 vlsE. Therefore, this 'vlsE-like' sequence appears to be a pseudogene, although it is in frame with the cassette 1 of the vls silent cassette array and could conceivably encode a vlsE-like product. It is of interest to note that vlsE of *B. burgdorferi* B31 is located close to the telomere of lp28-1, but is oriented in the opposite direction (i.e. is transcribed toward the telomere) relative to the vlsE-like sequence of Ip90. In addition, the reading frame of the vls silent cassette array in Ip90 runs away from, rather than toward (as is the case with the silent cassettes in B31), the nearest telomere (FIG. 1) (Zhang et al., 1997). Therefore, the B31 and Ip90 versions of the silent cassette loci have likely undergone large-scale rearrangements during evolution from a common ancestral organism, and it is unlikely that the Ip90 vlsE-like pseudogene evolved directly from a functional telomeric copy of vlsE. Based on other evidence, we believe that a functional vlsE gene is located elsewhere on the 28 kb plasmid of Ip90 (see below).

Portions of several vls silent cassettes from *Borrelia garinii* strain A87S were published previously (Wang et al., 2001). Each putative silent cassette in the longest available A87S sequence (GenBank Accession No. AF274070) was compared to its corresponding cassette among the Ip90 silent cassettes. The A87S sequence shared only 63 to 68% nucleotide identity to Ip90 sequences, and amino acid similarity ranged from 51 to 57%. An amino acid alignment between the A87S and Ip90 silent cassettes reveals that the heterogeneity exists largely within invariable region 1 (IR1), found upstream of VR-I (data not shown). There are also considerable differences in IR4 and IR6, but to a lesser extent when compared to IR1. The sequence differences between the vls silent cassettes sequences of Ip90 and A87S indicates that a considerable degree of heterogeneity exists among vls sequences within this species, as also appears to be the case with *Borrelia burgdorferi* strains.

An unusual feature of the Ip90 telomere region upstream of the vls cassettes is the presence of a set of 6 complete and 1 partial copies of a 41 bp direct repeat sequence. The telomere itself was identified by its location in the lambda clone insert next to the EcoRI linker used to clone mung bean nuclease-treated telomere regions. Because mung bean nuclease potentially could remove terminal nucleotides as well as disrupting the hairpin loop 5'-3' bond, it is not known whether this sequence represents the absolute end of the telomere sequence. The telomeric repeat sequences (TRS) begin 52 bp from the end of the telomere sequence, and are present as six 41-bp repeats (TRS-A through TRS-F) followed by a 32-bp truncated version of the 41-bp sequence (TRS-G) in a contiguous array. These direct repeats differ at only one position in TRS-B, and are otherwise identical. The telomeric direct repeat has no significant homology with vls sequences or any other *borrelia* sequence reported previously. Although the direct repeats obviously arose through duplication events, their origin and significance are unknown at this time.

Example 5

Structure of the ACAI vls Silent Cassette Locus

Figure 1B:
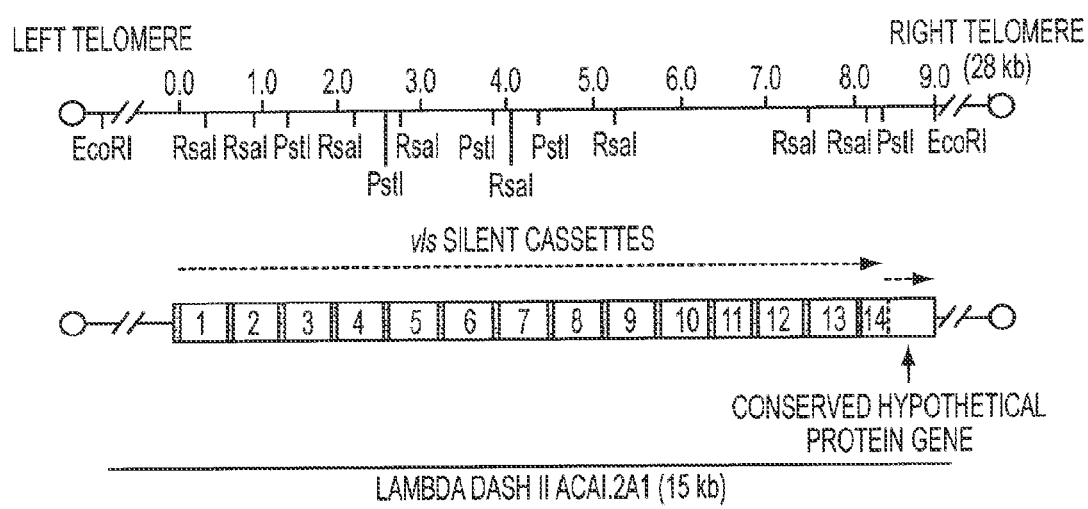

The overall arrangement of the *B. afzelii* ACAI vls silent cassette locus is depicted in FIG. 1B. Unlike Ip90 and B31, the ACAI vls locus was located on an internal EcoRI fragment of a 28-kb linear plasmid, and its location relative to the plasmid telomeres is not known. The ACAI vls locus contains 13 complete and 1 partial silent cassettes and each cassette is also flanked by an 18 bp direct repeat sequence. Twelve of the cassettes appear to represent 'full-length' sequences (ranging from 591 to 630 bp in length), whereas cassette 11 contains an internal deletion and cassette 14 has an internal deletion and a short, 3' truncation relative to the other cassette sequences (FIG. 1B). The 3' end of the silent cassette locus is demarcated by a complete copy of a conserved hypothetical protein gene belonging to gene family 57 of *B. burgdorferi* B31 (TIGR, 2002). We were unable to obtain additional sequence 5' of cassette 1, and it is possible that additional vls sequences are localized upstream of the region we have characterized thus far.

Example 6

Direct Repeats in the Silent Cassette Loci

In *B. burgdorferi* B31, both the central cassette of vlsE and the homologous vls silent cassettes are flanked by a 17 bp direct repeat sequence (5 '-TGAGGGGGCTATTAAGG-3' (SEQ ID NO:106)). This sequence is generally well-conserved in the vlsE expression site and the silent cassettes; it is absent from the 5'-truncated cassette 1, and only 10 of 17 nucleotides are present at the junction between vls9 and vls10 (Zhang et al., 1997). Based on the location and high degree of conservation of the 17 bp direct repeat, it was hypothesized previously that these sequences may play an important role in the vls gene conversion process. However, the 17 bp sequence is not highly conserved in the *B. garinii* Ip90 and *B. afzelii* ACAI vls silent cassette sequences (data not shown). A comparison of 17 bp consensus sequences from Ip90 and ACAI to the B31 17 bp sequence shows that the Ip90 and ACAI sequences are more similar to each other than to the B31 sequence. Nevertheless, the higher degree of variability in the Ip90 and ACAI 17 bp sequences compared to the B31 sequence suggests that the 17 bp sequence is not as important in the gene conversion process as previously thought (Zhang et al., 1997).

Example 7

Similarity of Vls Silent Cassette Loci

Figure 2A:
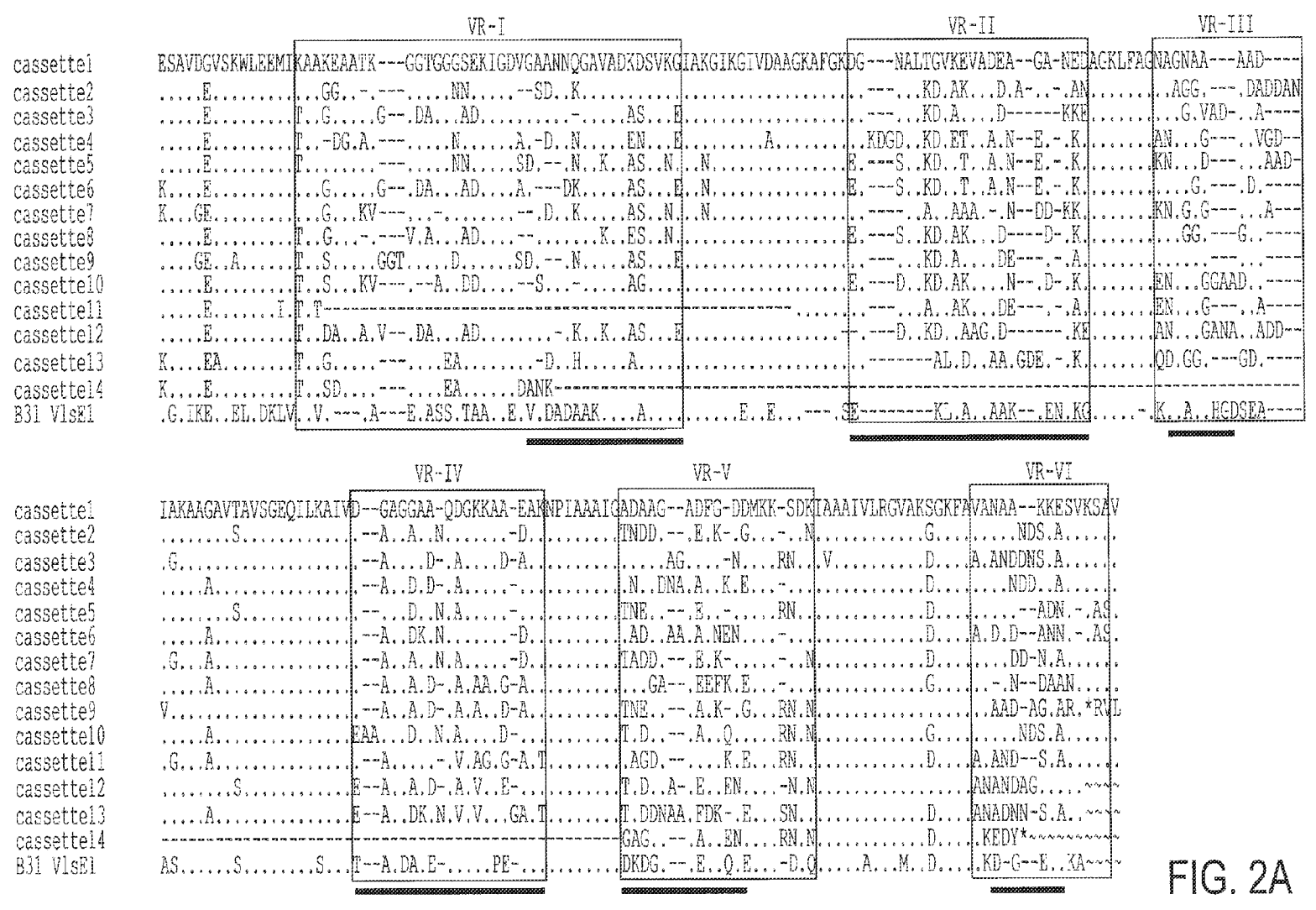
Figure 2B:
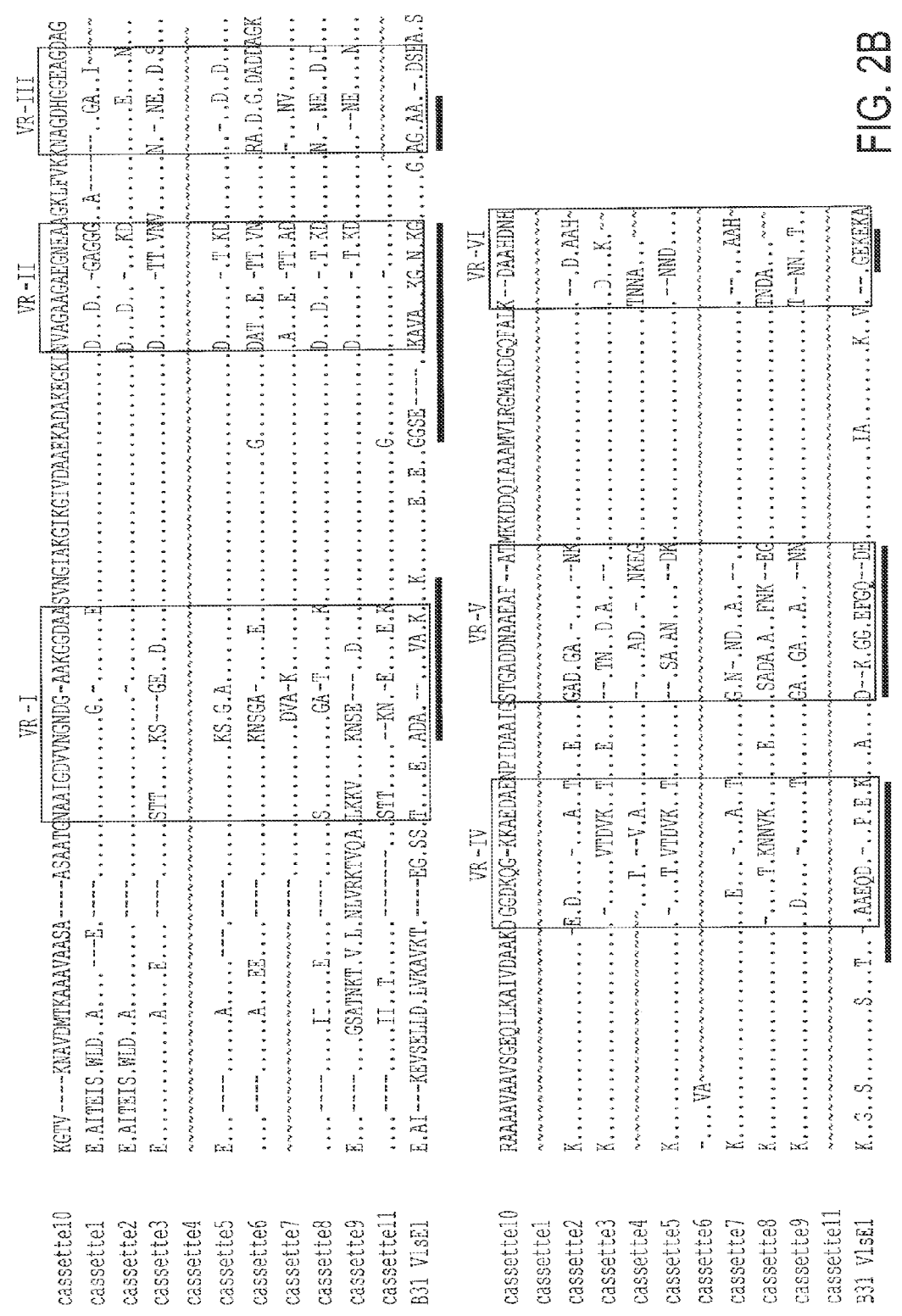

Alignment of the vls cassette sequences from Ip90, ACAI, and B31 indicates a high degree of sequence conservation both within and between each strain (FIG. 2). The Ip90 cassettes share 90 to 97% nucleotide sequence identity with one another, whereas the ACAI silent cassettes have from 84 to 91% nucleotide sequence identity (data not shown). The Ip90 vls silent cassettes are also highly homologous with *B. burgdorferi* vls sequences; for example, sequence identities with the B31 allele vlsE1 (Zhang et al., 1997) range from 64% to 73% on the nucleotide level and from 53% to 62% in predicted amino acid sequence (FIG. 2A). The identities between the ACAI vls silent cassettes and B31 vlsE1 likewise range from 65% to 73% on the nucleotide level and from 50% to 65% in predicted amino acid sequence (FIG. 2B). Each complete silent cassette of Ip90 and ACAI contains six variable regions interspersed by six invariable regions similar to those found in the vls sequences of B31 (FIG. 2).

SEQ ID NO:28 is the *B. garinii* Ip90 vls locus silent cassette nucleic acid sequence. SEQ ID NO:30 is a translation of an upstream open reading frame of SEQ ID NO:28, which is contiguous with the open reading frame of the silent cassettes of the *B. garinii* Ip90 vls locus. SEQ ID NO:32 is a translation of a vlsE-like sequence of SEQ ID NO:28. SEQ ID NOS:33-54 are nucleotide and amino acid sequences of silent cassette Nos. 1-11 of the *B. garinii* Ip90 vls locus as set forth in FIG. 2B. SEQ ID NO:55 and 56 are the nucleotide and amino acid sequences of a truncated pseudogene in the *B. garinii* lp90 vls locus with 85% similarity to amino acids 70-140 of the *B. burgdorferi* B31 ORF-10 predicted product, GenBank Accession No. AA 34908.

SEQ ID NO:57 is the *B. afzelii* ACAI vls silent cassette locus nucleic acid sequence. SEQ ID NOS:58-85 are the nucleotide and amino acid sequences of silent cassette Nos. 1-14 of the *B. afzelii* ACAI silent cassette locus as set forth in FIG. 2A. SEQ ID NOS:86 and 87 are the nucleotide and amino acid sequences of a portion of the *B. afzelii* ACAI vls silent cassette locus which encodes a member of protein family PF02414, a conserved hypothetical protein family thought to be involved in *Borrelia* plasmid partitions of replication.

Example 8

Transcription of vlsE of *B. garinii* Ip90 and *B. afzelii* ACAI

Figure 3:
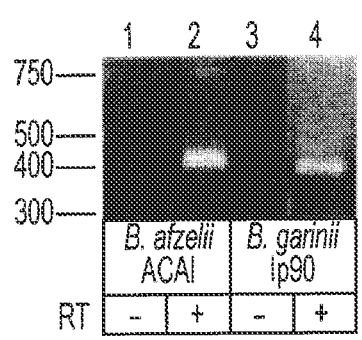
FIG. 3. RT-PCR of vlsE sequences, using RNA from B. afzelii ACAI (lanes 1 and 2) and B. garinii Ip90 (lanes 3 and 4) as template. Lanes 2 and 4, with reverse transcriptase; lanes 1 and 3, controls without reverse transcriptase. DNA marker sizes (bp) are indicated on the left.

We have thus far been unsuccessful in cloning a complete vlsE expression site from either Ip90 or ACAI using a variety of approaches (data not shown). To determine whether vls expression sites are present in Ip90 and ACAI, RT-PCR was carried out using total RNA from in vitro cultured *B. garinii* Ip90 and *B. afzelii* ACAI. Primers corresponding to invariant regions in the vls silent cassette regions of each organism were utilized. We observed a positive RT-PCR result in ethidium bromide-stained agarose gels for both *B. garinii* Ip90 and *B. afzelii* ACAI, but no products were observed if reverse transcriptase was omitted in the RT reaction (FIG. 3). The RT-PCR products containing Ws-like sequence were confirmed by sequencing, confirming that both organisms have vls expression sites. In *B. burgdorferi* B31, vlsE is located only 160 bp from the vls silent cassette array (Hudson et al., 2001; Zhang et al., 1997). Based on our studies, the vls expression sites of ACAI and Ip90 do not appear to be located in close proximity to the vls silent cassettes.

Example 9

Sequence Analysis of vlsE Variants of *B. afzelii* ACAI and *B. garinii* Ip90

Both ACAI and Ip90 were passaged through mice prior to analysis. In previous studies with *B. burgdorferi* B31, extensive sequence variation due to apparent gene conversion events occurred within the vlsE cassette region during mouse infection (Zhang and Norris, 1998a, b). To determine whether similar sequence variation occurred in ACAI and Ip90, individual RT-PCR products from each mouse-passaged strain were cloned and sequenced.

An alignment of the predicted VlsE protein sequences of ACAI and Ip90 (FIG. 4) demonstrated that sequence variation occurred within each strain. Moreover, the changes observed were consistent with gene conversion involving segments of the silent cassettes, as had been seen previously with B31. As with B31, the sequence differences were predictably localized primarily within the variable regions.

Figure 4A:
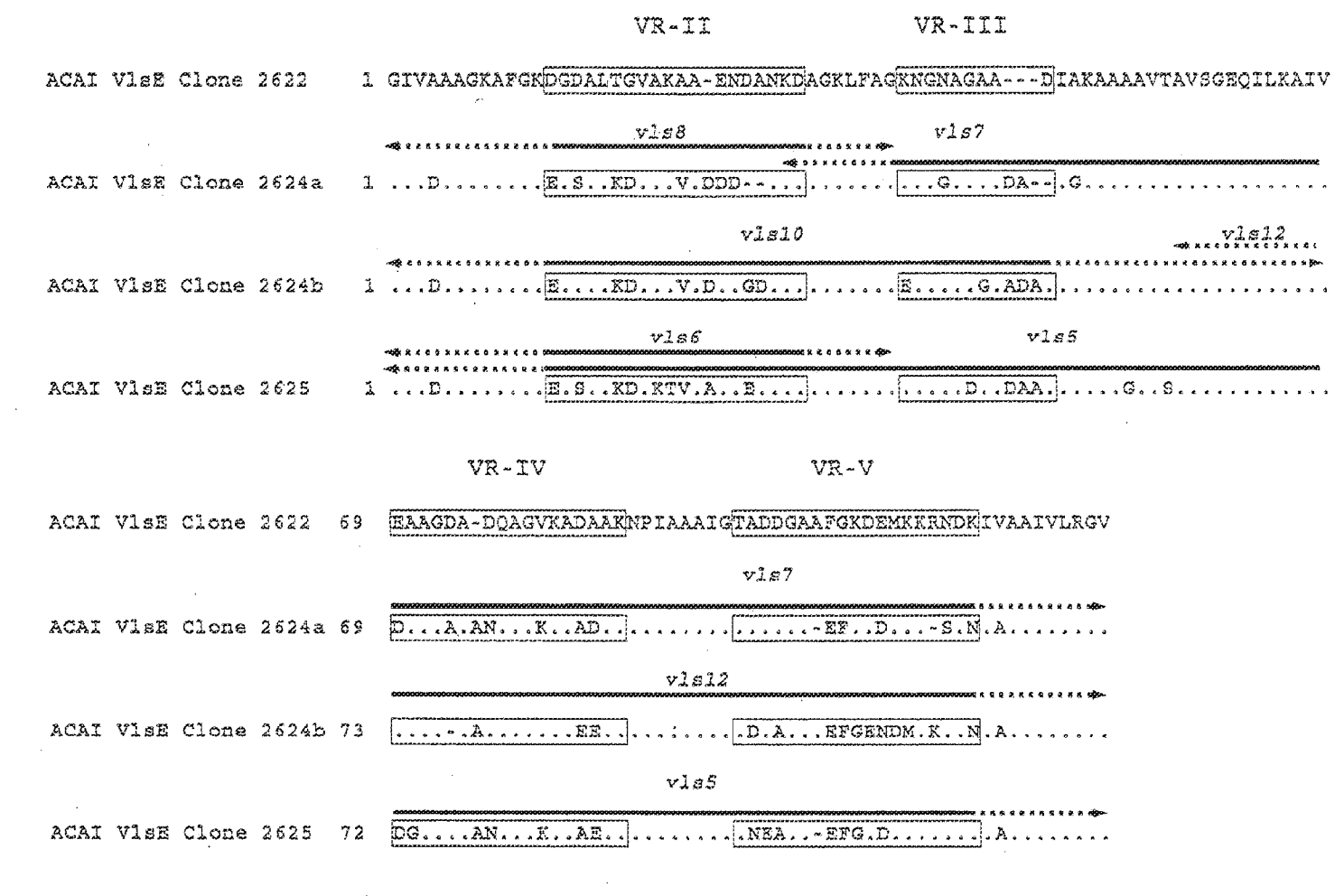

Using the sequences from the silent cassettes of each organism (FIG. 2), we determined the silent cassette sequences that were most likely involved in the gene conversion events within ACAI and Ip90 vlsE genes (FIG. 4). The theoretical minimum and maximum recombination events are indicated by solid and dotted lines, respectively. In FIG. 4A, silent cassette amino acid sequences matching regions of each variant are noted for all ACAI vlsE variants except clone 2622. The variation seen in clones 2624a and 2624b can be attributed to two silent cassettes each. In clone 2624a, vls8 matched the sequence found in a portion of variable region I (VR-I) and the entire sequence within VR-II, while vls7 matched the sequence found in VR-III, VR-IV, and VR-V. In clone 2624b, vls10 matched the sequence found in a portion of VR-I and the entire sequence within VR-II and VR-III, while vls12 matched the sequence found in VR-IV and VR-V. While both vls5 and vls6 match large portions of sequence in clone 2625, it seems more likely that vls5 was exclusively involved in the gene conversion events leading to the variation seen in clone 2625 since it contains sequence identity to VR-II, VR-III, VR-IV, and VR-V. It was difficult to ascertain which silent cassettes most likely contributed to the variation seen in clone 2622. Most silent cassettes matches spanned only a few residues in clone 2622. The nature of the sequence in clone 2622 suggests that it may be an artifactual PCR product.

Minimal recombination regions, indicated by solid lines in FIG. 4, were defined as the range of a vlsE RT-PCR product sequence that matched only a single silent cassette sequence. These commonly extend over several variable regions, as was also the case with *B. burgdorferi* B31 in previous studies (Zhang et al., 1997). In some cases, there are two or more silent cassettes that contain the same sequence within the same range. Therefore, it is only possible to predict the most likely silent cassette sequences involved (Indest et al., 2001). Maximum recombination regions commonly extend from a variable region and continue into the flanking invariant region of the corresponding matching silent cassette (FIG. 4). The extension of the maximum recombination region ends at the first position of sequence non-identity between the vlsE sequence of the clone and the given silent cassette. The degree of variation appears to be less than observed previously with *B. burgdorferi* B31, but an analysis of vlsE at different times during mammalian infection (Zhang and Norris, 1998b) is required to provide an accurate measure of the kinetics.

Figure 4B:
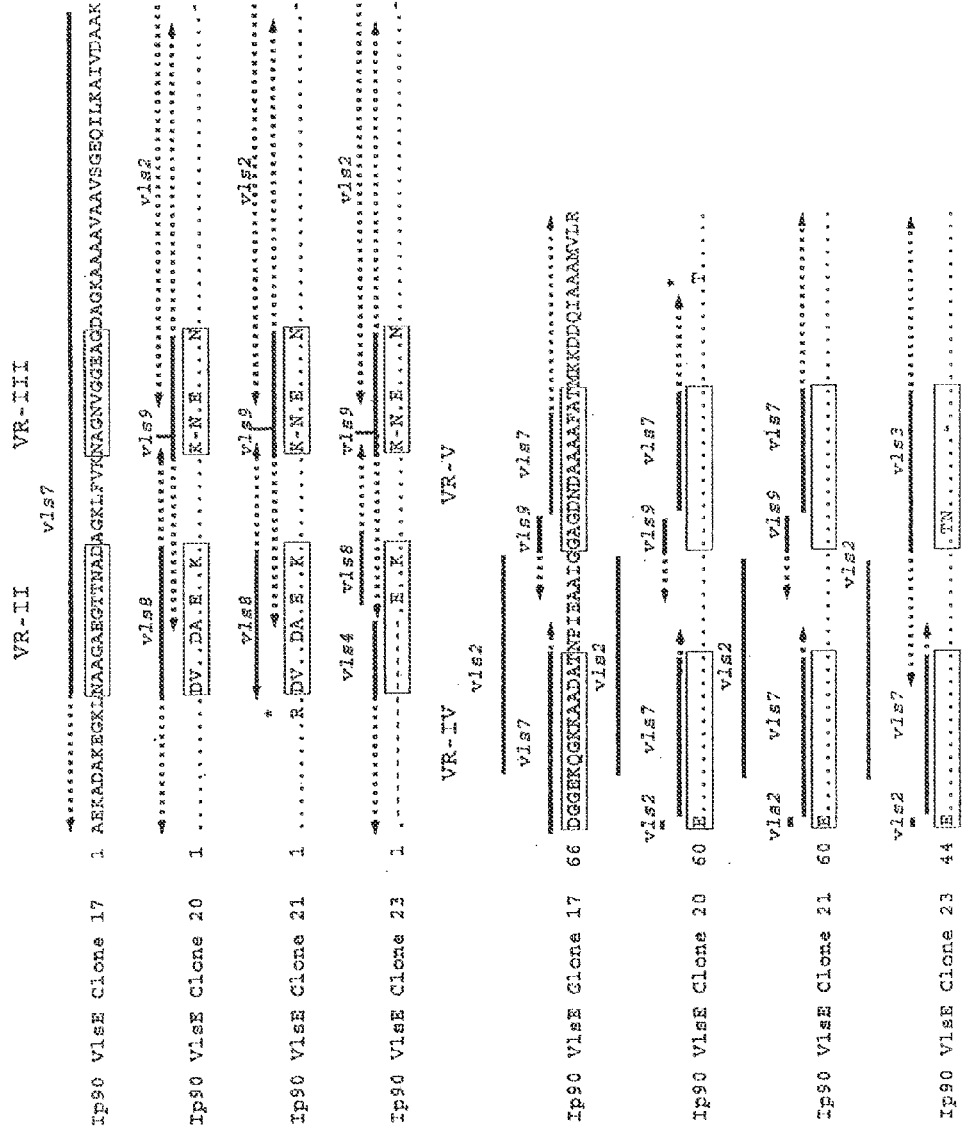
Figure 5:
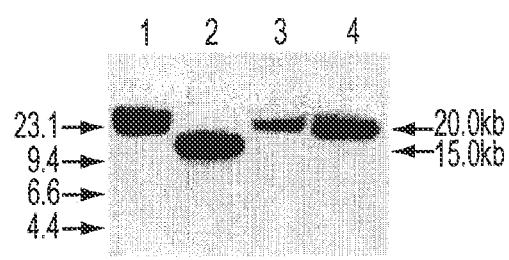
FIG. 5. Hybridization of plasmid DNA of B. afzelii ACAI and B. garinii Ip90 with pJRZ53 probe. Lane 1, ACAI plasmid DNA; lane 2, ACAI plasmid DNA digested with EcoRI; lane 3, Ip90 plasmid DNA; and lane 4, Ip90 plasmid DNA digested with EcoRI. The size of EcoRI fragments containing vls sequences are indicated by arrows at left.

There are two instances of what we believe to be point mutations in the Ip90 clones (FIG. 4B). The first instance lies two residues upstream of VR-II in clone 21, where there is an arginine residue not encoded in the silent cassettes. We believe a point mutation was responsible for changing the AAG codon in the silent cassettes to AGG in clone 21. The second example of a possible point mutation is the lone threonine after VR-V in clone 20. All of the silent cassette sequences possess a GCT codon at that position, while ACT is present in clone 20.

In conclusion, our results verify previous indications that both *B. garinii* and *B. afzelii* contain plasmid-encoded vls silent cassette loci similar to those of *B. burgdorferi*. In addition, RT-PCR results indicate that a vls product is expressed by both species, and that sequence variation occurs and hence may contribute to antigenic variation. Taken together, these and previous findings confirm that the Vls sequence variation system is a common feature of Lyme disease *borrelia*, and hence is likely to be important in the pathogenesis of these organisms.

Example 10

Reactivity of Sera from Human Lyme Disease Patients and Infected Mice with *Borrelia afzelii* Protein A recombinant DNA vector comprising a nucleotide sequence encoding the predicted amino acid sequence of the *B. afzelii* ACA-I vls cassette 13 (SEQ ID NOs:96 and 97) has been constructed. Briefly, DNA containing the coding sequence of the cassette region was amplified using a two-step polymerase chain reaction (PCR) method. During the first amplification, specific primers flanking the *B. afzelii* ACA-1 vls cassette (5'-CGGAATTCACTCGCCTTACTAT-TATC-3' (SEQ ID NO:98) and 5'-CGGGATCCGAGAGT-GCTGTTGATGAGGTT-3' (SEQ ID NO:99)) were used with *B. afzelii* ACA-I DNA as template to amplify a fragment containing the desired cassette. Then a second PCR was performed using primers specific for the cassette region itself (5'-CG GGATCCAAGAGTGCTGTGGATGAGGCTAGCAAG-3' (SEQ ID NO:100) and 5'-TT CTGCAGCACACTCGCCTTACTATTATCATTAGC-3' (SEQ ID NO:101)) and the purified product of the first reaction as the DNA template. The two primers contained BamHI and PstI sites, respectively (underlined); the PCR product was treated with these two enzymes and ligated into the expression vector pQE30 cut with the same two enzymes. The sequence of the insert was analyzed and found to be the correct sequence. The resulting recombinant plasmid, pBA-13-1 was used to transform *E. coli* cells, and expression was induced by incubation of a transformed *E. coli* clone to 1 mM isopropyl-β-D-thiogalactopyranoside (IPTG) for 3 hours. The *E. coli* cells were lysed by sonication and centrifuged to remove cellular debris. The recombinant, His6-tagged protein (VLS-BA13) was purified by liquid chromatography over a nickel affinity column, elution of bound protein with imidazole, and further purification using a heparin-Sepharose column. The purity of the protein was determined to be >90% by sodium-dodecyl sulfate polyacrylamide gel electrophoresis (SDS-PAGE), and the concentration determined by a Bradford protein assay.

Figure 6:
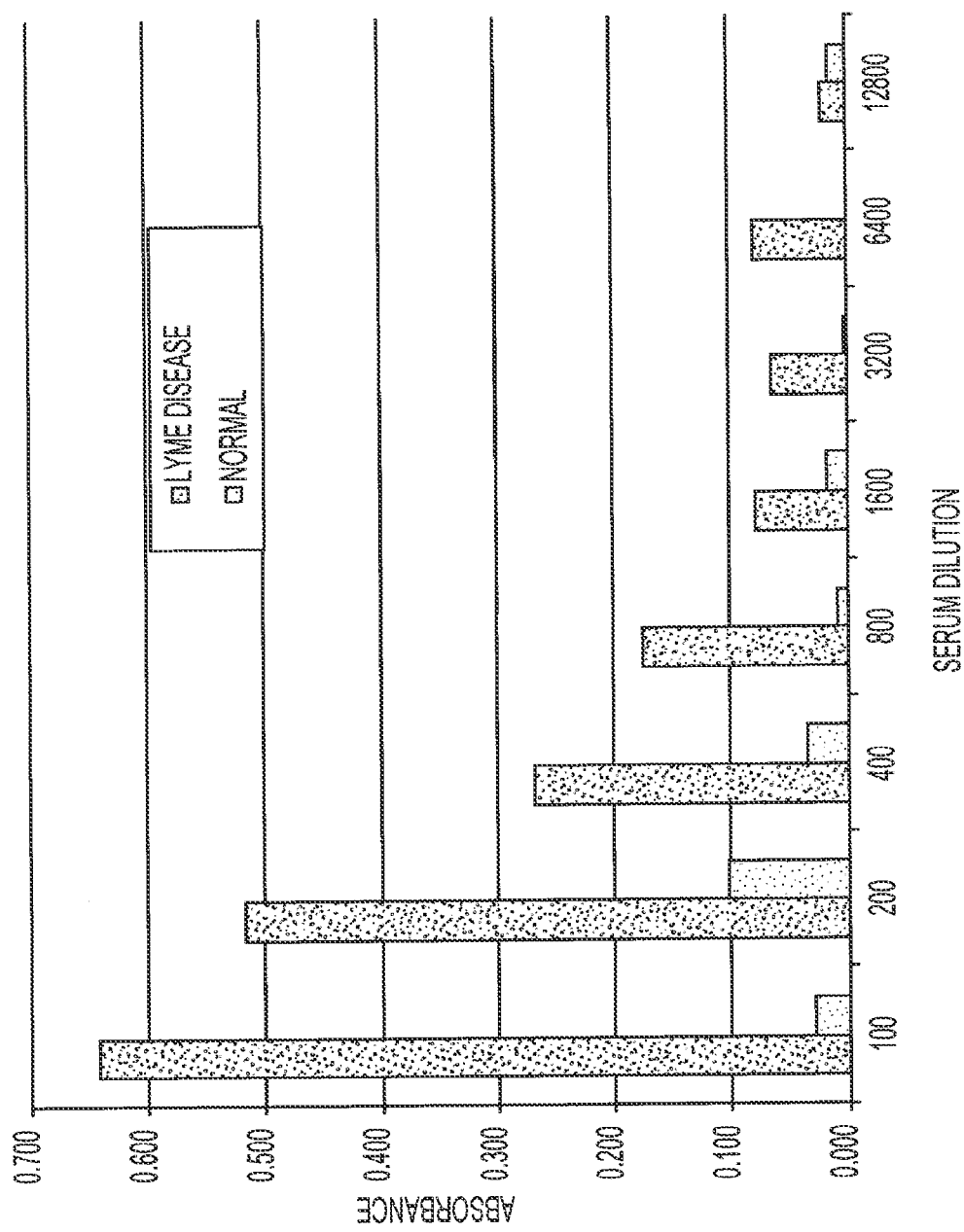
FIG. 6. Reactivity of human Lyme disease serum pool and a normal human serum pool with recombinant *Borrelia afzelii* Vls protein VLS-BA13.
Figure 7:
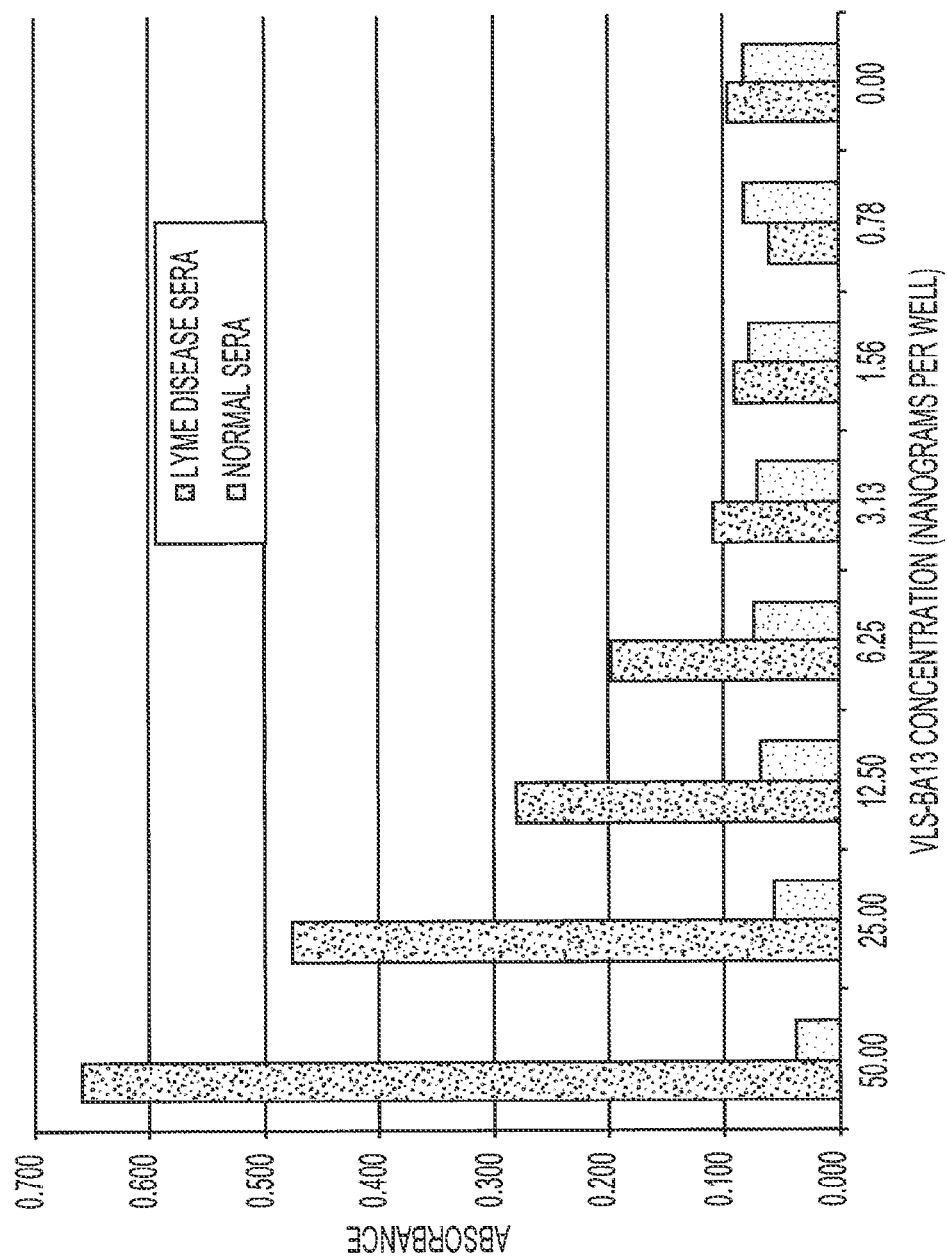
FIG. 7. Effect of VLS-BA13 protein concentration on enzyme immunoassay reactivity of serum pools from Lyme disease human subjects and normal human subjects.
Figure 8:
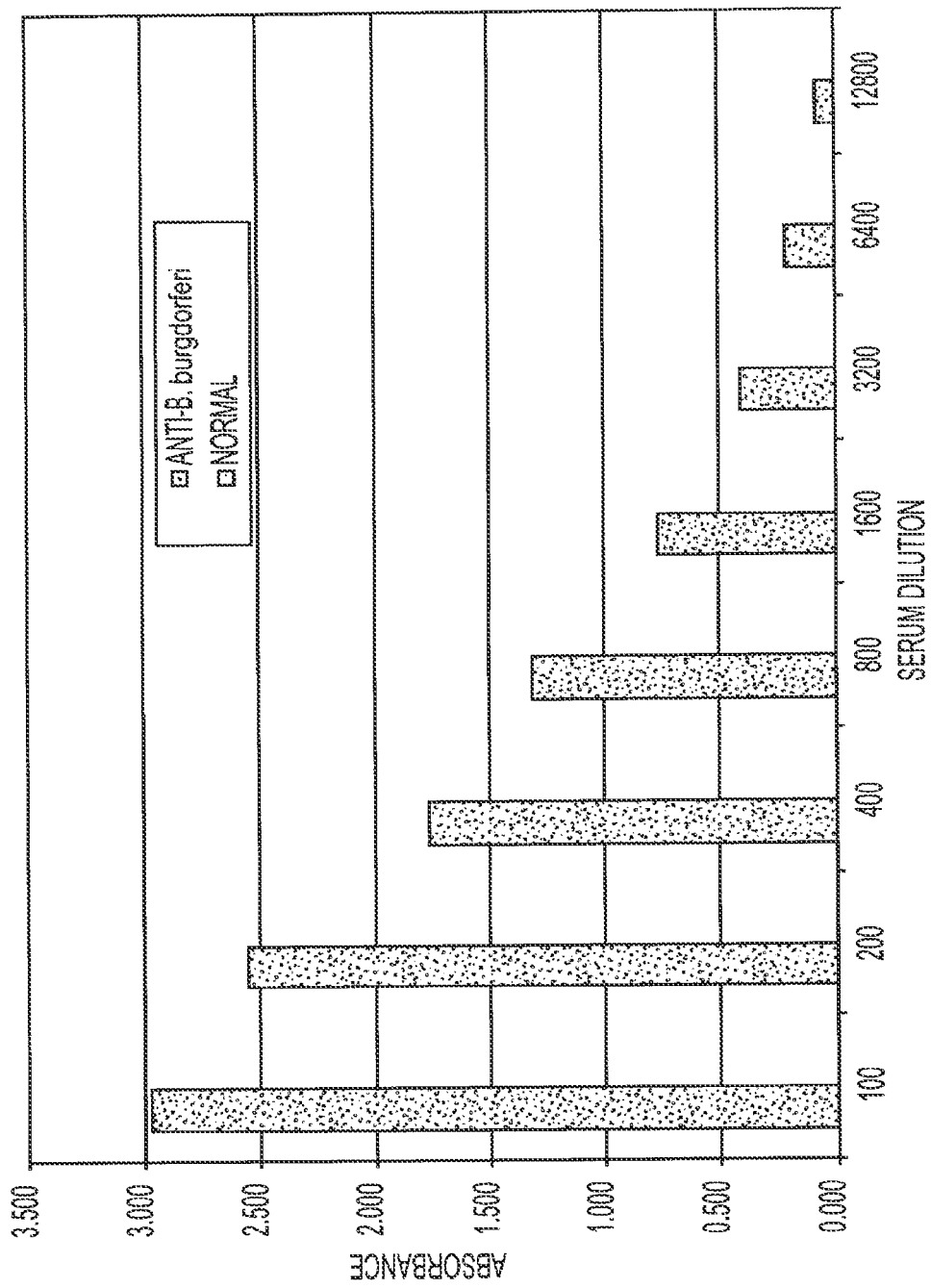
FIG. 8. Reactivity of mouse anti-*Borrelia burgdorferi* serum and normal mouse serum with recombinant *Borrelia afzelii* Vls protein VLS-BA13. The reactivity of normal mouse serum was below background levels.
Figure 9:
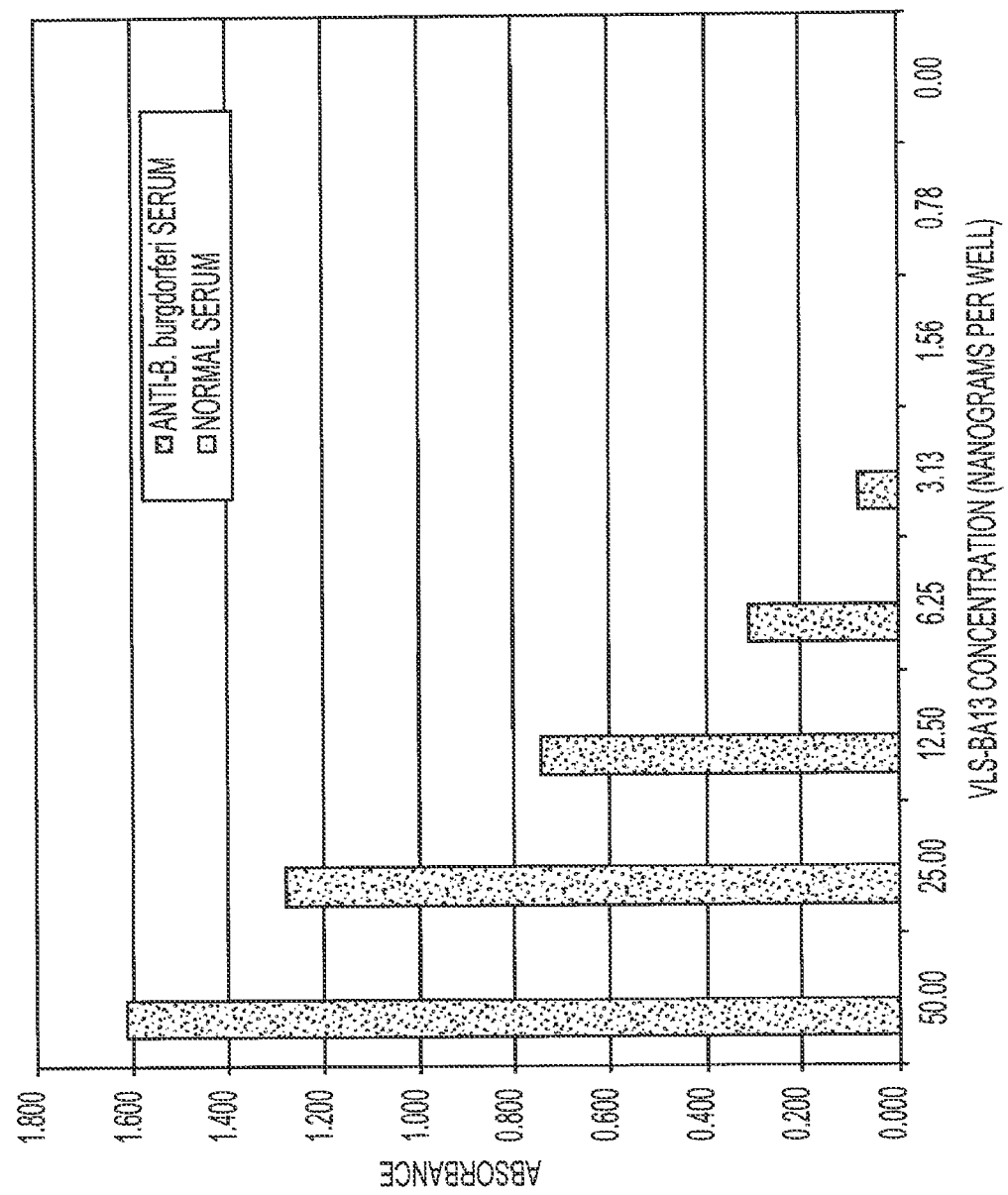
FIG. 9. Effect of VLS-BA13 protein concentration on enzyme immunoassay reactivity of mouse anti-*B. burgdorferi* antiserum and normal mouse serum. The reactivity of normal mouse serum was below background levels.

The purified recombinant protein VLS-BA13 was tested for reactivity with antibodies from humans using a pool of sera from patients fulfilling CDC criteria for Lyme disease, acquired in the North Central United States. A pool of negative control sera was obtained from human blood donors in Houston, Texas. Enzyme-linked immunosorbent assays (ELISAs) were performed as described (Lawrenz et al., *J. Clin. Microbiol.*, 37(12): 3997-4004, 1999), except that protein and serum concentrations were varied to determine the optimal concentrations. As shown in FIG. 6, VLS-BA13 protein (50 nanograms per well) consistently yielded higher absorbance readings with the Lyme disease serum pool than with the normal serum pool, up to a serum dilution of 1:6400. Differences in absorbance between the two serum preparations (1:200 dilution) were observed with VLS-BA13 protein concentrations as low as 3.13 nanograms per well (FIG. 7). Very similar results were obtained with sera from mice infected experimentally with *Borrelia burgdorferi* and sera from uninfected mice (FIGS. C and D). Taken together, these results provide evidence that amino acid sequences corresponding to *B. afzelii* Vls protein sequences react in a specific and sensitive manner with serum antibodies from Lyme disease patients or from *B. burgdorferi* infected mice.

Example 11

Reactivity of Sera from Human Lyme Disease Patients and Infected Mice with *Borrelia garinii* Protein A recombinant DNA vector comprising a nucleotide sequence encoding the predicted amino acid sequence of the *B. garinii* Ip90 Ws cassette 10 (SEQ ID NOs:94 and 95) has been constructed. Briefly, DNA containing the coding sequence of the cassette region was amplified using a two-step polymerase chain reaction (PCR) method. During the first amplification, specific primers flanking the *B. garinii* Ip90 vls cassette 10 (5'-CGGGATCCGCTGTTGGGAG-TYGCAAC-3' (SEQ ID NO:102) and 5'-AACTGCAGAT-TATCATGAGCAGCATCCTTC-3' (SEQ ID NO:103)) were used with *B. garinii* Ip90 DNA as template to amplify a fragment containing the desired cassette. Then a second PCR was performed using primers specific for the cassette region itself (5'-CG GGATCCAAGGGGACTGTTAAGAATGCTGTTG-3' (SEQ ID NO:104) and 5'-TT CTGCAGATGATTATCATGAGCAGCATCCTTCA-3'(SEQ ID NO:105)) and the purified product of the first reaction as the DNA template. The two primers contained BamHI and PstI sites, respectively (underlined); the PCR product was treated with these two enzymes and ligated into the expression vector pQE30 cut with the same two enzymes. The sequence of the insert was analyzed and found to be the correct sequence. The resulting recombinant plasmid, pBG-10-1 was used to transform *E. coli* cells, and expression was induced by incubation of a transformed *E. coli* clone to 1 mM isopropyl-β-D-thiogalactopyranoside (IPTG) for 3 hours. The *E. coli* cells were lysed by sonication and centrifuged to remove cellular debris. The recombinant, His6-tagged protein (VLS-BG10) was purified by liquid chromatography over a nickel affinity column, elution of bound protein with imidazole, and further purification using a heparin-Sepharose column. The purity of the protein was determined to be >90% by sodium-dodecyl sulfate polyacrylamide gel electrophoresis (SDS-PAGE), and the concentration determined by a Bradford protein assay.

Figure 10:
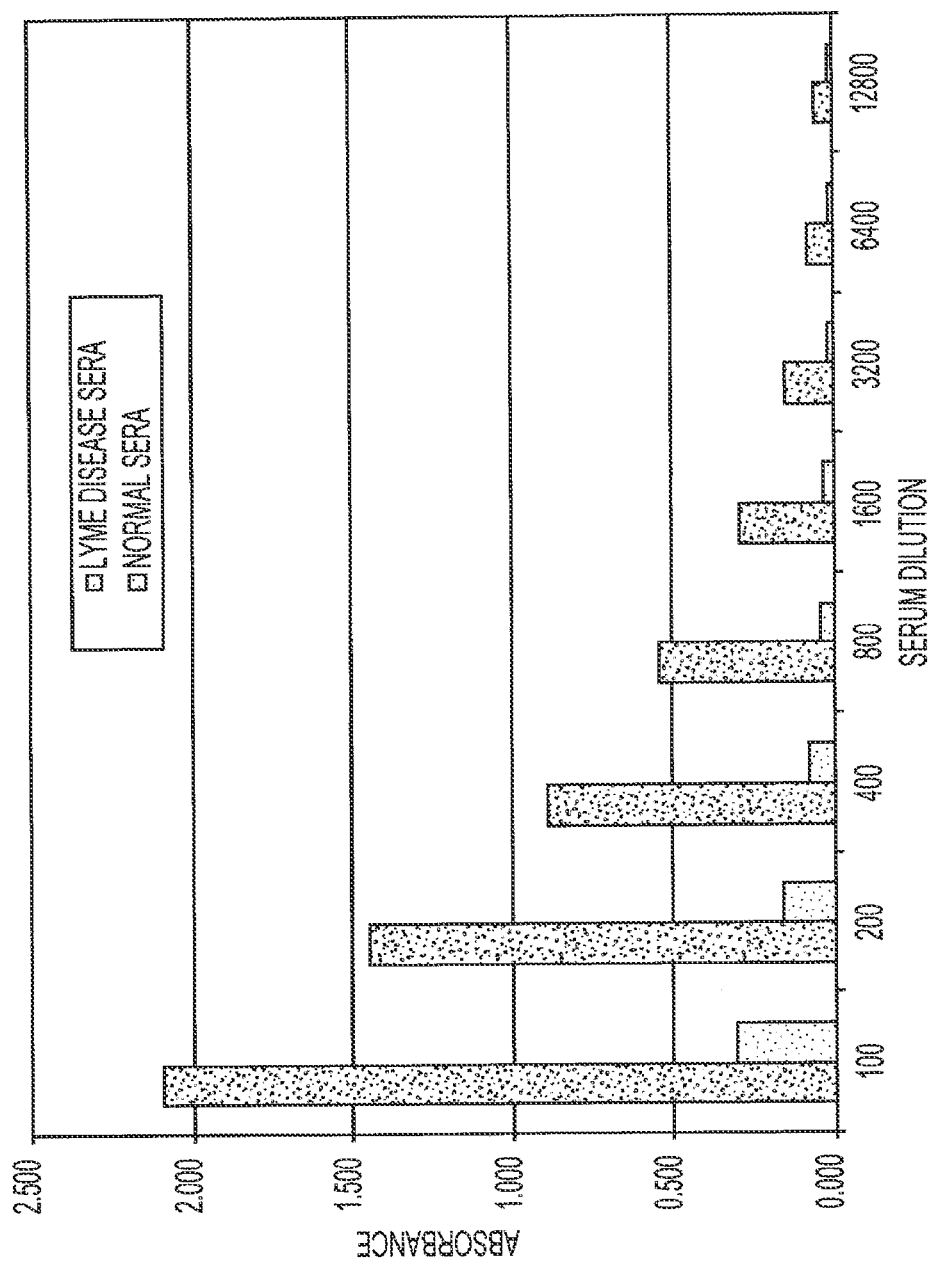
FIG. 10. Reactivity of human Lyme disease serum pool and a normal human serum pool with recombinant *Borrelia garinii* Vls protein VLS-BG10.
Figure 11:
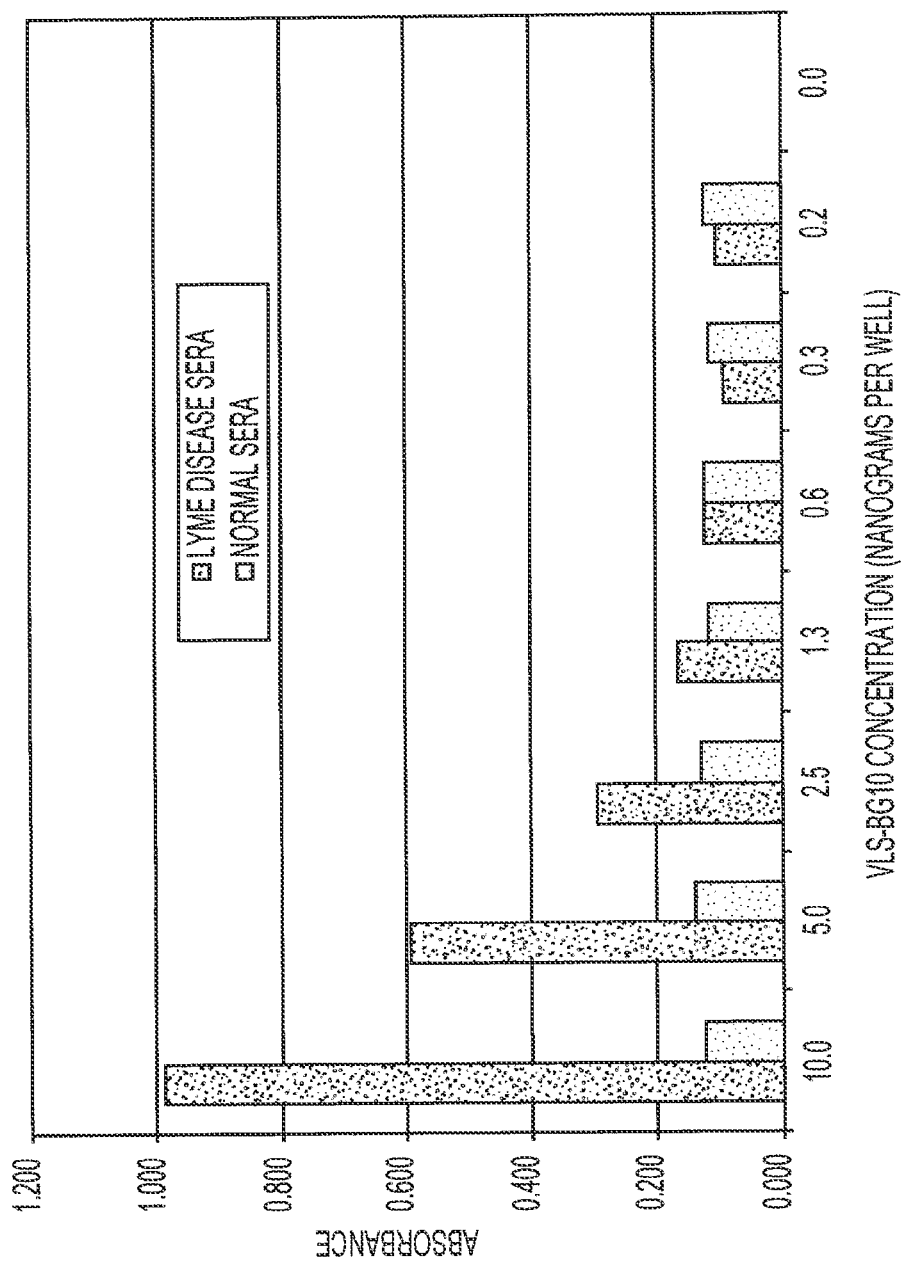
FIG. 11. Effect of VLS-BG10 protein concentration on enzyme immunoassay reactivity of serum pools from Lyme disease human subjects and normal human subjects.
Figure 12:
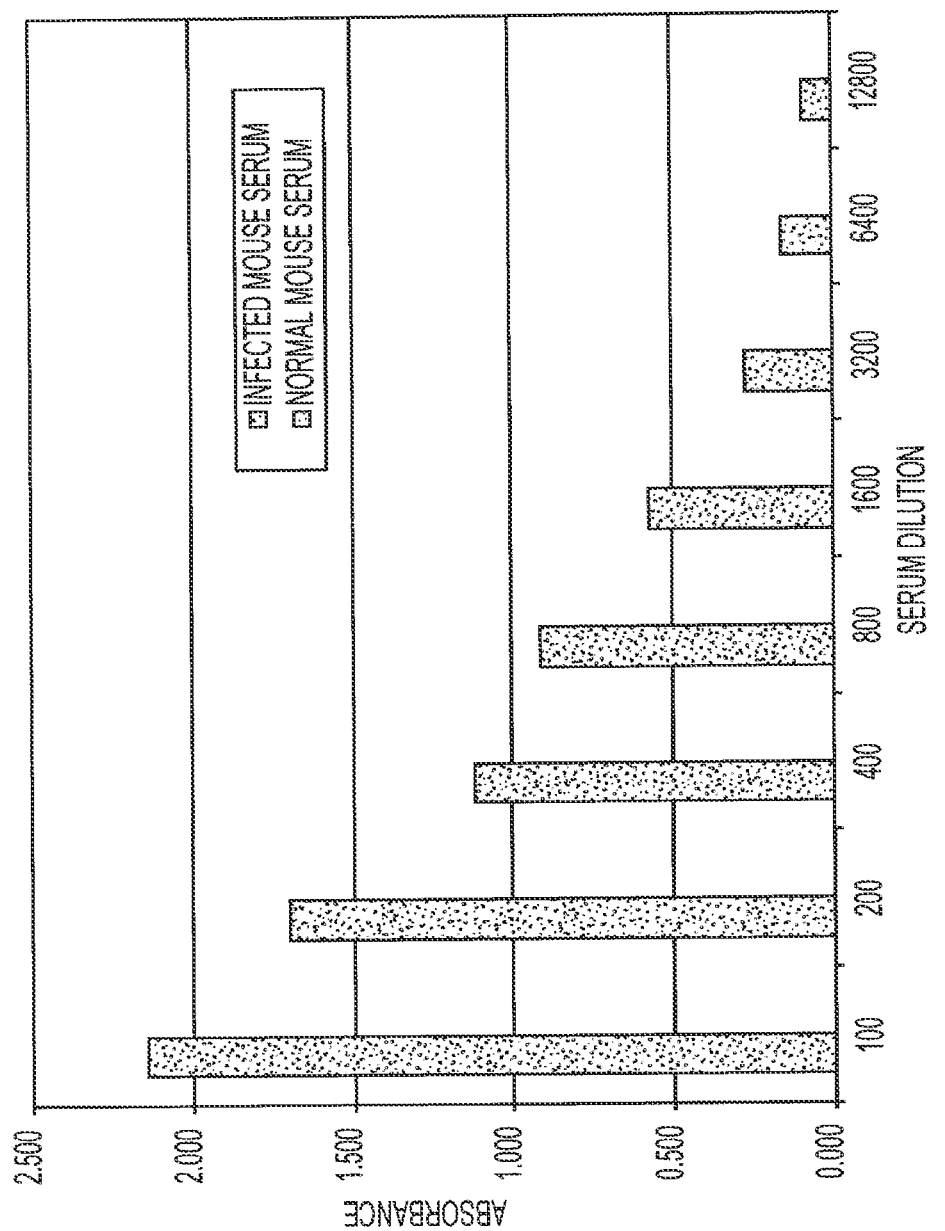
FIG. 12. Reactivity of mouse anti-*Borrelia burgdorferi* serum and normal mouse serum with recombinant *Borrelia garinii* Vls protein VLS-BG10. The reactivity of normal mouse serum was below background levels.
Figure 13:
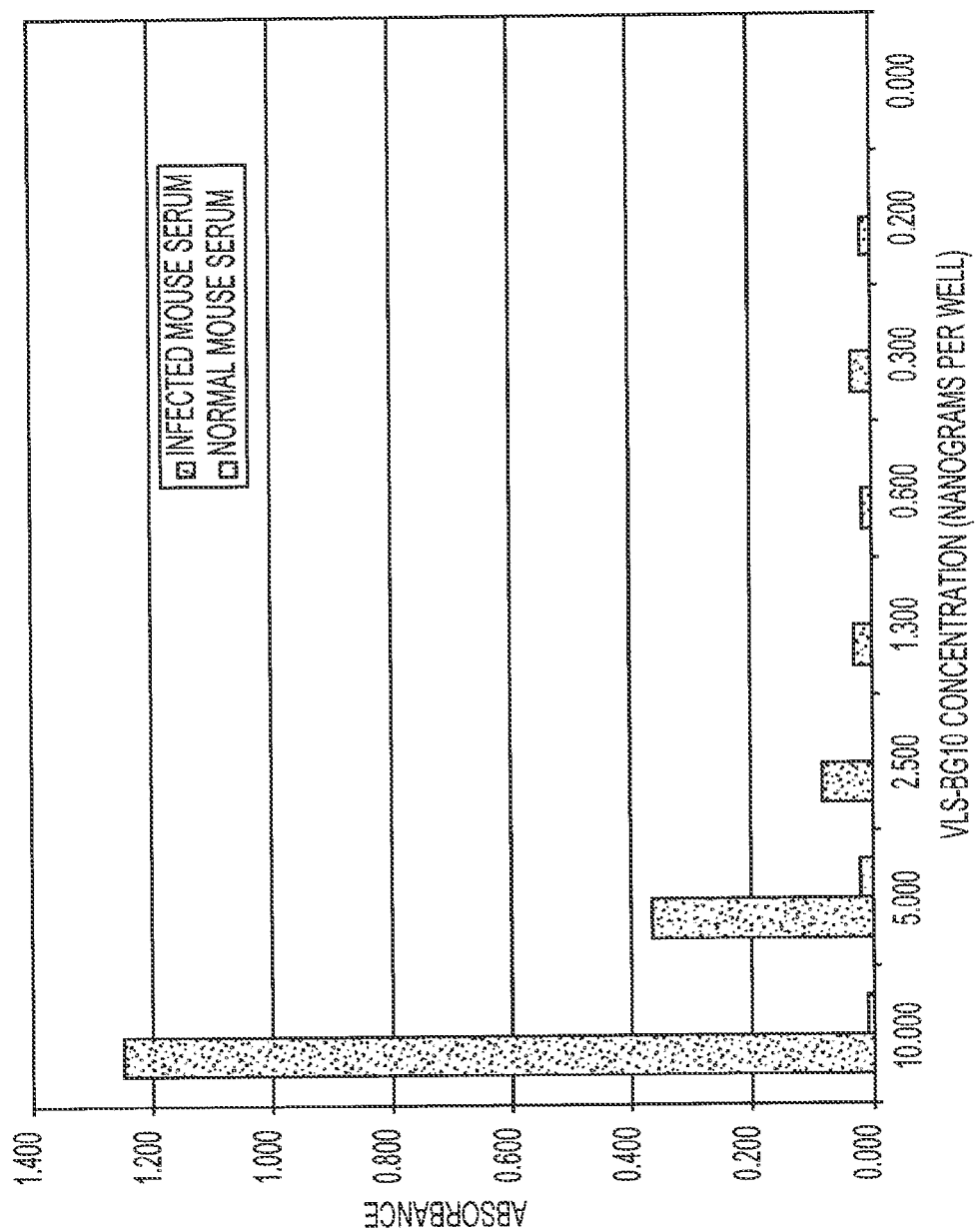
FIG. 13. Effect of VLS-BG10 protein concentration on enzyme immunoassay reactivity of mouse anti-*B. burgdorferi* antiserum and normal mouse serum. The reactivity of normal mouse serum was below background levels.

The purified recombinant protein VLS-BG10 was tested for reactivity with antibodies from humans using a pool of sera from patients fulfilling CDC criteria for Lyme disease, acquired in the North Central United States. A pool of negative control sera was obtained from human blood donors in Houston, Texas. Enzyme-linked immunosorbent assays (ELISAs) were performed as described (Lawrenz et al., *J. Clin. Microbiol.*, 37(12): 3997-4004, 1999), except that protein and serum concentrations were varied to determine the optimal concentrations. In the examples shown, the antigen (VLS-BG10) was used to coat the wells, and the measured parameter was the amount of antibody bound as determined by addition of either goat anti-human IgG (alkaline phosphatase conjugate) or goat anti-mouse IgG (alkaline phosphatase conjugate), followed by washing and addition of a suitable substrate. As shown in FIG. 10, VLS-BG10 protein (10 nanograms per well) consistently yielded higher absorbance readings with the Lyme disease serum pool than with the normal serum pool, up to a serum dilution of 1:6400. Differences in absorbance between the two serum preparations (1:200 dilution) were observed with VLS-BG10 protein concentrations as low as 0.031 micrograms per well (FIG. 11). Very similar results were obtained with sera from mice infected experimentally with *Borrelia burgdorferi* and sera from uninfected mice (FIGS. 12 and 13). Taken together, these results provide evidence that amino acid sequences corresponding to *B. garinii* Vls protein sequences react in a specific and sensitive manner with serum antibodies from Lyme disease patients or from *B. burgdorferi* infected mice.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 4,196,265
U.S. Pat. No. 4,518,584
U.S. Pat. No. 4,554,101
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,683,195
U.S. Pat. No. 4,683,202
U.S. Pat. No. 5,155,022
U.S. Pat. No. 5,168,050
U.S. Pat. No. 5,178,859
U.S. Pat. No. 5,187,065
U.S. Pat. No. 5,217,872
U.S. Pat. No. 5,246,844
U.S. Pat. No. 5,279,938
U.S. Pat. No. 5,283,175
U.S. Pat. No. 5,324,630
U.S. Pat. No. 5,385,826
U.S. Pat. No. 5,403,718
U.S. Pat. No. 5,434,077
U.S. Pat. No. 5,436,000
U.S. Pat. No. 6,437,116
Altschul, Gish, Miller, Myers, Lipman, "Basic local alignment search tool," *J. Mol. Biol.*, 215:403-410, 1990.
Asbrink, Hederstedt, Hovmark, "The spirochetal etiology of erythema chronicum migrans Afzelius," *Acta Derm. Venerol.*, 64:291-295, 1984.

Balmelii and Piffatetti, "Analysis of the genetic polymorphism of *Borrelia burgdorferi* sensu lato by multilocus enzyme electrophoresis," *Int. J. Syst. Bacteriol.*, 46:167-172, 1996.

Barbour, "Plasmid analysis of *Borrelia burgdorferi*, the Lyme disease agent," *J. Clin. Microbiol.*, 42:475-478, 1988.

Barbour, "Plasmid analysis of *Borrelia burgdorferi*, the Lyme disease agent," *J. Clin. Microbiol.*, 26:475-478, 1988.

Barbour, "Linear DNA of *Borrelia* species and antigenic variation," *Trends Microbiol.*, 1:236-239, 1993.

Barbour and Garon, "Linear plasmids of the bacterium *Borrelia burdorferi* have covalently closed ends," *Science*, 237:409-411, 1987.

Barbour, Burman, Carter, Kitten, Bergstrom, "Variable antigen genes of the relapsing fever agent *Borrelia hermsii* are activated by promoter addition," *Mol. Microbiol.*, 5:489-493, 1991a.

Barbour, Carter, Burman, Freitag, Garon, Bergstrom, "Tandem insertion sequence-like elements define the expression site for variable antigen genes of *Borrelia hermsii*," *Infect. Immun.*, 59:390-397, 199 lb.

Barbour et al., "Structural analysis of the variable major proteins of *Borrelia hermsii*," *J. Exp. Med.*, 158:2127-2140, 1983.

Barbour et al., "Variable major proteins of *Borrelia hermsii*," *J. Exp. Med.*, 156:1312-1324, 1982.

Barstad et al., "Variable major proteins of *Borrelia hermsii*. Epitope mapping and partial sequence analysis of CNBr peptides," *J. Exp. Med.*, 161:1302-1314, 1985.

Barthold, "Antigenic stability of *Borrelia burgdorferi* during chronic infections of immunocompetent mice," *Infect. Immun.*, 61:4955-4961, 1993.

Barthold, Moody, Beck, "Suspectibility of laboratory rats to isolates of *Borrelia burgdorferi* from different geographic areas," *Am. J. Trop. Med. Hyg.*, 42:596-600, 1990.

Borst and Geaves, "Programmed gene rearrangements altering gene expression," *Science*, 235:658-667, 1987.

Borst, Bitter, McCulloch, Leeuwen, Rudenko, "Antigenic variation in malaria," *Cell*, 82:104, 1995.

Burgdorfer, Barbour, Hayes, Benach, Grunwaldt, Davis, "Lyme disease, a tick-borne spirochetosis?," *Science*, 216:1317-1319, 1982.

Carroll and Gheradini, "Membrane protein variations associated with in vitro passage of *Borrelia burgdorferi*," *Infect. Immun.*, 64:392-398, 1996.

Carter et al., "A family of surface-exposed proteins of 20 kilodaltons in the genus *Borrelia*," *Infect. Immun.*, 62:2792-2799, 1994.

Casjens, Delange III, Ley, Rosa, Huang, "Linear chromosomes of Lyme disease agent spirochetes: genetic diversity and conservation of gene order," *J. Bacteriol.*, 177:2769-2780, 1995.

Demolis, Mallet, Bussereau, Jacquet, "Improved strategy for large-scale DNA sequencing using DNase I cleavage for generating radom subclones," *Biotechniques*, 18:453-457, 1995.

Dever, Jorgensen, Barbour, "In vitro antimocrobial susceptibility testing of *Borrelia burgdorferi*: a microdilution MIC method and time-kill studies," *J. Clin. Microbiol.*, 30:2692-2697, 1992.

Donelson, "Mechanisms of antigenic variation in *Borrelia hermsii* and African trypanosomes," *J. Biol. Chem.*, 270:7783-7786, 1995.

Fuchs, Jauris, Lottspeich, Preacmursic, Wilskie, Soutschek, "Molecular analysis and expression of a *Borrelia burgdorferi* gene encoding a 22 kDa protein (pC) in *E. coli*," *Mol. Microbiol.*, 6:503-509, 1992.

Haas and Meyer, "The repertoire of silent pilus genes in *Neisseria gonorrhoeae*: evidence for gene conversion," *Cell*, 44:107-115, 1986.

Hagblom, Segal, Billyard, So, "Intragenic recombination leads to pilus antigenic variation in *Neisseria gonorrhoeae*," *Nature*, 315:156-158, 1985.

Hinnebusch, Bergstrom, Barbour, "Cloning and sequence analysis of linear plasmid telomeres of the bacterium *Borrelia burgdorferi*," *Mol. Microbiol.*, 4:811-820, 1990.

Hofman and Baron, "Boxshade 3.21 [WWW Document] accessed on the World Wide Web at isrec.isbsib.ch:8080/software/BOX_form.html, 1996.

Hudson, Frye, Quinn, Gherardini, "Increased expression of *Borrelia burgdorferi* vlsE in response to human endothelial cell membranes, *Mol. Microbiol.*, 41:229-239, 2001.

Hughes and Johnson, "Methylated DNA in *Borrelia* species," *J. Bacteriol.*, 172:6602-6604, 1990.

Indest, Howell, Jacobs, School-Meker, Norris, Phillipp, "Analysis of *Borrelia burgdorferi* vlsE gene expression and recombination in the tick vector," *Infect. Immun.*, 69:7083-7090, 2001.

Johnson et al., "Infection of Syrian hamsters with Lyme disease spirochetes," *J. Clin. Microbiol.*, 20:1099-1101, 1984.

Jonsson, Ilver, Falk, Pepose, Normark, "Sequence changes in the pilus subunit lead to tropism variation of *Neisseria gonorrhoeae* to human tissue," *Mol. Microbiol.*, 13:403-416, 1994.

Kitten and Barbour, "Juxtaposition of expressed variable antigen genes with a conserved telomere in the bacterium *Borrelia hermsii*," *Proc. Natl. Acad. Sci. USA*, 87:6077-6081, 1990.

Kitten and Barbour, "The relapsing fever agent *Borrelia hermsii* has multiple copies of its chromosome and linear plasmids," *Genetics*, 132:311-324, 1992.

Koomey, Gotschlich, Robbins, Bergstrom, Swanson, "Effects of recA mutations on pilus antigenic variation and phase transitions in *Neisseria gonorrhoeae*," *Genetics*, 117:391-398, 1987.

Kriuchechnikov, Korenberg, Shcherbakov, Kovalevskii, Levin, "Identification of *borrelia* isolated in the USSR from *Ixodes persulcatus* Schulze ticks", *Zh Mikrobiol. Epidemiol. Immunobiol.*, 12:41-44, 1988.

Kupsch, Knepper, Kuroki, Heuer, Meyer, "Variable opacity (Opa) outer membrane proteins account for the cell tropisms displayed by *Neisseria gonorrhoeae* for human leukocytes and epithelial cells," *EMBO. J.*, 12:641-650, 1993.

Lambden, Robertson, Watt, "Biological properties of two distinct pilus types produced by isogenic variants of *Neisseria gonorrhoeae* P9," *J. Bacteriol.*, 141:393-396, 1980.

Liang and Philipp, "Analysis of antibody response to invariable regions of VlsE, the variable surface antigen of *Borrelia burgdorferi*," *Infect. Immun.*, 67:6702-6706, 1999.

Liang, Alvarez, Gu, Nowling, Ramamoorthy, Philipp, "An immunodominant conserved region within the variable domain of VlsE, the variable surface antigen of *Borrelia burgdorferi*," *J. Immunol.*, 163:5566-5573, 1999a.

Liang, Aberer, Cinco, Gern, Hu, Lobet, Ruscio, Voet, Jr., Weynants, Philipp, "Antigenic conservation of an immunodominant invariable region of the VlsE lipoprotein among European pathogenic genospecies of *Borrelia burgdorferi* SL," *J. Infect. Dis.*, 182:1455-1462, 2000a.

Livey, Gibbs, Schuster, Dorner, "Evidence for lateral transfer and recombination in OspC variation in Lyme disease *Borrelia*," *Mol. Microbiol.*, 18:257-269, 1995.

Marconi, Konkel, Garon, "Variability of osp genes and gene products among species of Lyme disease spirochetes," *Infect. Immun.*, 61:2611-2617, 1993.

Marconi, Samuels, Landry, Garon, "Analysis of the distribution and molecular heterogeneity of the ospD gene among the Lyme disease spriochetes: evidence for lateral gene exchange," *J. Bacteriol.*, 176:4572-4582, 1994.

Margolis et al., "Homology between *Borrelia burgdorferi* OspC and members of the family of *Borrelia hermsii* variable major proteins," *Gene,* 143:105-110, 1994.

Meier, Simon, Barbour, "Antigenic variation is associated with DNA rearrangements in a relapsing fever *Borrelia*," *Cell,* 41:403-409, 1985.

Meyer, Mlawer, So, "Pilus expression in *Neisseria gonorrhoeae* involves chromosomal rearrangement," *Cell,* 30:45-52, 1982.

Moody et al., "Lyme borreliosis in laboratory animals: effect of host species and in vitro passage of *Borrelia burgdorferi*," *Am. J. Trop. Med. Hyg.,* 43:87-92, 1990.

Nassif, Lowry, Stenberg, O'Gaora, Ganji, So, "Antigenic variation of pilin regulates adhesion of *Neisseria meningitidis* to human epithelial cells," *Mol. Microbiol.,* 8:719-725, 1993.

Norris, Carter, Howell, Barbour, "Low-passage-associated proteins of *Borrelia burgdoreferi* B31: characterization and molecular cloning of OspD, a surface-exposed, plasmid-encoded lipoprotein," *Infect. Immun.,* 60:4662-4672, 1992.

Norris et al., "High- and low-infectivity phenotypes of clonal populations of in vitro-cultured *Borrelia burgdorferi*," *Infect. Immun.,* 63:2206-2212, 1995.

Norris et al., "Low-passage-associated proteins of *Borrelia burgdorferi* B31: characterization and molecular cloning of OspD, a surface exposed, plasmid-encoded lipoprotein," *Infect. Immun.,* 60:4662-4672, 1992.

Persing, Mathiesen, Podzorski, Barthold, "Genetic stability of *Borrelia burgdorferi* recovered from chronically infected immunocompetent mice," *Infect. Immun.,* 62:3521-3527, 1994.

Plasterk et al., "Transposition of structural genes to an expression sequence on a linear plasmid causes antigenic variation in the bacterium *Borrelia hermsii*," *Nature,* 318:257-263, 1985.

Purser and Norris, "Correlation between plasmid content and infectivity in *Borrelia burgdorferi*, *Proc. Natl. Acad. Sci. USA,* 97:13865-13870, 2000.

Restrepo and Barbour, "Antigen diversity in the bacterium *B. hermsii* through 'somatic' mutations in rearranged vmp genes," *Cell,* 78:867-876, 1994.

Restrepo, Carter, Barbour, "Activation of a vmp pseudogene in *Borrelia hermsii*: an alternate mechanism of antigenic variation during relapsing fever," *Mol. Microbiol.,* 13:287-299, 1994.

Restrepo, Kitten, Carter, Infante, Barbour, "Subtelomeric expression regions of *Borrelia hermsii* linear plasmids are highly polymorphic," *Mol. Microbiol.,* 6:3299-3311, 1992.

Robertson and Meyer, "Genetic variation in pathogenic bacteria," *Trends Genet.,* 8:422-427, 1992.

Rosa, Samuels, Hogan, Stevenson, Casjens, Tilly, "Directed insertion of a selectable marker into a circular plasmid of *Borrelia burgdorferi*," *J. Bacteriol.,* 178:5946-5953, 1996.

Rosa, Schwan, Hogen, "Recombination between genes encoding major surface proteins A and B of *Borrelia burgdorferi*," *Mol. Microbiol.,* 6:3031-3040, 1992.

Rudel, Van Putten, Gibbs, Haas, Meyer, "Interaction of two variable proteins (PilE and PilC) required for pilus-mediated adherence of *Neisseria gonorrhoeae* to human epithelial cells," *Mol. Microbiol.,* 6:3439-3450, 1992.

Sadziene, Rosa, Thompson, Hogan, Barbour, "Antibody-resistant mutations of *Borrelia burgdorferi*: in vitro selection and characterization," *J. Exp. Med.,* 176:799-809, 1992.

Sambrook, Fritsch, Maniatis, "Molecular cloning: a laboratory manual," Cold Spring Harbor, N.Y.: Cold Spring Harbor Laboratory Press, 1989.

Sambrook, Fritsch, Maniatis, "Molecular cloning: a laboratory manual," Cold Spring Harbor, N.Y.: Cold Spring Harbor Laboratory Press, 2001.

Samuels, Mach, Garon, "Genetic transformation of the Lyme disease agent *Borrelia burgdorferi* with coumarin-resistant gyrB," *J. Bacteriol.,* 176:6045-6049, 1994.

Schutzer, "Lyme disease: Molecular and immunologic approaches. In: *Current communications in cell and molecular biology,*" J. Inglis and J. A. Witkowski, eds. (Cold Spring Harbor, N.Y.: Cold Spring Harbor Laboratory Press).

Schwann et al., "Changes in infectivity and plasmid profile of the Lyme disease spirochete, *Borrelia burgdorferi*, as a result of in vitro cultivation," *Infect. Immun.,* 56:1831-1836, 1988a.

Schwann, Burgdorfer, Schrumpg, Karstens, "The urinary bladder, a consistent source of *Borrelia burgdorferi* in experimentally infected white-footed mice (*Peromyscus leucopcus*)," *J. Clin. Microbiol.,* 26:893-895, 1988b.

Schwann, Karstens, Schrumpf, Simpson, "Changes in antigenic reactivity of *Borrelia burgdorferi*, the Lyme disease spirochete, during persistent infection of mice," *Can. J. Microbiol.,* 37:450-454, 1991.

Seal, Jackson, Daniels, "Isolation of a *Pseudomonas solanacearum*-specific DNA probe by subtraction hybridization and construction of species-specific oligonucleotide primers for sensitive detection by the polymerase chain reaction," *Appl. Environ. Microbiol.,* 58:3751-3758, 1992.

Segal, Hagblom, Seifert, So, "Antigenic variation of gonococcal pilus involves assembly of separated silent gene segments," *Proc. Natl. Acad. Sci. USA,* 83:2177-2181, 1986.

Seifert and So, "Genetic mechanisms of bacterial antigenic variation," *Microbiol. Rev.,* 52:327-336, 1988.

Smith, Wiese, Wojznysni, Davison, Worley, "BCM Search Launcer—an integrated interface to molecular biology data base search and analysis services available on the World Wide Web, *Genome Res.,* 6:454-462, 1996.

Steere, "Lyme disease," *N. Engl. J. Med.,* 321:586-596, 1989.

Stevenson, Bockenstedt, Barthold, "Expression and gene sequence of outer surface protein C of *Borrelia burgdorferi* reisolated from chronically infected mice," *Infect. Immun.,* 62:3568-3571, 1994.

Stoenner, Dodd, Larsen, "Antigenic variation of *Borrelia hermsii,*" *J. Exp. Med.,* 156:1297-1311, 1982.

Swanson and Koomey, "Mechanisms for variation of pili and outer membrane protein II in *Neisseria gonorrhoeae,*" D. E. Berg and M. M. Howe, Eds. (Washington, D.C.: American Society for Microbiology).

Thiessen et al., "Evolution of the *Borrelia burgdorferi* outer surface protein OspC," *J. Bacteriol.,* 177:3036-3044, 1995.

TIGR, The Institute for Genomic Research (accessed on the World Wide Web at tigr.org), 2002.

Wainwright, Pritchard, Seifert, "A conserved DNA sequence is required for efficient gonococcal pilin antigenic variation," *Mol. Microbiol.,* 13:75-87, 1994.

Walker, Howell, You, Hoffmaster, Heath, Weinstock, Norris, "Physical map of the genome of *Treponema pallidum* subsp. *Pallidum* (Nichols)," *J. Bacteriol.,* 177:1797-1804, 1995.

Wang, van Dam, Dankert, "Analysis of a VMP-like sequence (vls) locus in *Borrelia garinii* and Vls homologues among four *Borrelia burgdorferi* sensu lato species," FEMS Microbiol. Lett., 3199:9-45, 2001.

Wilske, Barbour, Bergstrom, Burman, Restrepo, Rosa, Schwan, Soutschek, Wallich, "Antigenic variation and strain heterogeneity in *Borrelia* spp.," *Res. Microbiol.*, 143: 583-596, 1992.

Wu and Tokunaga, "Biogenesis of lipoproteins in bacteria," *Curr. Top. Microbiol. Immunol.*, 125:127-157, 1986.

Xu, Kodner, Coleman, Johnson, "Correlation of plasmids with infectivity of *Borrelia burgdorferi* senso stricto type strain B31," *Infect. Immun.*, 64:3870-3876, 1996.

Xu and Johnson, "Analysis and comparison of plasmid profile of *Borrelia burgdorferi* sensu lato strains," *J. Clin. Microbiol.*, 33:2679-2685, 1995.

Zhang, Hardman, Barbour, Norris, "Antigenic variation in Lyme disease borreliae by promiscuous recombination of VMP-like sequence cassettes," *Cell*, 89:275-285, 1997.

Zhang and Norris, "Genetic variation of the *Borrelia burgdorferi* gene vslE involves cassette-specific, segmental gene conversation," *Infect. Immun.*, 66:3698-3704, 1998a.

Zhang and Norris, "Kinetics and in vivo induction of genetic variation of vlsE in *Borrelia burgdorferi, Infect. Immun.*, 66:3689-3697, 1998b.

I claim:

1. A recombinant nucleic acid comprising:
   (i) a nucleotide sequence operably linked to a heterologous promoter, wherein said nucleotide sequence encodes at least 16 contiguous amino acids of SEQ ID NO: 97; or
   (ii) a nucleotide sequence operably linked to a heterologous promoter, wherein said nucleotide sequence encodes at least 35 contiguous amino acids of SEQ ID NO: 95.

2. The recombinant nucleic acid of claim 1, wherein the nucleotide sequence encodes at least 16 contiguous amino acids of SEQ ID NO: 97.

3. The recombinant nucleic acid of claim 1, wherein the nucleotide sequence encodes at least 20 contiguous amino acids of SEQ ID NO: 97.

4. The recombinant nucleic acid of claim 3, wherein the nucleotide sequence encodes at least 35 contiguous amino acids of SEQ ID NO: 97.

5. The recombinant nucleic acid of claim 3, wherein the nucleotide sequence encodes at least 50 contiguous amino acids of SEQ ID NO: 97.

6. The recombinant nucleic acid of claim 3, wherein the nucleotide sequence encodes the sequence of SEQ ID NO: 97.

7. The recombinant nucleic acid of claim 2, wherein the nucleic acid comprises at least 50 contiguous nucleotides of SEQ ID NO: 96.

8. The recombinant nucleic acid of claim 2, wherein the nucleic acid comprises at least 75 contiguous nucleotides of SEQ ID NO: 96.

9. The recombinant nucleic acid of claim 2, wherein the nucleic acid comprises at least 103 contiguous nucleotides of SEQ ID NO: 96.

10. The recombinant nucleic acid of claim 2, wherein the nucleic acid comprises at least 110 contiguous nucleotides of SEQ ID NO: 96.

11. The recombinant nucleic acid of claim 2, wherein the nucleic acid comprises the nucleotide sequence of SEQ ID NO: 96.

12. The recombinant nucleic acid of claim 1, wherein the nucleotide sequence encodes at least 35 contiguous amino acids of SEQ ID NO: 95.

13. The recombinant nucleic acid of claim 12, wherein the nucleotide sequence encodes at least 50 contiguous amino acids of SEQ ID NO: 95.

14. The recombinant nucleic acid of claim 12, wherein the nucleotide sequence encodes the sequence of SEQ ID NO: 95.

15. The recombinant nucleic acid of claim 12, wherein the nucleic acid comprises at least 105 contiguous nucleotides of SEQ ID NO: 94.

16. The recombinant nucleic acid of claim 12, wherein the nucleic acid comprises at least 110 contiguous nucleotides of SEQ ID NO: 94.

17. The recombinant nucleic acid of claim 12, wherein the nucleic acid comprises the nucleotide sequence of SEQ ID NO: 94.

18. A host cell comprising a recombinant nucleic acid of claim 1.

19. The host cell of claim 18, wherein the cell is an *E. coli* cell.

20. The recombinant host cell of claim 18, wherein the nucleotide sequence encodes at least 16 contiguous amino acids of SEQ ID NO: 97.

21. The recombinant host cell of claim 18, wherein the nucleotide sequence encodes at least 35 contiguous amino acids of SEQ ID NO: 95.

22. A method of assaying for *Borrelia* infection comprising:
   (a) contacting a sample obtained from a subject with an isolated polypeptide, said isolated polypeptide being immobilized on a surface and comprising:
      (i) at least 16 contiguous amino acids of SEQ ID NO: 97; or
      (ii) at least 35 contiguous amino acids of SEQ ID NO: 95; and
   (b) determining whether immunologic binding occurs between the isolated polypeptide and an antibody in the sample, wherein immunologic binding is indicative of *Borrelia* infection.

23. The method of claim 22, wherein the isolated polypeptide sequence comprises at least 16 contiguous amino acids of SEQ ID NO: 97.

24. The method of claim 22, wherein the isolated polypeptide sequence comprises at least 35 contiguous amino acids of SEQ ID NO: 95.

25. The method of claim 22, wherein the isolated polypeptide comprises a label.

26. The method of claim 22, wherein the isolated polypeptide is a fusion protein.

27. The method of claim 22, further defined as comprising performing an ELISA assay.

* * * * *

SEQUENCE LISTING

```
<160> NUMBER OF SEQ ID NOS: 107

<210> SEQ ID NO 1
<211> LENGTH: 1227
<212> TYPE: DNA
<213> ORGANISM: Borrelia burgdorferi
<220> FEATURE:
<221> NAME/KEY: CDS
<222> LOCATION: (75)..(1142)

<400> SEQUENCE: 1
acctacactt gttaaaactc tcttttgag ttaagatgat aacttatact tttcattata      60
aggagacgat gaat atg aaa aaa att tca agt gca agt tta tta aca act     110
              Met Lys Lys Ile Ser Ser Ala Ser Leu Leu Thr Thr
                1               5                  10 ttc ttt gtt ttt att aat tgt aaa agc caa gtt gct gat aag gac gac    158
Phe Phe Val Phe Ile Asn Cys Lys Ser Gln Val Ala Asp Lys Asp Asp
         15                  20                  25 cca aca aac aaa ttt tac caa tct gtc ata caa tta ggt aac gga ttt    206
Pro Thr Asn Lys Phe Tyr Gln Ser Val Ile Gln Leu Gly Asn Gly Phe
     30                  35                  40 ctt gat gta ttc aca tct ttt ggt ggg tta gta gca gag gct ttt gga    254
Leu Asp Val Phe Thr Ser Phe Gly Gly Leu Val Ala Glu Ala Phe Gly
45                  50                  55                  60 ttt aaa tca gat cca aaa aaa tct gat gta aaa acc tat ttt act act    302
Phe Lys Ser Asp Pro Lys Lys Ser Asp Val Lys Thr Tyr Phe Thr Thr
                 65                  70                  75 gta gct gcc aaa ttg gaa aaa aca aaa acc gat ctt aat agt ttg cct    350
Val Ala Ala Lys Leu Glu Lys Thr Lys Thr Asp Leu Asn Ser Leu Pro
             80                  85                  90 aag gaa aaa agc gat ata agt agt acg acg ggg aaa cca gat agt aca    398
Lys Glu Lys Ser Asp Ile Ser Ser Thr Thr Gly Lys Pro Asp Ser Thr
         95                 100                 105 ggt tct gtt gga act gcc gtt gag ggg gct att aag gaa gtt agc gag    446
Gly Ser Val Gly Thr Ala Val Glu Gly Ala Ile Lys Glu Val Ser Glu
    110                 115                 120 ttg ttg gat aag ctg gta aaa gct gta aag aca gct gag ggg gct tca    494
Leu Leu Asp Lys Leu Val Lys Ala Val Lys Thr Ala Glu Gly Ala Ser
125                 130                 135                 140 agt ggt act gct gca att gga gaa gtt gtg gct gat gct gat gct gca    542
Ser Gly Thr Ala Ala Ile Gly Glu Val Val Ala Asp Ala Asp Ala Ala
                145                 150                 155 aag gtt gct gat aag gcg agt gtg aag ggg att gct aag ggg ata aag    590
Lys Val Ala Asp Lys Ala Ser Val Lys Gly Ile Ala Lys Gly Ile Lys
            160                 165                 170 gag att gtt gaa gct gct ggg ggg agt gaa aag ctg aaa gct gtt gct    638
Glu Ile Val Glu Ala Ala Gly Gly Ser Glu Lys Leu Lys Ala Val Ala
        175                 180                 185
```

```
gct gct aaa ggg gag aat aat aaa ggg gca ggg aag ttg ttt ggg aag      686
Ala Ala Lys Gly Glu Asn Asn Lys Gly Ala Gly Lys Leu Phe Gly Lys
    190                 195                 200 gct ggt gct gct gct cat ggg gac agt gag gct gct agc aag gcg gct      734
Ala Gly Ala Ala Ala His Gly Asp Ser Glu Ala Ala Ser Lys Ala Ala
205                 210                 215                 220 ggt gct gtt agt gct gtt agt ggg gag cag ata tta agt gcg att gtt      782
Gly Ala Val Ser Ala Val Ser Gly Glu Gln Ile Leu Ser Ala Ile Val
                225                 230                 235 acg gct gct gat gcg gct gag cag gat gga aag aag cct gag gag gct      830
Thr Ala Ala Asp Ala Ala Glu Gln Asp Gly Lys Lys Pro Glu Glu Ala
    240                 245                 250 aaa aat ccg att gct gct gct att ggg gat aaa gat ggg ggt gcg gag      878
Lys Asn Pro Ile Ala Ala Ala Ile Gly Asp Lys Asp Gly Gly Ala Glu
255                 260                 265 ttt ggt cag gat gag atg aag aag gat gat cag att gct gct gct att      926
Phe Gly Gln Asp Glu Met Lys Lys Asp Asp Gln Ile Ala Ala Ala Ile
                270                 275                 280 gct ttg agg ggg atg gct aag gat gga aag ttt gct gtg aag gat ggt      974
Ala Leu Arg Gly Met Ala Lys Asp Gly Lys Phe Ala Val Lys Asp Gly
285                 290                 295                 300 gag aaa gag aag gct gag ggg gct att aag gga gct gct gag tct gca     1022
Glu Lys Glu Lys Ala Glu Gly Ala Ile Lys Gly Ala Ala Glu Ser Ala
                305                 310                 315 gtt cgc aaa gtt tta ggg gct att act ggg cta ata gga gac gcc gtg     1070
Val Arg Lys Val Leu Gly Ala Ile Thr Gly Leu Ile Gly Asp Ala Val
        320                 325                 330 agt tcc ggg cta agg aaa gtc ggt gat tca gtg aag gct gct agt aaa     1118
Ser Ser Gly Leu Arg Lys Val Gly Asp Ser Val Lys Ala Ala Ser Lys
                335                 340                 345 gaa aca cct cct gcc ttg aat aag tgatttaatt aagtgtatgg acacgactat    1172
Glu Thr Pro Pro Ala Leu Asn Lys
    350                 355 gccctcatga ttgaggaaat agtcgagaga tatatatact aaaagataat aaata        1227

<210> SEQ ID NO 2
<211> LENGTH: 356
<212> TYPE: PRT
<213> ORGANISM: Borrelia burgdorferi

<400> SEQUENCE: 2

Met Lys Lys Ile Ser Ser Ala Ser Leu Leu Thr Thr Phe Phe Val Phe
1               5                   10                  15

Ile Asn Cys Lys Ser Gln Val Ala Asp Lys Asp Pro Thr Asn Lys
                20                  25                  30

Phe Tyr Gln Ser Val Ile Gln Leu Gly Asn Gly Phe Leu Asp Val Phe
            35                  40                  45

Thr Ser Phe Gly Gly Leu Val Ala Glu Ala Phe Gly Phe Lys Ser Asp
        50                  55                  60

Pro Lys Lys Ser Asp Val Lys Thr Tyr Phe Thr Val Ala Ala Lys
65                  70                  75                  80

Leu Glu Lys Thr Lys Thr Asp Leu Asn Ser Leu Pro Lys Glu Lys Ser
                85                  90                  95

Asp Ile Ser Ser Thr Thr Gly Lys Pro Asp Ser Thr Gly Ser Val Gly
            100                 105                 110

Thr Ala Val Glu Gly Ala Ile Lys Glu Val Ser Glu Leu Leu Asp Lys
        115                 120                 125
```

```
Leu Val Lys Ala Val Lys Thr Ala Glu Gly Ala Ser Ser Gly Thr Ala
        130                 135                 140

Ala Ile Gly Glu Val Val Ala Asp Ala Asp Ala Ala Lys Val Ala Asp
145                 150                 155                 160

Lys Ala Ser Val Lys Gly Ile Ala Lys Gly Ile Lys Glu Ile Val Glu
                165                 170                 175

Ala Ala Gly Gly Ser Glu Lys Leu Lys Ala Val Ala Ala Ala Lys Gly
                180                 185                 190

Glu Asn Asn Lys Gly Ala Gly Lys Leu Phe Gly Lys Ala Gly Ala Ala
            195                 200                 205

Ala His Gly Asp Ser Glu Ala Ala Ser Lys Ala Ala Gly Ala Val Ser
    210                 215                 220

Ala Val Ser Gly Glu Gln Ile Leu Ser Ala Ile Val Thr Ala Ala Asp
225                 230                 235                 240

Ala Ala Glu Gln Asp Gly Lys Lys Pro Glu Glu Ala Lys Asn Pro Ile
                245                 250                 255

Ala Ala Ala Ile Gly Asp Lys Asp Gly Gly Ala Glu Phe Gly Gln Asp
                260                 265                 270

Glu Met Lys Lys Asp Asp Gln Ile Ala Ala Ala Ile Ala Leu Arg Gly
            275                 280                 285

Met Ala Lys Asp Gly Lys Phe Ala Val Lys Asp Gly Glu Lys Glu Lys
    290                 295                 300

Ala Glu Gly Ala Ile Lys Gly Ala Ala Glu Ser Ala Val Arg Lys Val
305                 310                 315                 320

Leu Gly Ala Ile Thr Gly Leu Ile Gly Asp Ala Val Ser Ser Gly Leu
                325                 330                 335

Arg Lys Val Gly Asp Ser Val Lys Ala Ala Ser Lys Glu Thr Pro Pro
            340                 345                 350

Ala Leu Asn Lys
    355

<210> SEQ ID NO 3
<211> LENGTH: 1141
<212> TYPE: DNA
<213> ORGANISM: Borrelia hermsii
<220> FEATURE:
<221> NAME/KEY: CDS
<222> LOCATION: (1)..(1062)

<400> SEQUENCE: 3 atg aga aaa aga ata agt gca ata ata atg act tta ttt atg gta tta    48
Met Arg Lys Arg Ile Ser Ala Ile Ile Met Thr Leu Phe Met Val Leu
1               5                   10                  15 gta agc tgt aat agc ggt ggg gtt gcg gaa gat cct aaa act gtg tat    96
Val Ser Cys Asn Ser Gly Gly Val Ala Glu Asp Pro Lys Thr Val Tyr
                20                  25                  30 tta aca tct ata gct aat tta ggg aaa gga ttt tta gat gtt ttt gtg   144
Leu Thr Ser Ile Ala Asn Leu Gly Lys Gly Phe Leu Asp Val Phe Val
            35                  40                  45 act ttt gga gat atg gtt act gga gct ttt ggt att aag gca gat act   192
Thr Phe Gly Asp Met Val Thr Gly Ala Phe Gly Ile Lys Ala Asp Thr
    50                  55                  60 aag aaa agt gat ata ggg aag tat ttt act gat att gag agc act atg   240
Lys Lys Ser Asp Ile Gly Lys Tyr Phe Thr Asp Ile Glu Ser Thr Met
65                  70                  75                  80 aca tca gtt aaa aag aag ttg caa gat gaa gtt gct aag aat ggt aac   288
Thr Ser Val Lys Lys Lys Leu Gln Asp Glu Val Ala Lys Asn Gly Asn
                85                  90                  95
```

```
tat cca aag gta aag aca gct gtt gac gaa ttt gtt gca atc tta gga    336
Tyr Pro Lys Val Lys Thr Ala Val Asp Glu Phe Val Ala Ile Leu Gly
            100                 105                 110 aag atc gag aaa gga gca aaa gaa gca tct aaa ggg gct act ggt gat    384
Lys Ile Glu Lys Gly Ala Lys Glu Ala Ser Lys Gly Ala Thr Gly Asp
        115                 120                 125 gtt att att ggg aat act gtt aag aat ggt gat gct gta cct gga gaa    432
Val Ile Ile Gly Asn Thr Val Lys Asn Gly Asp Ala Val Pro Gly Glu
    130                 135                 140 gca aca agt gtc aat tct ctt gtt aaa gga att aaa gaa ata gtt ggg    480
Ala Thr Ser Val Asn Ser Leu Val Lys Gly Ile Lys Glu Ile Val Gly
145                 150                 155                 160 gta gtc ttg aag gaa ggt aag gca gat gct gat gct act aaa gat gat    528
Val Val Leu Lys Glu Gly Lys Ala Asp Ala Asp Ala Thr Lys Asp Asp
                165                 170                 175 agt aag aaa gat att ggt aaa tta ttt acc gca acc act gat gcg aat    576
Ser Lys Lys Asp Ile Gly Lys Leu Phe Thr Ala Thr Thr Asp Ala Asn
            180                 185                 190 aga gct gat aat gcg gca gct caa gca gct gca gcg tca ata gga gca    624
Arg Ala Asp Asn Ala Ala Ala Gln Ala Ala Ala Ala Ser Ile Gly Ala
        195                 200                 205 gtg aca ggt gct gat atc ttg caa gct ata gta caa tct aag gaa aat    672
Val Thr Gly Ala Asp Ile Leu Gln Ala Ile Val Gln Ser Lys Glu Asn
    210                 215                 220 cct gtt gca aat agt act gat gga att gaa aaa gca aca gat gca gct    720
Pro Val Ala Asn Ser Thr Asp Gly Ile Glu Lys Ala Thr Asp Ala Ala
225                 230                 235                 240 gag att gca gtt gct cca gct aaa gat aat aaa aaa gag att aaa gat    768
Glu Ile Ala Val Ala Pro Ala Lys Asp Asn Lys Lys Glu Ile Lys Asp
                245                 250                 255 gga gca aaa aaa gac gca gtt att gct gca ggc att gca ctg cga gca    816
Gly Ala Lys Lys Asp Ala Val Ile Ala Ala Gly Ile Ala Leu Arg Ala
            260                 265                 270 atg gct aag aat ggt aca ttt tct att aaa aac aat gaa gat gcg gct    864
Met Ala Lys Asn Gly Thr Phe Ser Ile Lys Asn Asn Glu Asp Ala Ala
        275                 280                 285 gta acg acg ata aat agt gca gca gca agc gca gtg aac aag att tta    912
Val Thr Thr Ile Asn Ser Ala Ala Ala Ser Ala Val Asn Lys Ile Leu
    290                 295                 300 agc act cta ata ata gca ata agg aat aca gtt gat agt ggt tta aaa    960
Ser Thr Leu Ile Ile Ala Ile Arg Asn Thr Val Asp Ser Gly Leu Lys
305                 310                 315                 320 aca ata aat gag gct ctt gct aca gtt aaa caa gaa gat aaa tct gta    1008
Thr Ile Asn Glu Ala Leu Ala Thr Val Lys Gln Glu Asp Lys Ser Val
                325                 330                 335 gaa gca act aat act gca gaa gca aca act agt ggt cag caa gcg aaa    1056
Glu Ala Thr Asn Thr Ala Glu Ala Thr Thr Ser Gly Gln Gln Ala Lys
            340                 345                 350 aac tag ttaagggtaa atataaagga taaagttatt gtaagggaaa agcttttctt    1112
Asn gtttttaatg caggaatgta gtttctctg                                    1141

<210> SEQ ID NO 4
<211> LENGTH: 353
<212> TYPE: PRT
<213> ORGANISM: Borrelia hermsii

<400> SEQUENCE: 4

Met Arg Lys Arg Ile Ser Ala Ile Ile Met Thr Leu Phe Met Val Leu
```

```
                1               5                   10                  15
            Val Ser Cys Asn Ser Gly Gly Val Ala Glu Asp Pro Lys Thr Val Tyr
                        20                  25                  30
            Leu Thr Ser Ile Ala Asn Leu Gly Lys Gly Phe Leu Asp Val Phe Val
                        35                  40                  45
            Thr Phe Gly Asp Met Val Thr Gly Ala Phe Gly Ile Lys Ala Asp Thr
                50                  55                  60
            Lys Lys Ser Asp Ile Gly Lys Tyr Phe Thr Asp Ile Glu Ser Thr Met
             65                  70                  75                  80
            Thr Ser Val Lys Lys Lys Leu Gln Asp Glu Val Ala Lys Asn Gly Asn
                        85                  90                  95
            Tyr Pro Lys Val Lys Thr Ala Val Asp Glu Phe Val Ala Ile Leu Gly
                        100                 105                 110
            Lys Ile Glu Lys Gly Ala Lys Glu Ala Ser Lys Gly Ala Thr Gly Asp
                        115                 120                 125
            Val Ile Ile Gly Asn Thr Val Lys Asn Gly Asp Ala Val Pro Gly Glu
                        130                 135                 140
            Ala Thr Ser Val Asn Ser Leu Val Lys Gly Ile Lys Glu Ile Val Gly
            145                 150                 155                 160
            Val Val Leu Lys Glu Gly Lys Ala Asp Ala Asp Ala Thr Lys Asp Asp
                        165                 170                 175
            Ser Lys Lys Asp Ile Gly Lys Leu Phe Thr Ala Thr Asp Ala Asn
                        180                 185                 190
            Arg Ala Asp Asn Ala Ala Gln Ala Ala Ala Ser Ile Gly Ala
                        195                 200                 205
            Val Thr Gly Ala Asp Ile Leu Gln Ala Ile Val Gln Ser Lys Glu Asn
                        210                 215                 220
            Pro Val Ala Asn Ser Thr Asp Gly Ile Glu Lys Ala Thr Asp Ala Ala
            225                 230                 235                 240
            Glu Ile Ala Val Ala Pro Ala Lys Asp Asn Lys Lys Glu Ile Lys Asp
                        245                 250                 255
            Gly Ala Lys Lys Asp Ala Val Ile Ala Ala Gly Ile Ala Leu Arg Ala
                        260                 265                 270
            Met Ala Lys Asn Gly Thr Phe Ser Ile Lys Asn Asn Glu Asp Ala Ala
                        275                 280                 285
            Val Thr Thr Ile Asn Ser Ala Ala Ala Ser Ala Val Asn Lys Ile Leu
                        290                 295                 300
            Ser Thr Leu Ile Ile Ala Ile Arg Asn Thr Val Asp Ser Gly Leu Lys
            305                 310                 315                 320
            Thr Ile Asn Glu Ala Leu Ala Thr Val Lys Gln Glu Asp Lys Ser Val
                        325                 330                 335
            Glu Ala Thr Asn Thr Ala Glu Ala Thr Thr Ser Gly Gln Gln Ala Lys
                        340                 345                 350
            Asn

<210> SEQ ID NO 5
<211> LENGTH: 416
<212> TYPE: DNA
<213> ORGANISM: Borrelia afzelii
<220> FEATURE:
<221> NAME/KEY: CDS
<222> LOCATION: (1)..(414)

<400> SEQUENCE: 5 aag ggg att gcg aag ggg ata aag ggg att gtt gcg gct gct ggg aag         48
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Lys | Gly | Ile | Ala | Lys | Gly | Ile | Lys | Gly | Ile | Val | Ala | Ala | Ala | Gly | Lys | |
| 1 | | | | 5 | | | | | 10 | | | | | 15 | | |

```
gct ttt ggc aag gat ggt gat gcg ctg aca ggt gtt gca aaa gct gct       96
Ala Phe Gly Lys Asp Gly Asp Ala Leu Thr Gly Val Ala Lys Ala Ala
             20                  25                  30 gag aat gat gct aac aag gat gcg ggg aag ttg ttt gct ggt aag aat      144
Glu Asn Asp Ala Asn Lys Asp Ala Gly Lys Leu Phe Ala Gly Lys Asn
         35                  40                  45 ggt aat gct ggt gct gct gac att gcg aag gcg gct gct gtt act          192
Gly Asn Ala Gly Ala Ala Asp Ile Ala Lys Ala Ala Ala Val Thr
     50                  55                  60 gcg gtt agt ggg gag cag ata cta aaa gct att gtt gag gcg gct ggt      240
Ala Val Ser Gly Glu Gln Ile Leu Lys Ala Ile Val Glu Ala Ala Gly
 65                  70                  75                  80 gat gcg gat cag gcg ggt gta aag gct gat gcg gct aag aat ccg att      288
Asp Ala Asp Gln Ala Gly Val Lys Ala Asp Ala Ala Lys Asn Pro Ile
                 85                  90                  95 gca gct gcg att ggg act gct gat gat ggt gct gcg ttt ggt aag gat      336
Ala Ala Ala Ile Gly Thr Ala Asp Asp Gly Ala Ala Phe Gly Lys Asp
             100                 105                 110 gag atg aag aag aga aat gat aag att gtt gca gct att gtt ttg agg      384
Glu Met Lys Lys Arg Asn Asp Lys Ile Val Ala Ala Ile Val Leu Arg
         115                 120                 125 ggg gtg cct aag gat gga aag ttt gct gct aa                           416
Gly Val Pro Lys Asp Gly Lys Phe Ala Ala
     130                 135
```

```
<210> SEQ ID NO 6
<211> LENGTH: 138
<212> TYPE: PRT
<213> ORGANISM: Borrelia afzelii

<400> SEQUENCE: 6
```

|     |     |     |     |     |     |     |     |     |     |     |     |     |     |     |     |
| --- | --- | --- | --- | --- | --- | --- | --- | --- | --- | --- | --- | --- | --- | --- | --- |
| Lys | Gly | Ile | Ala | Lys | Gly | Ile | Lys | Gly | Ile | Val | Ala | Ala | Ala | Gly | Lys |
| 1 | | | | 5 | | | | | 10 | | | | | 15 | |
| Ala | Phe | Gly | Lys | Asp | Gly | Asp | Ala | Leu | Thr | Gly | Val | Ala | Lys | Ala | Ala |
| | | | 20 | | | | | 25 | | | | | 30 | | |
| Glu | Asn | Asp | Ala | Asn | Lys | Asp | Ala | Gly | Lys | Leu | Phe | Ala | Gly | Lys | Asn |
| | | 35 | | | | | 40 | | | | | 45 | | | |
| Gly | Asn | Ala | Gly | Ala | Ala | Asp | Ile | Ala | Lys | Ala | Ala | Ala | Val | Thr | |
| | 50 | | | | | 55 | | | | | 60 | | | | |
| Ala | Val | Ser | Gly | Glu | Gln | Ile | Leu | Lys | Ala | Ile | Val | Glu | Ala | Ala | Gly |
| 65 | | | | | 70 | | | | | 75 | | | | | 80 |
| Asp | Ala | Asp | Gln | Ala | Gly | Val | Lys | Ala | Asp | Ala | Ala | Lys | Asn | Pro | Ile |
| | | | | 85 | | | | | 90 | | | | | 95 | |
| Ala | Ala | Ala | Ile | Gly | Thr | Ala | Asp | Asp | Gly | Ala | Ala | Phe | Gly | Lys | Asp |
| | | | 100 | | | | | 105 | | | | | 110 | | |
| Glu | Met | Lys | Lys | Arg | Asn | Asp | Lys | Ile | Val | Ala | Ala | Ile | Val | Leu | Arg |
| | | 115 | | | | | 120 | | | | | 125 | | | |
| Gly | Val | Pro | Lys | Asp | Gly | Lys | Phe | Ala | Ala | | | | | | |
| | 130 | | | | | 135 | | | | | | | | | |

```
<210> SEQ ID NO 7
<211> LENGTH: 413
<212> TYPE: DNA
<213> ORGANISM: Borrelia afzelii
<220> FEATURE:
<221> NAME/KEY: CDS
<222> LOCATION: (1)..(411)
```

```
<400> SEQUENCE: 7 aag ggg att gcg aag ggg ata aag ggg att gtt gat gct gct ggg aag    48
Lys Gly Ile Ala Lys Gly Ile Lys Gly Ile Val Asp Ala Ala Gly Lys
1               5                   10                  15 gct ttt ggc aag gag ggt agt gcg ctg aag gat gtt gca aaa gtt gct    96
Ala Phe Gly Lys Glu Gly Ser Ala Leu Lys Asp Val Ala Lys Val Ala
            20                  25                  30 gat gat gat aac aag gat gcg ggg aag ttg ttt gct ggt aag aat ggt   144
Asp Asp Asp Asn Lys Asp Ala Gly Lys Leu Phe Ala Gly Lys Asn Gly
        35                  40                  45 ggt gct ggt gct gct gat gcg att ggg aag gcg gct gct gtt act       192
Gly Ala Gly Ala Ala Asp Ala Ile Gly Lys Ala Ala Ala Val Thr
    50                  55                  60 gcg gtt agt ggg gag cag ata ctg aaa gct att gtt gat gct gct ggt   240
Ala Val Ser Gly Glu Gln Ile Leu Lys Ala Ile Val Asp Ala Ala Gly
65                  70                  75                  80 gct gca gct aat cag gcg ggt aaa aag gct gcg gat gct aag aat ccg   288
Ala Ala Ala Asn Gln Ala Gly Lys Lys Ala Ala Asp Ala Lys Asn Pro
                85                  90                  95 att gcg gct gcg att ggg act gct gat gat ggg gcg gag ttt aag gat   336
Ile Ala Ala Ala Ile Gly Thr Ala Asp Asp Gly Ala Glu Phe Lys Asp
            100                 105                 110 gat atg aag aag agt gat aat att gct gcg gct att gtt ttg agg ggg   384
Asp Met Lys Lys Ser Asp Asn Ile Ala Ala Ala Ile Val Leu Arg Gly
        115                 120                 125 gtg cct aag gat gga aag ttt gct gct aa                            413
Val Pro Lys Asp Gly Lys Phe Ala Ala
    130                 135

<210> SEQ ID NO 8
<211> LENGTH: 137
<212> TYPE: PRT
<213> ORGANISM: Borrelia afzelii

<400> SEQUENCE: 8

Lys Gly Ile Ala Lys Gly Ile Lys Gly Ile Val Asp Ala Ala Gly Lys
1               5                   10                  15

Ala Phe Gly Lys Glu Gly Ser Ala Leu Lys Asp Val Ala Lys Val Ala
            20                  25                  30

Asp Asp Asp Asn Lys Asp Ala Gly Lys Leu Phe Ala Gly Lys Asn Gly
        35                  40                  45

Gly Ala Gly Ala Ala Asp Ala Ile Gly Lys Ala Ala Ala Val Thr
    50                  55                  60

Ala Val Ser Gly Glu Gln Ile Leu Lys Ala Ile Val Asp Ala Ala Gly
65                  70                  75                  80

Ala Ala Ala Asn Gln Ala Gly Lys Lys Ala Ala Asp Ala Lys Asn Pro
                85                  90                  95

Ile Ala Ala Ala Ile Gly Thr Ala Asp Asp Gly Ala Glu Phe Lys Asp
            100                 105                 110

Asp Met Lys Lys Ser Asp Asn Ile Ala Ala Ala Ile Val Leu Arg Gly
        115                 120                 125

Val Pro Lys Asp Gly Lys Phe Ala Ala
    130                 135

<210> SEQ ID NO 9
<211> LENGTH: 428
<212> TYPE: DNA
<213> ORGANISM: Borrelia afzelii
<220> FEATURE:
```

```
<221> NAME/KEY: CDS
<222> LOCATION: (1)..(426)

<400> SEQUENCE: 9 aag ggg att gcg aag ggg ata aag ggg att gtt gat gct gct ggg aag      48
Lys Gly Ile Ala Lys Gly Ile Lys Gly Ile Val Asp Ala Ala Gly Lys
1               5                   10                  15 gct ttt ggt aag gag ggt gat gcg ctg aag gat gtt gca aaa gtt gct      96
Ala Phe Gly Lys Glu Gly Asp Ala Leu Lys Asp Val Ala Lys Val Ala
            20                  25                  30 gat gag aat ggg gat aac aag gat gcg ggg aag ttg ttt gct ggt gag     144
Asp Glu Asn Gly Asp Asn Lys Asp Ala Gly Lys Leu Phe Ala Gly Glu
        35                  40                  45 aat ggt aat gct ggt ggt gct gct gat gct gac att gcg aag gcg gct     192
Asn Gly Asn Ala Gly Gly Ala Ala Asp Ala Asp Ile Ala Lys Ala Ala
    50                  55                  60 gct gct gtt act gcg gtt agt ggg gag cag ata ctg aaa gct att gtt     240
Ala Ala Val Thr Ala Val Ser Gly Glu Gln Ile Leu Lys Ala Ile Val
65                  70                  75                  80 gag gcg gct ggt gct gcg gat cag gcg ggt gta aag gct gag gag gct     288
Glu Ala Ala Gly Ala Ala Asp Gln Ala Gly Val Lys Ala Glu Glu Ala
                85                  90                  95 aag aat ccg att gca gct gcg att ggg act gat gat gct ggt gcg gcg     336
Lys Asn Pro Ile Ala Ala Ala Ile Gly Thr Asp Asp Ala Gly Ala Ala
            100                 105                 110 gag ttt ggt gag aat gat atg aag aag aat gat aat att gct gcg gct     384
Glu Phe Gly Glu Asn Asp Met Lys Lys Asn Asp Asn Ile Ala Ala Ala
        115                 120                 125 att gtt ttg agg ggg gtg cct aag gat gga aag ttt gct gct aa          428
Ile Val Leu Arg Gly Val Pro Lys Asp Gly Lys Phe Ala Ala
    130                 135                 140

<210> SEQ ID NO 10
<211> LENGTH: 142
<212> TYPE: PRT
<213> ORGANISM: Borrelia afzelii

<400> SEQUENCE: 10

Lys Gly Ile Ala Lys Gly Ile Lys Gly Ile Val Asp Ala Ala Gly Lys
1               5                   10                  15

Ala Phe Gly Lys Glu Gly Asp Ala Leu Lys Asp Val Ala Lys Val Ala
            20                  25                  30

Asp Glu Asn Gly Asp Asn Lys Asp Ala Gly Lys Leu Phe Ala Gly Glu
        35                  40                  45

Asn Gly Asn Ala Gly Gly Ala Ala Asp Ala Asp Ile Ala Lys Ala Ala
    50                  55                  60

Ala Ala Val Thr Ala Val Ser Gly Glu Gln Ile Leu Lys Ala Ile Val
65                  70                  75                  80

Glu Ala Ala Gly Ala Ala Asp Gln Ala Gly Val Lys Ala Glu Glu Ala
                85                  90                  95

Lys Asn Pro Ile Ala Ala Ala Ile Gly Thr Asp Asp Ala Gly Ala Ala
            100                 105                 110

Glu Phe Gly Glu Asn Asp Met Lys Lys Asn Asp Asn Ile Ala Ala Ala
        115                 120                 125

Ile Val Leu Arg Gly Val Pro Lys Asp Gly Lys Phe Ala Ala
    130                 135                 140

<210> SEQ ID NO 11
<211> LENGTH: 426
```

<212> TYPE: DNA
<213> ORGANISM: Borrelia afzelii
<220> FEATURE:
<221> NAME/KEY: CDS
<222> LOCATION: (3)..(425)

<400> SEQUENCE: 11

```
ag ggg att gcg aag ggg ata aag ggg att gtt gat gct gct ggg aag        47
   Gly Ile Ala Lys Gly Ile Lys Gly Ile Val Asp Ala Ala Gly Lys
   1               5                   10                  15 gct ttt ggc aag gag ggt agt gcg ctg aag gat gtt aaa aca gtt gct       95
Ala Phe Gly Lys Glu Gly Ser Ala Leu Lys Asp Val Lys Thr Val Ala
                20                  25                  30 gct gag aat gag gct aac aag gat gcg ggg aag ttg ttt gct ggt aag      143
Ala Glu Asn Glu Ala Asn Lys Asp Ala Gly Lys Leu Phe Ala Gly Lys
            35                  40                  45 aat ggt aat gct gat gct gct gat gct gct gac att gcg aag gcg gct      191
Asn Gly Asn Ala Asp Ala Ala Asp Ala Ala Asp Ile Ala Lys Ala Ala
        50                  55                  60 ggt gct gtt agt gcg gtt agt ggg gag cag ata ctg aaa gct att gtt      239
Gly Ala Val Ser Ala Val Ser Gly Glu Gln Ile Leu Lys Ala Ile Val
65                  70                  75 gat ggt gct ggt gat gca gct aat cag gcg ggt aaa aag gct gct gag      287
Asp Gly Ala Gly Asp Ala Ala Asn Gln Ala Gly Lys Lys Ala Ala Glu
80                  85                  90                  95 gct aag aat ccg att gcg gct gcg att ggg act aat gaa gct ggg gcg      335
Ala Lys Asn Pro Ile Ala Ala Ala Ile Gly Thr Asn Glu Ala Gly Ala
                100                 105                 110 gag ttt ggt gat gat atg aag aag aga aat gat aag att gct gcg gct      383
Glu Phe Gly Asp Asp Met Lys Lys Arg Asn Asp Lys Ile Ala Ala Ala
            115                 120                 125 att gtt ttg agg ggg gtg cct aag gat gga aag ttt gct gct a            426
Ile Val Leu Arg Gly Val Pro Lys Asp Gly Lys Phe Ala Ala
        130                 135                 140
```

<210> SEQ ID NO 12
<211> LENGTH: 141
<212> TYPE: PRT
<213> ORGANISM: Borrelia afzelii

<400> SEQUENCE: 12

```
Gly Ile Ala Lys Gly Ile Lys Gly Ile Val Asp Ala Ala Gly Lys Ala
1               5                   10                  15

Phe Gly Lys Glu Gly Ser Ala Leu Lys Asp Val Lys Thr Val Ala Ala
                20                  25                  30

Glu Asn Glu Ala Asn Lys Asp Ala Gly Lys Leu Phe Ala Gly Lys Asn
            35                  40                  45

Gly Asn Ala Asp Ala Ala Asp Ala Ala Asp Ile Ala Lys Ala Ala Gly
        50                  55                  60

Ala Val Ser Ala Val Ser Gly Glu Gln Ile Leu Lys Ala Ile Val Asp
65                  70                  75                  80

Gly Ala Gly Asp Ala Ala Asn Gln Ala Gly Lys Lys Ala Ala Glu Ala
                85                  90                  95

Lys Asn Pro Ile Ala Ala Ala Ile Gly Thr Asn Glu Ala Gly Ala Glu
                100                 105                 110

Phe Gly Asp Asp Met Lys Lys Arg Asn Asp Lys Ile Ala Ala Ala Ile
            115                 120                 125

Val Leu Arg Gly Val Pro Lys Asp Gly Lys Phe Ala Ala
        130                 135                 140
```

<210> SEQ ID NO 13
<211> LENGTH: 396
<212> TYPE: DNA
<213> ORGANISM: Borrelia garinii
<220> FEATURE:
<221> NAME/KEY: CDS
<222> LOCATION: (2)..(394)

<400> SEQUENCE: 13

```
g ggg ata aag ggg att gtt gat gct gct gag aag gct gat gcg aag gaa    49
  Gly Ile Lys Gly Ile Val Asp Ala Ala Glu Lys Ala Asp Ala Lys Glu
  1               5                  10                  15 ggg aag ttg aat gct gct ggt gct gag ggt acg act aac gcg gat gct    97
Gly Lys Leu Asn Ala Ala Gly Ala Glu Gly Thr Thr Asn Ala Asp Ala
             20                  25                  30 ggg aag ttg ttt gtg aag aat gct ggt aat gtg ggt ggt gaa gca ggt   145
Gly Lys Leu Phe Val Lys Asn Ala Gly Asn Val Gly Gly Glu Ala Gly
         35                  40                  45 gat gct ggg aag gct gct gct gcg gtt gct gct gtt agt ggg gag cag   193
Asp Ala Gly Lys Ala Ala Ala Ala Val Ala Ala Val Ser Gly Glu Gln
50                  55                  60 ata tta aaa gcg att gtt gat gct gct aag gat ggt ggt gag aag cag   241
Ile Leu Lys Ala Ile Val Asp Ala Ala Lys Asp Gly Gly Glu Lys Gln
65                  70                  75                  80 ggt aag aag gct gcg gat gct aca aat ccg att gag gcg gct att ggg   289
Gly Lys Lys Ala Ala Asp Ala Thr Asn Pro Ile Glu Ala Ala Ile Gly
                 85                  90                  95 ggt gcg ggt gat aat gat gct gct gcg gcg ttt gct act atg aag aag   337
Gly Ala Gly Asp Asn Asp Ala Ala Ala Ala Phe Ala Thr Met Lys Lys
            100                 105                 110 gat gat cag att gct gct gct atg gtt ctg agg gga atg gct aag gat   385
Asp Asp Gln Ile Ala Ala Ala Met Val Leu Arg Gly Met Ala Lys Asp
        115                 120                 125 ggg cag ttt gc                                                    396
Gly Gln Phe
    130
```

<210> SEQ ID NO 14
<211> LENGTH: 131
<212> TYPE: PRT
<213> ORGANISM: Borrelia garinii

<400> SEQUENCE: 14

```
Gly Ile Lys Gly Ile Val Asp Ala Ala Glu Lys Ala Asp Ala Lys Glu
1               5                  10                  15

Gly Lys Leu Asn Ala Ala Gly Ala Glu Gly Thr Thr Asn Ala Asp Ala
            20                  25                  30

Gly Lys Leu Phe Val Lys Asn Ala Gly Asn Val Gly Gly Glu Ala Gly
        35                  40                  45

Asp Ala Gly Lys Ala Ala Ala Ala Val Ala Ala Val Ser Gly Glu Gln
    50                  55                  60

Ile Leu Lys Ala Ile Val Asp Ala Ala Lys Asp Gly Gly Glu Lys Gln
65                  70                  75                  80

Gly Lys Lys Ala Ala Asp Ala Thr Asn Pro Ile Glu Ala Ala Ile Gly
                85                  90                  95

Gly Ala Gly Asp Asn Asp Ala Ala Ala Ala Phe Ala Thr Met Lys Lys
            100                 105                 110

Asp Asp Gln Ile Ala Ala Ala Met Val Leu Arg Gly Met Ala Lys Asp
        115                 120                 125
```

-continued

```
Gly Gln Phe
        130

<210> SEQ ID NO 15
<211> LENGTH: 390
<212> TYPE: DNA
<213> ORGANISM: Borrelia garinii
<220> FEATURE:
<221> NAME/KEY: CDS
<222> LOCATION: (2)..(388)

<400> SEQUENCE: 15 g ggg ata aag ggg att gtt gat gct gct gag aag gct gat gcg aag gaa        49
  Gly Ile Lys Gly Ile Val Asp Ala Ala Glu Lys Ala Asp Ala Lys Glu
  1               5                  10                  15 ggg aag ttg gat gtg gct ggt gat gct ggt gaa act aac aag gat gct          97
Gly Lys Leu Asp Val Ala Gly Asp Ala Gly Glu Thr Asn Lys Asp Ala
            20                  25                  30 ggg aag ttg ttt gtg aag aag aat aat gag ggt ggt gaa gca aat gat         145
Gly Lys Leu Phe Val Lys Lys Asn Asn Glu Gly Gly Glu Ala Asn Asp
        35                  40                  45 gct ggg aag gct gct gct gcg gtt gct gct gtt agt ggg gag cag ata         193
Ala Gly Lys Ala Ala Ala Ala Val Ala Ala Val Ser Gly Glu Gln Ile
    50                  55                  60 tta aaa gcg att gtt gat gct gct gag ggt ggt gag aag cag ggt aag         241
Leu Lys Ala Ile Val Asp Ala Ala Glu Gly Gly Glu Lys Gln Gly Lys
65                  70                  75                  80 aag gct gcg gat gct aca aat ccg att gag gcg gct att ggg ggt gcg         289
Lys Ala Ala Asp Ala Thr Asn Pro Ile Glu Ala Ala Ile Gly Gly Ala
                85                  90                  95 ggt gat aat gat gct gct gcg gcg ttt gct act atg aag aag gat gat         337
Gly Asp Asn Asp Ala Ala Ala Ala Phe Ala Thr Met Lys Lys Asp Asp
            100                 105                 110 cag att gct act gct atg gtt ctg agg gga atg gct aag gat ggg cag         385
Gln Ile Ala Thr Ala Met Val Leu Arg Gly Met Ala Lys Asp Gly Gln
        115                 120                 125 ttt gc                                                                  390
Phe

<210> SEQ ID NO 16
<211> LENGTH: 129
<212> TYPE: PRT
<213> ORGANISM: Borrelia garinii

<400> SEQUENCE: 16

Gly Ile Lys Gly Ile Val Asp Ala Ala Glu Lys Ala Asp Ala Lys Glu
1               5                  10                  15

Gly Lys Leu Asp Val Ala Gly Asp Ala Gly Glu Thr Asn Lys Asp Ala
            20                  25                  30

Gly Lys Leu Phe Val Lys Lys Asn Asn Glu Gly Gly Glu Ala Asn Asp
        35                  40                  45

Ala Gly Lys Ala Ala Ala Ala Val Ala Ala Val Ser Gly Glu Gln Ile
    50                  55                  60

Leu Lys Ala Ile Val Asp Ala Ala Glu Gly Gly Glu Lys Gln Gly Lys
65                  70                  75                  80

Lys Ala Ala Asp Ala Thr Asn Pro Ile Glu Ala Ala Ile Gly Gly Ala
                85                  90                  95

Gly Asp Asn Asp Ala Ala Ala Ala Phe Ala Thr Met Lys Lys Asp Asp
            100                 105                 110

Gln Ile Ala Thr Ala Met Val Leu Arg Gly Met Ala Lys Asp Gly Gln
```

```
<210> SEQ ID NO 17
<211> LENGTH: 390
<212> TYPE: DNA
<213> ORGANISM: Borrelia garinii
<220> FEATURE:
<221> NAME/KEY: CDS
<222> LOCATION: (2)..(388)

<400> SEQUENCE: 17 g ggg ata aag ggg att gtt gat gct gct gag aag gct gat gcg aag gaa        49
  Gly Ile Lys Gly Ile Val Asp Ala Ala Glu Lys Ala Asp Ala Lys Glu
  1               5                  10                  15 ggg agg ttg gat gtg gct ggt gat gct ggt gaa act aac aag gat gct         97
Gly Arg Leu Asp Val Ala Gly Asp Ala Gly Glu Thr Asn Lys Asp Ala
             20                  25                  30 ggg aag ttg ttt gtg aag aag aat aat gag ggt ggt gaa gca aat gat        145
Gly Lys Leu Phe Val Lys Lys Asn Asn Glu Gly Gly Glu Ala Asn Asp
         35                  40                  45 gct ggg aag gct gct gct gcg gtt gct gct gtt agt ggg gag cag ata        193
Ala Gly Lys Ala Ala Ala Ala Val Ala Ala Val Ser Gly Glu Gln Ile
 50                  55                  60 tta aaa gcg att gtt gat gct gct gag ggt ggt gag aag cag ggt aag        241
Leu Lys Ala Ile Val Asp Ala Ala Glu Gly Gly Glu Lys Gln Gly Lys
65                  70                  75                  80 aag gct gcg gat gct aca aat ccg att gag gcg gct att ggg ggt gcg        289
Lys Ala Ala Asp Ala Thr Asn Pro Ile Glu Ala Ala Ile Gly Gly Ala
                 85                  90                  95 ggt gat aat gat gct gct gcg gcg ttt gct act atg aag aag gat gat        337
Gly Asp Asn Asp Ala Ala Ala Ala Phe Ala Thr Met Lys Lys Asp Asp
            100                 105                 110 cag att gct gct gct atg gtt ctg agg gga atg gct aag gat ggg cag        385
Gln Ile Ala Ala Ala Met Val Leu Arg Gly Met Ala Lys Asp Gly Gln
        115                 120                 125 ttt gc                                                                  390
Phe

<210> SEQ ID NO 18
<211> LENGTH: 129
<212> TYPE: PRT
<213> ORGANISM: Borrelia garinii

<400> SEQUENCE: 18

Gly Ile Lys Gly Ile Val Asp Ala Ala Glu Lys Ala Asp Ala Lys Glu
1               5                  10                  15

Gly Arg Leu Asp Val Ala Gly Asp Ala Gly Glu Thr Asn Lys Asp Ala
             20                  25                  30

Gly Lys Leu Phe Val Lys Lys Asn Asn Glu Gly Gly Glu Ala Asn Asp
         35                  40                  45

Ala Gly Lys Ala Ala Ala Ala Val Ala Ala Val Ser Gly Glu Gln Ile
 50                  55                  60

Leu Lys Ala Ile Val Asp Ala Ala Glu Gly Gly Glu Lys Gln Gly Lys
65                  70                  75                  80

Lys Ala Ala Asp Ala Thr Asn Pro Ile Glu Ala Ala Ile Gly Gly Ala
                 85                  90                  95

Gly Asp Asn Asp Ala Ala Ala Ala Phe Ala Thr Met Lys Lys Asp Asp
            100                 105                 110
```

```
Gln Ile Ala Ala Ala Met Val Leu Arg Gly Met Ala Lys Asp Gly Gln
            115                 120                 125

Phe

<210> SEQ ID NO 19
<211> LENGTH: 339
<212> TYPE: DNA
<213> ORGANISM: Borrelia garinii
<220> FEATURE:
<221> NAME/KEY: CDS
<222> LOCATION: (2)..(337)

<400> SEQUENCE: 19 g ggg ata aag ggg att gtt gat gct gct ggt gaa act aac aag gat gct        49
  Gly Ile Lys Gly Ile Val Asp Ala Ala Gly Glu Thr Asn Lys Asp Ala
  1               5                  10                  15 ggg aag ttg ttt gtg aag aag aat aat gag ggt ggt gaa gca aat gat         97
Gly Lys Leu Phe Val Lys Lys Asn Asn Glu Gly Gly Glu Ala Asn Asp
            20                  25                  30 gct ggg aag gct gct gct gcg gtt gct gct gtt agt ggg gag cag ata        145
Ala Gly Lys Ala Ala Ala Ala Val Ala Ala Val Ser Gly Glu Gln Ile
        35                  40                  45 tta aaa gcg att gtt gat gct gct gag ggt ggt gag aag cag ggt aag        193
Leu Lys Ala Ile Val Asp Ala Ala Glu Gly Gly Glu Lys Gln Gly Lys
 50                  55                  60 aag gct gcg gat gct aca aat ccg att gag gcg gct att ggg ggt aca        241
Lys Ala Ala Asp Ala Thr Asn Pro Ile Glu Ala Ala Ile Gly Gly Thr
 65                  70                  75                  80 aat gat aat gat gct gcg gcg ttt gct act atg aag aag gat gat cag        289
Asn Asp Asn Asp Ala Ala Ala Phe Ala Thr Met Lys Lys Asp Asp Gln
                 85                  90                  95 att gct gct gct atg gtt ctg agg gga atg gct aag gat ggg cag ttt        337
Ile Ala Ala Ala Met Val Leu Arg Gly Met Ala Lys Asp Gly Gln Phe
            100                 105                 110 gc                                                                      339

<210> SEQ ID NO 20
<211> LENGTH: 112
<212> TYPE: PRT
<213> ORGANISM: Borrelia garinii

<400> SEQUENCE: 20

Gly Ile Lys Gly Ile Val Asp Ala Ala Gly Glu Thr Asn Lys Asp Ala
1               5                  10                  15

Gly Lys Leu Phe Val Lys Lys Asn Asn Glu Gly Gly Glu Ala Asn Asp
            20                  25                  30

Ala Gly Lys Ala Ala Ala Ala Val Ala Ala Val Ser Gly Glu Gln Ile
        35                  40                  45

Leu Lys Ala Ile Val Asp Ala Ala Glu Gly Gly Glu Lys Gln Gly Lys
 50                  55                  60

Lys Ala Ala Asp Ala Thr Asn Pro Ile Glu Ala Ala Ile Gly Gly Thr
 65                  70                  75                  80

Asn Asp Asn Asp Ala Ala Ala Phe Ala Thr Met Lys Lys Asp Asp Gln
                 85                  90                  95

Ile Ala Ala Ala Met Val Leu Arg Gly Met Ala Lys Asp Gly Gln Phe
            100                 105                 110

<210> SEQ ID NO 21
<211> LENGTH: 21
<212> TYPE: DNA
```

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic Primer

<400> SEQUENCE: 21
ccagcaaaca acttccccgc c          21

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic Primer

<400> SEQUENCE: 22
atccttaaac tccgcccat catc          24

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic Primer

<400> SEQUENCE: 23
gagtgctgtg gagagtgctg ttgatgag          28

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic Primer

<400> SEQUENCE: 24
ggggataaag gggattgttg atgctgc          27

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic Primer

<400> SEQUENCE: 25
gcaaactgcc catccttagc cattcc          26

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic Primer

<400> SEQUENCE: 26
aaggggattg cgaaggggat aaagg          25

<210> SEQ ID NO 27
<211> LENGTH: 27
<212> TYPE: DNA
<213> ORGANISM: Artificial Sequence

```
<220> FEATURE:
<223> OTHER INFORMATION: Description of Artificial Sequence:  Synthetic
      Primer

<400> SEQUENCE: 27
ttagcagcaa actttccatc cttagcc                                         27

<210> SEQ ID NO 28
<211> LENGTH: 5897
<212> TYPE: DNA
<213> ORGANISM: Borrelia garinii

<400> SEQUENCE: 28
cggaaatcaa gccacctaaa acaacttccc aaaagtttct caaaaaatat tatattcagc     60
agtaaattct ataagtcatt aattatttaa tactattcaa cagtaaattc tataagtcat    120
taattattta atactattca gcagtaaatt ctataagtca ttaattatt t aatactattc   180 agcagtaaat tctataagtc attaattatt taatactatt cagcagtaaa ttctataagt   240
cattaattat ttaatactat tcagcagtaa attctataag tcattaatta tttaatacta   300
ttcagcagta aattctataa gtcattaatt caattaggta acggattctt agatgtattc   360
acctcttttg gtggattagt tgcagatgca ttggggttta aagctgatcc aaaaaaatct   420
gatgtaaaaa cttatttga atctctagct aaaaaattag aagaaacaaa agatggttta    480
actaagttgt ccaaaggtaa tgacggtgat actggaaagg ctggtgatgc tggtggggct   540
ggtggtggcg ctagtgctgc aggtggcgct ggtgggattg agggcgctat aacagagatt   600
agcaaatggt tagatgatat ggcaaaagct gctgcggaag ctgcaagtgc tgctactggt   660
aatgcagcaa ttggggatgt tgttaatggt aatggtggag cagcaaaagg tggtgatgcg   720
gagagtgtta atgggattgc taaggggata aaggggattg ttgatgctgc tgagaaggct   780
gatgcgaagg aagggaagtt ggatgtggct ggtgatgctg gtgggctgg tggtggcgct    840 ggtgctgcag gtgcgctgg tgggattgag gcgctataa cagagattag caaatggtta    900
gatgatatgg caaaagctgc tgcggttgct gcaagtgctg caagtgctgc tactggtaat   960
gcagcaattg gggatgttgt taatggtaat gatggagcag caaaaggtgg tgatgcggcg  1020
agtgttaatg ggattgctaa ggggataaag gggattgttg atgctgctga aaggctgat   1080 gcgaaggaag ggaagttgga tgtggctggt gatgctggtg agggtaacaa ggatgctggg  1140
aagctgtttg tgaagaagaa tgctggtgat gagggtggtg aagcaaatga tgctgggaag  1200
gctgctgctg cggttgctgc tgttagtggg gagcagatat taaaagcgat tgttgatgct  1260
gctgagggtg atgataagca gggtaagaag gctgcggatg ctacaaatcc gattgaggcg  1320
gctattgggg gtgcggatgc gggtgctaat gctgaggcgt taataagat gaagaaggat   1380 gatcagattg ctgctgctat ggttctgagg ggaatggcta aggatgggca gtttgctttg  1440
aaggatgatg ctgctgctca tgaagggact gttaagaatg ctgttgatat ggcaaaggcc  1500
gctgcggaag ctgcaagtgc tgcaagtgct gctactggta gtacaacgat tggagatgtt  1560
gttaagagtg gtgaggcaaa agatggtgat gcggcgagtg ttaatgggat tgctaagggg  1620
ataaagggga ttgttgatgc tgctgagaag gctgatgcga aggaaggaa gttggatgtg   1680 gctggtgctg ctggtacgac taacgtgaat gttgggaagt tgtttgtgaa gaataatggt   1740
aatgagggtg gtgatgcaag tgatgctggg aaagctgctg ctgcggttgc tgctgttagt   1800
ggggagcaga tattaaaagc gattgttgat gctgctaaag atggtgataa gcaggggtt   1860 actgatgtaa aggatgctac aaatccgatt gaggcggcta ttgggggtac aaatgataat  1920
```

```
gatgctgcgg cgtttgctac tatgaagaag gatgatcaga ttgctgctgc tatggttctg   1980
aggggaatgg ctaaggatgg gcagtttgct ttgaaggatg atgctgctaa ggatggtgat   2040
aaaacggggg ttgctgcgga tgctgaaaat ccgattgacg cggctattgg gggtgcggat   2100
gctgatgctg cggcgtttaa taaggagggg atgaagaagg atgatcagat tgctgctgct   2160
atggttctga ggggaatggc taaggatggg cagtttgctt tgacgaataa tgctgctgct   2220
catgaaggga ctgttaagaa tgctgttgat atggcaaaag ctgctgcggt tgctgcaagt   2280
gctgctactg gcaatgcagc aattggggat gttgttaaga gtaatggtgg agcagcagca   2340
aaaggtggtg atgcggcgag tgttaatggg attgctaagg gataaaggg gattgttgat    2400 gctgctgaga aggctgatgc gaaggaaggg aagttggatg tggctggtgc tgctggtgaa   2460
actaacaagg atgctgggaa gttgtttgtg aagaagaatg gtgatgatgg tggtgatgca   2520
ggtgatgctg ggaaggctgc tgctgcggtt gctgctgtta gtggggagca gatattaaaa   2580
gcgattgttg atgctgctaa agatggtgat aagacggggg ttactgatgt aaaggatgct   2640
acaaatccga ttgacgcggc tattgggggg agtgcggatg ctaatgctga ggcgtttgat   2700
aagatgaaga aggatgatca gattgctgct gctatggttc tgaggggaat ggctaaggat   2760
gggcagtttg ctttgaagaa taatgatcat gataatcata aggggactgt taagaatgct   2820
gttgatatgg caaaggccgc tgaggaagct gcaagtgctg caagtgctgc tactggtaat   2880
gcagcgattg gggatgttgt taagaatagt ggggcagcag caaaaggtgg tgaggcggcg   2940
agtgttaatg ggattgctaa ggggataaag gggattgttg atgctgctgg aaaggctgat   3000
gcgaaggaag ggaagttgga tgctactggt gctgagggta cgactaacgt gaatgctggg   3060
aagttgtttg tgaagagggc ggctgatgat ggtggtgatg cagatgatgc tgggaaggct   3120
gctgctgcgg ttgctgcaag tgctgctact ggtaatgcag cgattggaga tgttgttaat   3180
ggtgatgtgg caaaagcaaa aggtggtgat gcggcgagtg ttaatgggat tgctaagggg   3240
ataaagggga ttgttgatgc tgctgagaag gctgatgcga aggaagggaa gttgaatgct   3300
gctggtgctg agggtacgac taacgcggat gctgggaagt tgtttgtgaa gaatgctggt   3360
aatgtgggtg gtgaagcagg tgatgctggg aaggctgctc tgcggttgc tgctgttagt    3420 ggggagcaga tattaaaagc gattgttgat gctgctaagg atggtggtga aagcagggt    3480 aagaaggctg cggatgctac aaatccgatt gacgcggcta ttgggggtac aaatgataat   3540
gatgctgctg cggcgtttgc tactatgaag aaggatgatc agattgctgc tgctatggtt   3600
ctgaggggaa tggctaagga tgggcaattt gctttgaagg atgctgctgc tgctcatgaa   3660
gggactgtta agaatgctgt tgatataata aaggctgctg cggaagctgc aagtgctgca   3720
agtgctgcta ctggtagtgc agcaattggg gatgttgtta atggtaatgg agcaacagca   3780
aaaggtggtg atgcgaagag tgttaatggg attgctaagg ggataaaggg gattgttgat   3840
gctgctgaga aggctgatgc gaaggaaggg aagttggatg tggctggtga tgctggtgaa   3900
actaacaagg atgctgggaa gttgtttgtg aagaacaatg gtaatgaggg tggtgatgca   3960
gatgatgctg ggaaggctgc tgctgcggtt gctgctgtta gtggggagca gatattaaaa   4020
gcgattgttg atgctgctaa gggtggtgat aagacgggta agaataatgt gaaggatgct   4080
gaaaatccga ttgaggcggc tattgggagt agtgcggatg ctgatgctgc ggcgtttaat   4140
aaggagggga tgaagaagga tgatcagatt gctgctgcta tggttctgag gggaatggct   4200
aaggatgggc agtttgcttt gacgaatgat gctgctgctc atgaagggac tgttaagaat   4260
```

```
gctgttggga gtgcaacaaa taagaccgtt gttgctttgg ctaacttggt tcgaaagacc    4320
gtgcaagctg ggttgaagaa ggttggggat gttgttaaga atagtgaggc aaaagatggt    4380
gatgcggcga gtgttaatgg gattgctaag gggataaagg ggattgttga tgctgctgag    4440
aaggctgatg cgaaggaagg gaagttggat gtggctggtg ctgctggtga aactaacaag    4500
gatgctggga agttgtttgt gaagaagaat aatgagggtg gtgaagcaaa tgatgctggg    4560
aaggctgctg ctgcggttgc tgctgttagt ggggagcaga tattaaaagc gattgttgat    4620
gctgctaagg atggtgatga taagcagggt aagaaggctg aggatgctac aaatccgatt    4680
gacgcggcta ttgggggtgc aggtgcgggt gctaatgctg ctgcggcgtt taataatatg    4740
aagaaggatg atcagattgc tgctgctatg gttctgaggg gaatggctaa ggatgggcag    4800
tttgctttga cgaataatgc tcatactaat cataagggga ctgttaagaa tgctgttgat    4860
atgacaaaag ctgctgcggt tgctgcaagt gctgcaagtg ctgctactgg taatgcagca    4920
attggggatg ttgttaatgg taatgatgga gcagcaaaag gtggtgatgc ggcgagtgtt    4980
aatgggattg ctaaggggat aaaggggatt gttgatgctg ctgagaaggc tgatgcgaag    5040
gaagggaagt tgaatgtggc tggtgctgct ggtgctgagg gtaacgaggc tgctgggaag    5100
ctgtttgtga agaagaatgc tggtgatcat ggtggtgaag caggtgatgc tgggagggct    5160
gctgctgcgg ttgctgctgt tagtggggag cagatattaa aagcgattgt tgatgctgct    5220
aaggatggtg tgataagca gggtaagaag gctgaggatc tgaaaatcc gattgacgcg    5280 gctattggga gtacgggtgc ggatgataat gctgctgagg cgtttgctac tatgaagaag    5340
gatgatcaga ttgctgctgc tatggttctg aggggaatgg ctaaggatgg gcagtttgct    5400
ttgaaggatg ctgctcatga taatcataag gggactgtta agaatgctgt tgatataata    5460
aaggctactg cggttgctgc aagtgctgct actggtagta caacgattgg ggatgttgtt    5520
aagaatggtg aggcaaaagg tggtgaggcg aagagtgtta atgggattgc taaggggata    5580
aaggggattg ttgatgctgc tggaaaggct gatgcgaagg aagggaagtt gaatgtggct    5640
ggtgctgctg gtgagggtaa cgaggctgct gggaagctgt ttgtgtaaat tactatagga    5700
ttagaactag tgtacgatat gagtcctttg gttattttgc agctgctaat gaatttgaaa    5760
taagtgaagt taaaattgcg gatgttaatg gaacacattt tattgctaca aaagagaaag    5820
aaatattata tgattcactt gatttaaggg ctcgtggaaa aatatttgaa ataacttcaa    5880
agcgaatgtt taagctt                                                   5897

<210> SEQ ID NO 29
<211> LENGTH: 300
<212> TYPE: DNA
<213> ORGANISM: Borrelia garinii
<220> FEATURE:
<221> NAME/KEY: CDS
<222> LOCATION: (1)..(300)

<400> SEQUENCE: 29 gtc att aat tat tta ata cta ttc agc agt aaa ttc tat aag tca tta     48
Val Ile Asn Tyr Leu Ile Leu Phe Ser Ser Lys Phe Tyr Lys Ser Leu
1               5                   10                  15 att caa tta ggt aac gga ttc tta gat gta ttc acc tct ttt ggt gga     96
Ile Gln Leu Gly Asn Gly Phe Leu Asp Val Phe Thr Ser Phe Gly Gly
            20                  25                  30 tta gtt gca gat gca ttg ggg ttt aaa gct gat cca aaa aaa tct gat    144
Leu Val Ala Asp Ala Leu Gly Phe Lys Ala Asp Pro Lys Lys Ser Asp
        35                  40                  45
```

```
gta aaa act tat ttt gaa tct cta gct aaa aaa tta gaa gaa aca aaa      192
Val Lys Thr Tyr Phe Glu Ser Leu Ala Lys Lys Leu Glu Glu Thr Lys
 50              55                  60 gat ggt tta act aag ttg tcc aaa ggt aat gac ggt gat act gga aag      240
Asp Gly Leu Thr Lys Leu Ser Lys Gly Asn Asp Gly Asp Thr Gly Lys
 65              70                  75                  80 gct ggt gat gct ggt ggg gct ggt ggc gct agt gct gca ggt ggc          288
Ala Gly Asp Ala Gly Gly Ala Gly Gly Ala Ser Ala Ala Gly Gly
                 85                  90                  95 gct ggt ggg att                                                      300
Ala Gly Gly Ile
            100
```

<210> SEQ ID NO 30
<211> LENGTH: 100
<212> TYPE: PRT
<213> ORGANISM: Borrelia garinii

<400> SEQUENCE: 30

Val Ile Asn Tyr Leu Ile Leu Phe Ser Ser Lys Phe Tyr Lys Ser Leu
 1               5                   10                  15

Ile Gln Leu Gly Asn Gly Phe Leu Asp Val Phe Thr Ser Phe Gly Gly
                 20                  25                  30

Leu Val Ala Asp Ala Leu Gly Phe Lys Ala Asp Pro Lys Lys Ser Asp
             35                  40                  45

Val Lys Thr Tyr Phe Glu Ser Leu Ala Lys Lys Leu Glu Glu Thr Lys
 50              55                  60

Asp Gly Leu Thr Lys Leu Ser Lys Gly Asn Asp Gly Asp Thr Gly Lys
 65              70                  75                  80

Ala Gly Asp Ala Gly Gly Ala Gly Gly Ala Ser Ala Ala Gly Gly
                 85                  90                  95

Ala Gly Gly Ile
            100

<210> SEQ ID NO 31
<211> LENGTH: 102
<212> TYPE: DNA
<213> ORGANISM: Borrelia garinii
<220> FEATURE:
<221> NAME/KEY: CDS
<222> LOCATION: (1)..(102)

<400> SEQUENCE: 31

```
ggg ttt aaa gct gat cca aaa aaa tct gat gta aaa act tat ttt gaa       48
Gly Phe Lys Ala Asp Pro Lys Lys Ser Asp Val Lys Thr Tyr Phe Glu
 1               5                  10                  15 tct cta gct aaa aaa tta gaa gaa aca aaa gat ggt tta act aag ttg       96
Ser Leu Ala Lys Lys Leu Glu Glu Thr Lys Asp Gly Leu Thr Lys Leu
                 20                  25                  30 tcc aaa                                                              102
Ser Lys
```

<210> SEQ ID NO 32
<211> LENGTH: 34
<212> TYPE: PRT
<213> ORGANISM: Borrelia garinii

<400> SEQUENCE: 32

Gly Phe Lys Ala Asp Pro Lys Lys Ser Asp Val Lys Thr Tyr Phe Glu
 1               5                  10                  15

Ser Leu Ala Lys Lys Leu Glu Glu Thr Lys Asp Gly Leu Thr Lys Leu

```
                    20                  25                  30

Ser Lys

<210> SEQ ID NO 33
<211> LENGTH: 288
<212> TYPE: DNA
<213> ORGANISM: Borrelia garinii
<220> FEATURE:
<221> NAME/KEY: CDS
<222> LOCATION: (1)..(288)

<400> SEQUENCE: 33 gag ggc gct ata aca gag att agc aaa tgg tta gat gat atg gca aaa        48
Glu Gly Ala Ile Thr Glu Ile Ser Lys Trp Leu Asp Asp Met Ala Lys
1               5                   10                  15 gct gct gcg gaa gct gca agt gct gca act ggt aat gca gca att ggg        96
Ala Ala Ala Glu Ala Ala Ser Ala Ala Thr Gly Asn Ala Ala Ile Gly
                20                  25                  30 gat gtt gtt aat ggt aat ggt gga gca gca aaa ggt ggt gat gcg gag       144
Asp Val Val Asn Gly Asn Gly Gly Ala Ala Lys Gly Gly Asp Ala Glu
            35                  40                  45 agt gtt aat ggg att gct aag ggg ata aag ggg att gtt gat gct gct       192
Ser Val Asn Gly Ile Ala Lys Gly Ile Lys Gly Ile Val Asp Ala Ala
        50                  55                  60 gag aag gct gat gcg aag gaa ggg aag ttg gat gtg gct ggt gat gct       240
Glu Lys Ala Asp Ala Lys Glu Gly Lys Leu Asp Val Ala Gly Asp Ala
65                  70                  75                  80 ggt ggg gct ggt ggt ggc gct ggt gct gca ggt ggc gct ggt ggg att       288
Gly Gly Ala Gly Gly Gly Ala Gly Ala Ala Gly Gly Ala Gly Gly Ile
                85                  90                  95

<210> SEQ ID NO 34
<211> LENGTH: 96
<212> TYPE: PRT
<213> ORGANISM: Borrelia garinii

<400> SEQUENCE: 34

Glu Gly Ala Ile Thr Glu Ile Ser Lys Trp Leu Asp Asp Met Ala Lys
1               5                   10                  15

Ala Ala Ala Glu Ala Ala Ser Ala Ala Thr Gly Asn Ala Ala Ile Gly
                20                  25                  30

Asp Val Val Asn Gly Asn Gly Gly Ala Ala Lys Gly Gly Asp Ala Glu
            35                  40                  45

Ser Val Asn Gly Ile Ala Lys Gly Ile Lys Gly Ile Val Asp Ala Ala
        50                  55                  60

Glu Lys Ala Asp Ala Lys Glu Gly Lys Leu Asp Val Ala Gly Asp Ala
65                  70                  75                  80

Gly Gly Ala Gly Gly Gly Ala Gly Ala Ala Gly Gly Ala Gly Gly Ile
                85                  90                  95

<210> SEQ ID NO 35
<211> LENGTH: 594
<212> TYPE: DNA
<213> ORGANISM: Borrelia garinii
<220> FEATURE:
<221> NAME/KEY: CDS
<222> LOCATION: (1)..(594)

<400> SEQUENCE: 35 gag ggc gct ata aca gag att agc aaa tgg tta gat gat atg gca aaa        48
Glu Gly Ala Ile Thr Glu Ile Ser Lys Trp Leu Asp Asp Met Ala Lys
1               5                   10                  15
```

```
gct gct gcg gtt gct gca agt gct gca agt gct gct act ggt aat gca        96
Ala Ala Ala Val Ala Ala Ser Ala Ala Ser Ala Ala Thr Gly Asn Ala
            20                  25                  30 gca att ggg gat gtt gtt aat ggt aat gat gga gca gca aaa ggt ggt       144
Ala Ile Gly Asp Val Val Asn Gly Asn Asp Gly Ala Ala Lys Gly Gly
        35                  40                  45 gat gcg gcg agt gtt aat ggg att gct aag ggg ata aag ggg att gtt       192
Asp Ala Ala Ser Val Asn Gly Ile Ala Lys Gly Ile Lys Gly Ile Val
 50                  55                  60 gat gct gct gag aag gct gat gcg aag gaa ggg aag ttg gat gtg gct       240
Asp Ala Ala Glu Lys Ala Asp Ala Lys Glu Gly Lys Leu Asp Val Ala
 65                  70                  75                  80 ggt gat gct ggt gag ggt aac aag gat gct ggg aag ctg ttt gtg aag       288
Gly Asp Ala Gly Glu Gly Asn Lys Asp Ala Gly Lys Leu Phe Val Lys
                 85                  90                  95 aag aat gct ggt gat gag ggt ggt gaa gca aat gat gct ggg aag gct       336
Lys Asn Ala Gly Asp Glu Gly Gly Glu Ala Asn Asp Ala Gly Lys Ala
            100                 105                 110 gct gct gcg gtt gct gct gtt agt ggg gag cag ata tta aaa gcg att       384
Ala Ala Ala Val Ala Ala Val Ser Gly Glu Gln Ile Leu Lys Ala Ile
        115                 120                 125 gtt gat gct gct gag ggt gat gat aag cag ggt aag aag gct gcg gat       432
Val Asp Ala Ala Glu Gly Asp Asp Lys Gln Gly Lys Lys Ala Ala Asp
130                 135                 140 gct aca aat ccg att gag gcg gct att ggg ggt gcg gat gcg ggt gct       480
Ala Thr Asn Pro Ile Glu Ala Ala Ile Gly Gly Ala Asp Ala Gly Ala
145                 150                 155                 160 aat gct gag gcg ttt aat aag atg aag aag gat gat cag att gct gct       528
Asn Ala Glu Ala Phe Asn Lys Met Lys Lys Asp Asp Gln Ile Ala Ala
                165                 170                 175 gct atg gtt ctg agg gga atg gct aag gat ggg cag ttt gct ttg aag       576
Ala Met Val Leu Arg Gly Met Ala Lys Asp Gly Gln Phe Ala Leu Lys
            180                 185                 190 gat gat gct gct gct cat                                               594
Asp Asp Ala Ala Ala His
            195

<210> SEQ ID NO 36
<211> LENGTH: 198
<212> TYPE: PRT
<213> ORGANISM: Borrelia garinii

<400> SEQUENCE: 36

Glu Gly Ala Ile Thr Glu Ile Ser Lys Trp Leu Asp Asp Met Ala Lys
1               5                   10                  15

Ala Ala Ala Val Ala Ala Ser Ala Ala Ser Ala Ala Thr Gly Asn Ala
            20                  25                  30

Ala Ile Gly Asp Val Val Asn Gly Asn Asp Gly Ala Ala Lys Gly Gly
        35                  40                  45

Asp Ala Ala Ser Val Asn Gly Ile Ala Lys Gly Ile Lys Gly Ile Val
 50                  55                  60

Asp Ala Ala Glu Lys Ala Asp Ala Lys Glu Gly Lys Leu Asp Val Ala
 65                  70                  75                  80

Gly Asp Ala Gly Glu Gly Asn Lys Asp Ala Gly Lys Leu Phe Val Lys
                 85                  90                  95

Lys Asn Ala Gly Asp Glu Gly Gly Glu Ala Asn Asp Ala Gly Lys Ala
            100                 105                 110

Ala Ala Ala Val Ala Ala Val Ser Gly Glu Gln Ile Leu Lys Ala Ile
```

```
            115                 120                 125
Val Asp Ala Ala Glu Gly Asp Asp Lys Gln Gly Lys Lys Ala Ala Asp
    130                 135                 140

Ala Thr Asn Pro Ile Glu Ala Ala Ile Gly Gly Ala Asp Ala Gly Ala
145                 150                 155                 160

Asn Ala Glu Ala Phe Asn Lys Met Lys Lys Asp Asp Gln Ile Ala Ala
                165                 170                 175

Ala Met Val Leu Arg Gly Met Ala Lys Asp Gly Gln Phe Ala Leu Lys
            180                 185                 190

Asp Asp Ala Ala Ala His
        195

<210> SEQ ID NO 37
<211> LENGTH: 573
<212> TYPE: DNA
<213> ORGANISM: Borrelia garinii
<220> FEATURE:
<221> NAME/KEY: CDS
<222> LOCATION: (1)..(573)

<400> SEQUENCE: 37
```

| | | | | | | | | | | | | | | | | |
|---|---|---|---|---|---|---|---|---|---|---|---|---|---|---|---|---|
| gaa | ggg | act | gtt | aag | aat | gct | gtt | gat | atg | gca | aag | gcc | gct | gcg | gaa | 48 |
| Glu | Gly | Thr | Val | Lys | Asn | Ala | Val | Asp | Met | Ala | Lys | Ala | Ala | Ala | Glu | |
| 1 | | | | 5 | | | | | 10 | | | | | 15 | | |
| gct | gca | agt | gct | gca | agt | gct | gct | act | ggt | agt | aca | acg | att | gga | gat | 96 |
| Ala | Ala | Ser | Ala | Ala | Ser | Ala | Ala | Thr | Gly | Ser | Thr | Thr | Ile | Gly | Asp | |
| | | | 20 | | | | | 25 | | | | | 30 | | | |
| gtt | gtt | aag | agt | ggt | gag | gca | aaa | gat | ggt | gat | gcg | gcg | agt | gtt | aat | 144 |
| Val | Val | Lys | Ser | Gly | Glu | Ala | Lys | Asp | Gly | Asp | Ala | Ala | Ser | Val | Asn | |
| | | 35 | | | | | 40 | | | | | 45 | | | | |
| ggg | att | gct | aag | ggg | ata | aag | ggg | att | gtt | gat | gct | gct | gag | aag | gct | 192 |
| Gly | Ile | Ala | Lys | Gly | Ile | Lys | Gly | Ile | Val | Asp | Ala | Ala | Glu | Lys | Ala | |
| | 50 | | | | | 55 | | | | | 60 | | | | | |
| gat | gcg | aag | gaa | ggg | aag | ttg | gat | gtg | gct | ggt | gct | gct | ggt | acg | act | 240 |
| Asp | Ala | Lys | Glu | Gly | Lys | Leu | Asp | Val | Ala | Gly | Ala | Ala | Gly | Thr | Thr | |
| 65 | | | | 70 | | | | | 75 | | | | | 80 | | |
| aac | gtg | aat | gtt | ggg | aag | ttg | ttt | gtg | aag | aat | aat | ggt | aat | gag | ggt | 288 |
| Asn | Val | Asn | Val | Gly | Lys | Leu | Phe | Val | Lys | Asn | Asn | Gly | Asn | Glu | Gly | |
| | | | | 85 | | | | | 90 | | | | | 95 | | |
| ggt | gat | gca | agt | gat | gct | ggg | aaa | gct | gct | gct | gcg | gtt | gct | gct | gtt | 336 |
| Gly | Asp | Ala | Ser | Asp | Ala | Gly | Lys | Ala | Ala | Ala | Ala | Val | Ala | Ala | Val | |
| | | | 100 | | | | | 105 | | | | | 110 | | | |
| agt | ggg | gag | cag | ata | tta | aaa | gcg | att | gtt | gat | gct | gct | aaa | gat | ggt | 384 |
| Ser | Gly | Glu | Gln | Ile | Leu | Lys | Ala | Ile | Val | Asp | Ala | Ala | Lys | Asp | Gly | |
| | | 115 | | | | | 120 | | | | | 125 | | | | |
| gat | aag | cag | ggg | gtt | act | gat | gta | aag | gat | gct | aca | aat | ccg | att | gag | 432 |
| Asp | Lys | Gln | Gly | Val | Thr | Asp | Val | Lys | Asp | Ala | Thr | Asn | Pro | Ile | Glu | |
| | 130 | | | | | 135 | | | | | 140 | | | | | |
| gcg | gct | att | ggg | ggt | aca | aat | gat | aat | gat | gct | gcg | gcg | ttt | gct | act | 480 |
| Ala | Ala | Ile | Gly | Gly | Thr | Asn | Asp | Asn | Asp | Ala | Ala | Ala | Phe | Ala | Thr | |
| 145 | | | | 150 | | | | | 155 | | | | | 160 | | |
| atg | aag | aag | gat | gat | cag | att | gct | gct | gct | atg | gtt | ctg | agg | gga | atg | 528 |
| Met | Lys | Lys | Asp | Asp | Gln | Ile | Ala | Ala | Ala | Met | Val | Leu | Arg | Gly | Met | |
| | | | | 165 | | | | | 170 | | | | | 175 | | |
| gct | aag | gat | ggg | cag | ttt | gct | ttg | aag | gat | gct | gct | aag | gat | | | 573 |
| Ala | Lys | Asp | Gly | Gln | Phe | Ala | Leu | Lys | Asp | Ala | Ala | Lys | Asp | | | |
| | | | 180 | | | | | 185 | | | | | 190 | | | |

```
<210> SEQ ID NO 38
<211> LENGTH: 191
```

<212> TYPE: PRT
<213> ORGANISM: Borrelia garinii

<400> SEQUENCE: 38

Glu Gly Thr Val Lys Asn Ala Val Asp Met Ala Lys Ala Ala Ala Glu
1               5                   10                  15

Ala Ala Ser Ala Ala Ser Ala Ala Thr Gly Ser Thr Thr Ile Gly Asp
            20                  25                  30

Val Val Lys Ser Gly Glu Ala Lys Asp Gly Asp Ala Ala Ser Val Asn
        35                  40                  45

Gly Ile Ala Lys Gly Ile Lys Gly Ile Val Asp Ala Ala Glu Lys Ala
    50                  55                  60

Asp Ala Lys Glu Gly Lys Leu Asp Val Ala Gly Ala Ala Gly Thr Thr
65                  70                  75                  80

Asn Val Asn Val Gly Lys Leu Phe Val Lys Asn Gly Asn Glu Gly
                85                  90                  95

Gly Asp Ala Ser Asp Ala Gly Lys Ala Ala Ala Val Ala Ala Val
            100                 105                 110

Ser Gly Glu Gln Ile Leu Lys Ala Ile Val Asp Ala Ala Lys Asp Gly
    115                 120                 125

Asp Lys Gln Gly Val Thr Asp Val Lys Asp Ala Thr Asn Pro Ile Glu
    130                 135                 140

Ala Ala Ile Gly Gly Thr Asn Asp Asn Asp Ala Ala Phe Ala Thr
145                 150                 155                 160

Met Lys Lys Asp Asp Gln Ile Ala Ala Ala Met Val Leu Arg Gly Met
                165                 170                 175

Ala Lys Asp Gly Gln Phe Ala Leu Lys Asp Asp Ala Ala Lys Asp
            180                 185                 190

<210> SEQ ID NO 39
<211> LENGTH: 189
<212> TYPE: DNA
<213> ORGANISM: Borrelia garinii
<220> FEATURE:
<221> NAME/KEY: CDS
<222> LOCATION: (1)..(189)

<400> SEQUENCE: 39 ggt gat aaa acg ggg gtt gct gcg gat gct gaa aat ccg att gac gcg      48
Gly Asp Lys Thr Gly Val Ala Ala Asp Ala Glu Asn Pro Ile Asp Ala
1               5                   10                  15 gct att ggg ggt gcg gat gct gat gct gcg gcg ttt aat aag gag ggg      96
Ala Ile Gly Gly Ala Asp Ala Asp Ala Ala Phe Asn Lys Glu Gly
            20                  25                  30 atg aag aag gat gat cag att gct gct gct atg gtt ctg agg gga atg     144
Met Lys Lys Asp Asp Gln Ile Ala Ala Ala Met Val Leu Arg Gly Met
    35                  40                  45 gct aag gat ggg cag ttt gct ttg acg aat aat gct gct gct cat         189
Ala Lys Asp Gly Gln Phe Ala Leu Thr Asn Asn Ala Ala Ala His
    50                  55                  60

<210> SEQ ID NO 40
<211> LENGTH: 63
<212> TYPE: PRT
<213> ORGANISM: Borrelia garinii

<400> SEQUENCE: 40

Gly Asp Lys Thr Gly Val Ala Ala Asp Ala Glu Asn Pro Ile Asp Ala
1               5                   10                  15

```
Ala Ile Gly Gly Ala Asp Ala Asp Ala Ala Phe Asn Lys Glu Gly
         20                  25                  30

Met Lys Lys Asp Asp Gln Ile Ala Ala Met Val Leu Arg Gly Met
         35                  40                  45

Ala Lys Asp Gly Gln Phe Ala Leu Thr Asn Asn Ala Ala Ala His
         50                  55                  60

<210> SEQ ID NO 41
<211> LENGTH: 576
<212> TYPE: DNA
<213> ORGANISM: Borrelia garinii
<220> FEATURE:
<221> NAME/KEY: CDS
<222> LOCATION: (1)..(576)

<400> SEQUENCE: 41 gaa ggg act gtt aag aat gct gtt gat atg gca aaa gct gct gcg gtt      48
Glu Gly Thr Val Lys Asn Ala Val Asp Met Ala Lys Ala Ala Ala Val
1               5                   10                  15 gct gca agt gct gct act ggc aat gca gca att ggg gat gtt gtt aag      96
Ala Ala Ser Ala Ala Thr Gly Asn Ala Ala Ile Gly Asp Val Val Lys
            20                  25                  30 agt aat ggt gga gca gca gca aaa ggt ggt gat gcg gcg agt gtt aat     144
Ser Asn Gly Gly Ala Ala Ala Lys Gly Gly Asp Ala Ala Ser Val Asn
        35                  40                  45 ggg att gct aag ggg ata aag ggg att gtt gat gct gct gag aag gct     192
Gly Ile Ala Lys Gly Ile Lys Gly Ile Val Asp Ala Ala Glu Lys Ala
    50                  55                  60 gat gcg aag gaa ggg aag ttg gat gtg gct ggt gct gct ggt gaa act     240
Asp Ala Lys Glu Gly Lys Leu Asp Val Ala Gly Ala Ala Gly Glu Thr
65                  70                  75                  80 aac aag gat gct ggg aag ttg ttt gtg aag aag aat ggt gat gat ggt     288
Asn Lys Asp Ala Gly Lys Leu Phe Val Lys Lys Asn Gly Asp Asp Gly
                85                  90                  95 ggt gat gca ggt gat gct ggg aag gct gct gct gcg gtt gct gct gtt     336
Gly Asp Ala Gly Asp Ala Gly Lys Ala Ala Ala Ala Val Ala Ala Val
            100                 105                 110 agt ggg gag cag ata tta aaa gcg att gtt gat gct gct aaa gat ggt     384
Ser Gly Glu Gln Ile Leu Lys Ala Ile Val Asp Ala Ala Lys Asp Gly
        115                 120                 125 gat aag acg ggg gtt act gat gta aag gat gct aca aat ccg att gac     432
Asp Lys Thr Gly Val Thr Asp Val Lys Asp Ala Thr Asn Pro Ile Asp
    130                 135                 140 gcg gct att ggg ggg agt gcg gat gct aat gct gag gcg ttt gat aag     480
Ala Ala Ile Gly Gly Ser Ala Asp Ala Asn Ala Glu Ala Phe Asp Lys
145                 150                 155                 160 atg aag aag gat gat cag att gct gct gct atg gtt ctg agg gga atg     528
Met Lys Lys Asp Asp Gln Ile Ala Ala Ala Met Val Leu Arg Gly Met
                165                 170                 175 gct aag gat ggg cag ttt gct ttg aag aat aat gat cat gat aat cat     576
Ala Lys Asp Gly Gln Phe Ala Leu Lys Asn Asn Asp His Asp Asn His
            180                 185                 190

<210> SEQ ID NO 42
<211> LENGTH: 192
<212> TYPE: PRT
<213> ORGANISM: Borrelia garinii

<400> SEQUENCE: 42

Glu Gly Thr Val Lys Asn Ala Val Asp Met Ala Lys Ala Ala Ala Val
1               5                   10                  15
```

```
Ala Ala Ser Ala Ala Thr Gly Asn Ala Ile Gly Asp Val Val Lys
            20                  25                  30

Ser Asn Gly Gly Ala Ala Lys Gly Gly Asp Ala Ala Ser Val Asn
        35                  40                  45

Gly Ile Ala Lys Gly Ile Lys Gly Ile Val Asp Ala Ala Glu Lys Ala
    50                  55                  60

Asp Ala Lys Glu Gly Lys Leu Asp Val Ala Gly Ala Ala Gly Glu Thr
65                  70                  75                  80

Asn Lys Asp Ala Gly Lys Leu Phe Val Lys Asn Gly Asp Asp Gly
                85                  90                  95

Gly Asp Ala Gly Asp Ala Gly Lys Ala Ala Ala Val Ala Ala Val
            100                 105                 110

Ser Gly Glu Gln Ile Leu Lys Ala Ile Val Asp Ala Ala Lys Asp Gly
        115                 120                 125

Asp Lys Thr Gly Val Thr Asp Val Lys Asp Ala Thr Asn Pro Ile Asp
    130                 135                 140

Ala Ala Ile Gly Gly Ser Ala Asp Ala Asn Ala Glu Ala Phe Asp Lys
145                 150                 155                 160

Met Lys Lys Asp Asp Gln Ile Ala Ala Ala Met Val Leu Arg Gly Met
                165                 170                 175

Ala Lys Asp Gly Gln Phe Ala Leu Lys Asn Asn Asp His Asp Asn His
            180                 185                 190
```

<210> SEQ ID NO 43
<211> LENGTH: 336
<212> TYPE: DNA
<213> ORGANISM: Borrelia garinii
<220> FEATURE:
<221> NAME/KEY: CDS
<222> LOCATION: (1)..(336)

<400> SEQUENCE: 43

```
aag ggg act gtt aag aat gct gtt gat atg gca aag gcc gct gag gaa    48
Lys Gly Thr Val Lys Asn Ala Val Asp Met Ala Lys Ala Ala Glu Glu
1               5                   10                  15 gct gca agt gct gca agt gct gct act ggt aat gca gcg att ggg gat   96
Ala Ala Ser Ala Ala Ser Ala Ala Thr Gly Asn Ala Ala Ile Gly Asp
                20                  25                  30 gtt gtt aag aat agt ggg gca gca gca aaa ggt ggt gag gcg gcg agt  144
Val Val Lys Asn Ser Gly Ala Ala Ala Lys Gly Gly Glu Ala Ala Ser
            35                  40                  45 gtt aat ggg att gct aag ggg ata aag ggg att gtt gat gct gct gga  192
Val Asn Gly Ile Ala Lys Gly Ile Lys Gly Ile Val Asp Ala Ala Gly
    50                  55                  60 aag gct gat gcg aag gaa ggg aag ttg gat gct act ggt gct gag ggt  240
Lys Ala Asp Ala Lys Glu Gly Lys Leu Asp Ala Thr Gly Ala Glu Gly
65                  70                  75                  80 acg act aac gtg aat gct ggg aag ttg ttt gtg aag agg gcg gct gat  288
Thr Thr Asn Val Asn Ala Gly Lys Leu Phe Val Lys Arg Ala Ala Asp
                85                  90                  95 gat ggt ggt gat gca gat gat gct ggg aag gct gct gct gcg gtt gct  336
Asp Gly Gly Asp Ala Asp Asp Ala Gly Lys Ala Ala Ala Ala Val Ala
            100                 105                 110
```

<210> SEQ ID NO 44
<211> LENGTH: 112
<212> TYPE: PRT
<213> ORGANISM: Borrelia garinii

<400> SEQUENCE: 44

```
Lys Gly Thr Val Lys Asn Ala Val Asp Met Ala Lys Ala Ala Glu Glu
1               5                   10                  15

Ala Ala

<211> LENGTH: 174
<212> TYPE: PRT
<213> ORGANISM: Borrelia garinii

<400> SEQUENCE: 46

```
Ala Ser Ala Ala Thr Gly Asn Ala Ala Ile Gly Asp Val Val Asn Gly
1               5                   10                  15
Asp Val Ala Lys Ala Lys Gly Gly Asp Ala Ala Ser Val Asn Gly Ile
            20                  25                  30
Ala Lys Gly Ile Lys Gly Ile Val Asp Ala Ala Glu Lys Ala Asp Ala
        35                  40                  45
Lys Glu Gly Lys Leu Asn Ala Ala Gly Ala Glu Gly Thr Thr Asn Ala
50                  55                  60
Asp Ala Gly Lys Leu Phe Val Lys Asn Ala Gly Asn Val Gly Gly Glu
65                  70                  75                  80
Ala Gly Asp Ala Gly Lys Ala Ala Ala Val Ala Ala Val Ser Gly
                85                  90                  95
Glu Gln Ile Leu Lys Ala Ile Val Asp Ala Ala Lys Asp Gly Gly Glu
            100                 105                 110
Lys Gln Gly Lys Lys Ala Ala Asp Ala Thr Asn Pro Ile Asp Ala Ala
        115                 120                 125
Ile Gly Gly Thr Asn Asp Asn Asp Ala Ala Ala Phe Ala Thr Met
130                 135                 140
Lys Lys Asp Asp Gln Ile Ala Ala Ala Met Val Leu Arg Gly Met Ala
145                 150                 155                 160
Lys Asp Gly Gln Phe Ala Leu Lys Asp Ala Ala Ala His
                165                 170
```

<210> SEQ ID NO 47
<211> LENGTH: 585
<212> TYPE: DNA
<213> ORGANISM: Borrelia garinii
<220> FEATURE:
<221> NAME/KEY: CDS
<222> LOCATION: (1)..(585)

<400> SEQUENCE: 47

```
gaa ggg act gtt aag aat gct gtt gat ata ata aag gct gct gcg gaa    48
Glu Gly Thr Val Lys Asn Ala Val Asp Ile Ile Lys Ala Ala Ala Glu
1               5                   10                  15 gct gca agt gct gca agt gct gct act ggt agt gca gca att ggg gat    96
Ala Ala Ser Ala Ala Ser Ala Ala Thr Gly Ser Ala Ala Ile Gly Asp
            20                  25                  30 gtt gtt aat ggt aat gga gca aca gca aaa ggt ggt gat gcg aag agt   144
Val Val Asn Gly Asn Gly Ala Thr Ala Lys Gly Gly Asp Ala Lys Ser
        35                  40                  45 gtt aat ggg att gct aag ggg ata aag ggg att gtt gat gct gct gag   192
Val Asn Gly Ile Ala Lys Gly Ile Lys Gly Ile Val Asp Ala Ala Glu
50                  55                  60 aag gct gat gcg aag gaa ggg aag ttg gat gtg gct ggt gat gct ggt   240
Lys Ala Asp Ala Lys Glu Gly Lys Leu Asp Val Ala Gly Asp Ala Gly
65                  70                  75                  80 gaa act aac aag gat gct ggg aag ttg ttt gtg aag aac aat ggt aat   288
Glu Thr Asn Lys Asp Ala Gly Lys Leu Phe Val Lys Asn Asn Gly Asn
                85                  90                  95 gag ggt ggt gat gca gat gat gct ggg aag gct gct gct gcg gtt gct   336
Glu Gly Gly Asp Ala Asp Asp Ala Gly Lys Ala Ala Ala Ala Val Ala
            100                 105                 110 gct gtt agt ggg gag cag ata tta aaa gcg att gtt gat gct gct aag   384
```

```
                Ala Val Ser Gly Glu Gln Ile Leu Lys Ala Ile Val Asp Ala Ala Lys
                            115                 120                 125 ggt ggt gat aag acg ggt aag aat aat gtg aag gat gct gaa aat ccg        432
Gly Gly Asp Lys Thr Gly Lys Asn Asn Val Lys Asp Ala Glu Asn Pro
            130                 135                 140 att gag gcg gct att ggg agt agt gcg gat gct gat gct gcg ttt            480
Ile Glu Ala Ala Ile Gly Ser Ser Ala Asp Ala Asp Ala Ala Phe
145                 150                 155                 160 aat aag gag ggg atg aag aag gat gat cag att gct gct gct atg gtt        528
Asn Lys Glu Gly Met Lys Lys Asp Asp Gln Ile Ala Ala Ala Met Val
            165                 170                 175 ctg agg gga atg gct aag gat ggg cag ttt gct ttg acg aat gat gct        576
Leu Arg Gly Met Ala Lys Asp Gly Gln Phe Ala Leu Thr Asn Asp Ala
            180                 185                 190 gct gct cat                                                            585
Ala Ala His
        195

<210> SEQ ID NO 48
<211> LENGTH: 195
<212> TYPE: PRT
<213> ORGANISM: Borrelia garinii

<400> SEQUENCE: 48

Glu Gly Thr Val Lys Asn Ala Val Asp Ile Ile Lys Ala Ala Ala Glu
1               5                   10                  15

Ala Ala Ser Ala Ala Ser Ala Ala Thr Gly Ser Ala Ala Ile Gly Asp
                20                  25                  30

Val Val Asn Gly Asn Gly Ala Thr Ala Lys Gly Gly Asp Ala Lys Ser
            35                  40                  45

Val Asn Gly Ile Ala Lys Gly Ile Lys Gly Ile Val Asp Ala Ala Glu
        50                  55                  60

Lys Ala Asp Ala Lys Glu Gly Lys Leu Asp Val Ala Gly Asp Ala Gly
65                  70                  75                  80

Glu Thr Asn Lys Asp Ala Gly Lys Leu Phe Val Lys Asn Asn Gly Asn
                85                  90                  95

Glu Gly Gly Asp Ala Asp Ala Gly Lys Ala Ala Ala Val Ala
            100                 105                 110

Ala Val Ser Gly Glu Gln Ile Leu Lys Ala Ile Val Asp Ala Ala Lys
        115                 120                 125

Gly Gly Asp Lys Thr Gly Lys Asn Asn Val Lys Asp Ala Glu Asn Pro
    130                 135                 140

Ile Glu Ala Ala Ile Gly Ser Ser Ala Asp Ala Asp Ala Ala Phe
145                 150                 155                 160

Asn Lys Glu Gly Met Lys Lys Asp Asp Gln Ile Ala Ala Ala Met Val
                165                 170                 175

Leu Arg Gly Met Ala Lys Asp Gly Gln Phe Ala Leu Thr Asn Asp Ala
            180                 185                 190

Ala Ala His
        195

<210> SEQ ID NO 49
<211> LENGTH: 591
<212> TYPE: DNA
<213> ORGANISM: Borrelia garinii
<220> FEATURE:
<221> NAME/KEY: CDS
<222> LOCATION: (1)..(591)
```

<400> SEQUENCE: 49

```
gaa ggg act gtt aag aat gct gtt ggg agt gca aca aat aag acc gtt      48
Glu Gly Thr Val Lys Asn Ala Val Gly Ser Ala Thr Asn Lys Thr Val
1               5                   10                  15 gtt gct ttg gct aac ttg gtt cga aag acc gtg caa gct ggg ttg aag      96
Val Ala Leu Ala Asn Leu Val Arg Lys Thr Val Gln Ala Gly Leu Lys
                20                  25                  30 aag gtt ggg gat gtt gtt aag aat agt gag gca aaa gat ggt gat gcg     144
Lys Val Gly Asp Val Val Lys Asn Ser Glu Ala Lys Asp Gly Asp Ala
            35                  40                  45 gcg agt gtt aat ggg att gct aag ggg ata aag ggg att gtt gat gct     192
Ala Ser Val Asn Gly Ile Ala Lys Gly Ile Lys Gly Ile Val Asp Ala
        50                  55                  60 gct gag aag gct gat gcg aag gaa ggg aag ttg gat gtg gct ggt gct     240
Ala Glu Lys Ala Asp Ala Lys Glu Gly Lys Leu Asp Val Ala Gly Ala
65                  70                  75                  80 gct ggt gaa act aac aag gat gct ggg aag ttg ttt gtg aag aag aat     288
Ala Gly Glu Thr Asn Lys Asp Ala Gly Lys Leu Phe Val Lys Lys Asn
                85                  90                  95 aat gag ggt ggt gaa gca aat gat gct ggg aag gct gct gct gcg gtt     336
Asn Glu Gly Gly Glu Ala Asn Asp Ala Gly Lys Ala Ala Ala Ala Val
                100                 105                 110 gct gct gtt agt ggg gag cag ata tta aaa gcg att gtt gat gct gct     384
Ala Ala Val Ser Gly Glu Gln Ile Leu Lys Ala Ile Val Asp Ala Ala
            115                 120                 125 aag gat ggt gat gat aag cag ggt aag aag gct gag gat gct aca aat     432
Lys Asp Gly Asp Asp Lys Gln Gly Lys Lys Ala Glu Asp Ala Thr Asn
        130                 135                 140 ccg att gac gcg gct att ggg ggt gca ggt gcg ggt gct aat gct gct     480
Pro Ile Asp Ala Ala Ile Gly Gly Ala Gly Ala Gly Ala Asn Ala Ala
145                 150                 155                 160 gcg gcg ttt aat aat atg aag aag gat gat cag att gct gct gct atg     528
Ala Ala Phe Asn Asn Met Lys Lys Asp Asp Gln Ile Ala Ala Ala Met
                165                 170                 175 gtt ctg agg gga atg gct aag gat ggg cag ttt gct ttg acg aat aat     576
Val Leu Arg Gly Met Ala Lys Asp Gly Gln Phe Ala Leu Thr Asn Asn
                180                 185                 190 gct cat act aat cat                                                  591
Ala His Thr Asn His
        195
```

<210> SEQ ID NO 50
<211> LENGTH: 197
<212> TYPE: PRT
<213> ORGANISM: Borrelia garinii

<400> SEQUENCE: 50

```
Glu Gly Thr Val Lys Asn Ala Val Gly Ser Ala Thr Asn Lys Thr Val
1               5                   10                  15

Val Ala Leu Ala Asn Leu Val Arg Lys Thr Val Gln Ala Gly Leu Lys
                20                  25                  30

Lys Val Gly Asp Val Val Lys Asn Ser Glu Ala Lys Asp Gly Asp Ala
            35                  40                  45

Ala Ser Val Asn Gly Ile Ala Lys Gly Ile Lys Gly Ile Val Asp Ala
        50                  55                  60

Ala Glu Lys Ala Asp Ala Lys Glu Gly Lys Leu Asp Val Ala Gly Ala
65                  70                  75                  80

Ala Gly Glu Thr Asn Lys Asp Ala Gly Lys Leu Phe Val Lys Lys Asn
                85                  90                  95
```

```
              Asn Glu Gly Gly Glu Ala Asn Asp Ala Gly Lys Ala Ala Ala Ala Val
                          100                 105                 110

Ala Ala Val Ser Gly Glu Gln Ile Leu Lys Ala Ile Val Asp Ala Ala
                          115                 120                 125

Lys Asp Gly Asp Lys Gln Gly Lys Lys Ala Glu Asp Ala Thr Asn
              130                 135                 140

Pro Ile Asp Ala Ala Ile Gly Ala Gly Ala Gly Ala Asn Ala Ala
              145                 150                 155                 160

Ala Ala Phe Asn Asn Met Lys Lys Asp Asp Gln Ile Ala Ala Met
                              165                 170                 175

Val Leu Arg Gly Met Ala Lys Asp Gly Gln Phe Ala Leu Thr Asn Asn
                          180                 185                 190

Ala His Thr Asn His
                          195

<210> SEQ ID NO 51
<211> LENGTH: 594
<212> TYPE: DNA
<213> ORGANISM: Borrelia garinii
<220> FEATURE:
<221> NAME/KEY: CDS
<222> LOCATION: (1)..(594)

<400> SEQUENCE: 51 aag ggg act gtt aag aat gct gtt gat atg aca aaa gct gct gcg gtt      48
Lys Gly Thr Val Lys Asn Ala Val Asp Met Thr Lys Ala Ala Ala Val
1               5                   10                  15 gct gca agt gct gca agt gct gct act ggt aat gca gca att ggg gat      96
Ala Ala Ser Ala Ala Ser Ala Ala Thr Gly Asn Ala Ala Ile Gly Asp
            20                  25                  30 gtt gtt aat ggt aat gat gga gca gca aaa ggt ggt gat gcg gcg agt     144
Val Val Asn Gly Asn Asp Gly Ala Ala Lys Gly Gly Asp Ala Ala Ser
        35                  40                  45 gtt aat ggg att gct aag ggg ata aag ggg att gtt gat gct gct gag     192
Val Asn Gly Ile Ala Lys Gly Ile Lys Gly Ile Val Asp Ala Ala Glu
    50                  55                  60 aag gct gat gcg aag gaa ggg aag ttg aat gtg gct ggt gct gct ggt     240
Lys Ala Asp Ala Lys Glu Gly Lys Leu Asn Val Ala Gly Ala Ala Gly
65                  70                  75                  80 gct gag ggt aac gag gct gct ggg aag ctg ttt gtg aag aag aat gct     288
Ala Glu Gly Asn Glu Ala Ala Gly Lys Leu Phe Val Lys Lys Asn Ala
                85                  90                  95 ggt gat cat ggt ggt gaa gca ggt gat gct ggg agg gct gct gct gcg     336
Gly Asp His Gly Gly Glu Ala Gly Asp Ala Gly Arg Ala Ala Ala Ala
            100                 105                 110 gtt gct gct gtt agt ggg gag cag ata tta aaa gcg att gtt gat gct     384
Val Ala Ala Val Ser Gly Glu Gln Ile Leu Lys Ala Ile Val Asp Ala
        115                 120                 125 gct aag gat ggt ggt gat aag cag ggt aag aag gct gag gat gct gaa     432
Ala Lys Asp Gly Gly Asp Lys Gln Gly Lys Lys Ala Glu Asp Ala Glu
    130                 135                 140 aat ccg att gac gcg gct att ggg agt acg ggt gcg gat gat aat gct     480
Asn Pro Ile Asp Ala Ala Ile Gly Ser Thr Gly Ala Asp Asp Asn Ala
145                 150                 155                 160 gct gag gcg ttt gct act atg aag aag gat gat cag att gct gct gct     528
Ala Glu Ala Phe Ala Thr Met Lys Lys Asp Asp Gln Ile Ala Ala Ala
                165                 170                 175 atg gtt ctg agg gga atg gct aag gat ggg cag ttt gct ttg aag gat     576
Met Val Leu Arg Gly Met Ala Lys Asp Gly Gln Phe Ala Leu Lys Asp
```

```
                180                 185                 190
gct gct cat gat aat cat                                                  594
Ala Ala His Asp Asn His
        195

<210> SEQ ID NO 52
<211> LENGTH: 198
<212> TYPE: PRT
<213> ORGANISM: Borrelia garinii

<400> SEQUENCE: 52

Lys Gly Thr Val Lys Asn Ala Val Asp Met Thr Lys Ala Ala Val
1               5                   10                  15

Ala Ala Ser Ala Ala Ser Ala Ala Thr Gly Asn Ala Ala Ile Gly Asp
            20                  25                  30

Val Val Asn Gly Asn Asp Gly Ala Ala Lys Gly Gly Asp Ala Ala Ser
        35                  40                  45

Val Asn Gly Ile Ala Lys Gly Ile Lys Gly Ile Val Asp Ala Ala Glu
    50                  55                  60

Lys Ala Asp Ala Lys Glu Gly Lys Leu Asn Val Ala Gly Ala Ala Gly
65                  70                  75                  80

Ala Glu Gly Asn Glu Ala Ala Gly Lys Leu Phe Val Lys Lys Asn Ala
                85                  90                  95

Gly Asp His Gly Gly Glu Ala Gly Asp Ala Gly Arg Ala Ala Ala Ala
            100                 105                 110

Val Ala Ala Val Ser Gly Glu Gln Ile Leu Lys Ala Ile Val Asp Ala
        115                 120                 125

Ala Lys Asp Gly Gly Asp Lys Gln Gly Lys Lys Ala Glu Asp Ala Glu
    130                 135                 140

Asn Pro Ile Asp Ala Ala Ile Gly Ser Thr Gly Ala Asp Asn Ala
145                 150                 155                 160

Ala Glu Ala Phe Ala Thr Met Lys Lys Asp Asp Gln Ile Ala Ala
                165                 170                 175

Met Val Leu Arg Gly Met Ala Lys Asp Gly Gln Phe Ala Leu Lys Asp
            180                 185                 190

Ala Ala His Asp Asn His
        195

<210> SEQ ID NO 53
<211> LENGTH: 261
<212> TYPE: DNA
<213> ORGANISM: Borrelia garinii
<220> FEATURE:
<221> NAME/KEY: CDS
<222> LOCATION: (1)..(261)

<400> SEQUENCE: 53 aag ggg act gtt aag aat gct gtt gat ata ata aag gct act gcg gtt    48
Lys Gly Thr Val Lys Asn Ala Val Asp Ile Ile Lys Ala Thr Ala Val
1               5                   10                  15 gct gca agt gct gct act ggt agt aca acg att ggg gat gtt gtt aag    96
Ala Ala Ser Ala Ala Thr Gly Ser Thr Thr Ile Gly Asp Val Val Lys
            20                  25                  30 aat ggt gag gca aaa ggt ggt gag gcg aag agt gtt aat ggg att gct   144
Asn Gly Glu Ala Lys Gly Gly Glu Ala Lys Ser Val Asn Gly Ile Ala
        35                  40                  45 aag ggg ata aag ggg att gtt gat gct gct gga aag gct gat gcg aag   192
Lys Gly Ile Lys Gly Ile Val Asp Ala Ala Gly Lys Ala Asp Ala Lys
    50                  55                  60
```

```
gaa ggg aag ttg aat gtg gct ggt gct gct ggt gag ggt aac gag gct    240
Glu Gly Lys Leu Asn Val Ala Gly Ala Ala Gly Glu Gly Asn Glu Ala
65                  70                  75                  80 gct ggg aag ctg ttt gtg taa                                        261
Ala Gly Lys Leu Phe Val
                85
```

<210> SEQ ID NO 54
<211> LENGTH: 86
<212> TYPE: PRT
<213> ORGANISM: Borrelia garinii

<400> SEQUENCE: 54

```
Lys Gly Thr Val Lys Asn Ala Val Asp Ile Ile Lys Ala Thr Ala Val
1               5                   10                  15

Ala Ala Ser Ala Ala Thr Gly Ser Thr Thr Ile Gly Asp Val Val Lys
                20                  25                  30

Asn Gly Glu Ala Lys Gly Gly Glu Ala Lys Ser Val Asn Gly Ile Ala
            35                  40                  45

Lys Gly Ile Lys Gly Ile Val Asp Ala Ala Gly Lys Ala Asp Ala Lys
        50                  55                  60

Glu Gly Lys Leu Asn Val Ala Gly Ala Ala Gly Glu Gly Asn Glu Ala
65                  70                  75                  80

Ala Gly Lys Leu Phe Val
                85
```

<210> SEQ ID NO 55
<211> LENGTH: 213
<212> TYPE: DNA
<213> ORGANISM: Borrelia garinii
<220> FEATURE:
<221> NAME/KEY: CDS
<222> LOCATION: (1)..(213)

<400> SEQUENCE: 55

```
gta aat tac tat agg att aga act agt gta cga tat gag tcc ttt ggt    48
Val Asn Tyr Tyr Arg Ile Arg Thr Ser Val Arg Tyr Glu Ser Phe Gly
1               5                   10                  15 tat ttt gca gct gct aat gaa ttt gaa ata agt gaa gtt aaa att gcg    96
Tyr Phe Ala Ala Ala Asn Glu Phe Glu Ile Ser Glu Val Lys Ile Ala
                20                  25                  30 gat gtt aat gga aca cat ttt att gct aca aaa gag aaa gaa ata tta   144
Asp Val Asn Gly Thr His Phe Ile Ala Thr Lys Glu Lys Glu Ile Leu
            35                  40                  45 tat gat tca ctt gat tta agg gct cgt gga aaa ata ttt gaa ata act   192
Tyr Asp Ser Leu Asp Leu Arg Ala Arg Gly Lys Ile Phe Glu Ile Thr
        50                  55                  60 tca aag cga atg ttt aag ctt                                       213
Ser Lys Arg Met Phe Lys Leu
65                  70
```

<210> SEQ ID NO 56
<211> LENGTH: 71
<212> TYPE: PRT
<213> ORGANISM: Borrelia garinii

<400> SEQUENCE: 56

```
Val Asn Tyr Tyr Arg Ile Arg Thr Ser Val Arg Tyr Glu Ser Phe Gly
1               5                   10                  15

Tyr Phe Ala Ala Ala Asn Glu Phe Glu Ile Ser Glu Val Lys Ile Ala
                20                  25                  30
```

Asp Val Asn Gly Thr His Phe Ile Ala Thr Lys Glu Lys Glu Ile Leu
        35                  40                  45

Tyr Asp Ser Leu Asp Leu Arg Ala Arg Gly Lys Ile Phe Glu Ile Thr
    50                  55                  60

Ser Lys Arg Met Phe Lys Leu
65                  70

<210> SEQ ID NO 57
<211> LENGTH: 8762
<212> TYPE: DNA
<213> ORGANISM: Borrelia afzelii

<400> SEQUENCE: 57

| | | | | | |
|---|---|---|---|---|---|
| gagagtgctg | ttgatggggt | tagcaagtgg | ttagaagaga | tgataaaagc | tgctaaggag | 60 |
| gctgctacaa | agggtggtac | tggtggtggt | agcgaaaaga | ttggggatgt | tggtgctgct | 120 |
| aataatcagg | gtgctgtagc | tgataaggac | agtgttaagg | ggattgcgaa | ggggataaag | 180 |
| gggattgttg | atgctgctgg | gaaggctttt | ggtaaggatg | gtaatgcgct | gacaggtgta | 240 |
| aaagaagttg | ctgatgaggc | tggggctaac | gaggatgcgg | ggaagttgtt | tgctggtaat | 300 |
| gctggtaatg | ctgctgctgc | tgacattgcg | aaggcggctg | gtgctgttac | tgcggttagt | 360 |
| ggggagcaga | tactgaaagc | tattgttgat | ggtgctggtg | gtgcggctca | agatggtaaa | 420 |
| aaggctgcga | aggctaagaa | tccgattgca | gctgcgattg | ggctgatgc | tgctggtgcg | 480 |
| gattttggtg | atgatatgaa | gaagagtgat | aagattgctg | cggctattgt | tttgaggggg | 540 |
| gtggctaaga | gtgaaaagtt | tgctgttgct | aatgctgcta | agaaggagag | tgtgaagagt | 600 |
| gctgtggaga | gtgctgttga | tgaggttagc | aagtggttag | aagagatgat | aaaagctgct | 660 |
| ggtgggggctg | ctaagggtgg | tactggtggt | aataacgaaa | agattgggga | ttctgataat | 720 |
| aataagggtg | ctgtagctga | taaggacagt | gttaagggga | ttgcgaaggg | gataaagggg | 780 |
| attgttgatg | ctgctgggaa | ggcttttggt | aaggatggta | atgcgctgaa | ggatgttgca | 840 |
| aaagttgctg | atgatgcggc | tggggctaac | gcgaatgcag | ggaagttgtt | tgctggtaat | 900 |
| gctgctggtg | gtgccgctga | tgctgatgat | gctaacattg | cgaaggcggc | tggtgctgtt | 960 |
| agtgcggtta | gtggggagca | gatactgaaa | gctattgttg | atgctgctgg | tgctgctgct | 1020 |
| aatcaggatg | gtaagaaggc | tgcggatgct | aagaatccga | ttgcagctgc | gattgggact | 1080 |
| aatgatgatg | gggcggagtt | taaggatgga | atgaagaaga | gtgataatat | tgctgcagct | 1140 |
| attgttttga | ggggggtggc | taagggtgga | agtttgctg | ttgctaatgc | tgctaatgat | 1200 |
| agtaaggcga | gtgtgaagag | tgctgtggag | agtgctgttg | atgaggttag | caagtggtta | 1260 |
| gaagagatga | taacagctgc | tggtgaggct | gctacaaagg | gtggtgatgc | tggtggtggt | 1320 |
| gctgataaga | ttggggatgt | tggtgctgct | aataatggtg | ctgtagctga | tgcgagcagt | 1380 |
| gttaaggaga | ttgcgaaggg | gataaagggg | attgttgatg | ctgctgggaa | ggcttttggc | 1440 |
| aaggatggta | atgcgctgaa | ggatgttgca | aagttgctg | atgataagaa | ggaggcgggg | 1500 |
| aagttgtttg | ctggtaatgc | tggtggtgct | gttgctgatg | ctgctgcgat | tgggaaggcg | 1560 |
| gctggtgctg | ttactgcggt | tagtggggag | cagatactga | aagctattgt | tgatgctgct | 1620 |
| ggtggtgcgg | atcaggcggg | taagaaggct | gatgcggcta | agaatccgat | tgcagctgcg | 1680 |
| attgggctg | atgctgctgg | tgctggtgcg | gattttggta | atgatatgaa | gaagagaaat | 1740 |
| gataagattg | ttgcggctat | tgttttgagg | ggggtggcta | aggatggaaa | gtttgctgct | 1800 |
| gctgctaatg | atgataatag | taaggcgagt | gtgaagagtg | ctgtggagag | tgctgttgat | 1860 |

```
gaggttagca agtggttaga agagatgata acagctgctg atgggctgc taaaggtggt    1920
actggtggta atagcgaaaa gattggggat gctggtgata ataataatgg tgctgtagct    1980
gatgagaaca gtgttaagga gattgcaaag gggataaagg ggattgttgc ggctgctggg    2040
aaggcttttg gcaaggatgg caaggatggt gatgcgctga aggatgttga aacagttgct    2100
gctgagaatg aggctaacaa ggatgcgggg aagttgtttg ctggtgctaa tggtaatgct    2160
ggtgctgctg ttggtgacat tgcgaaggcg gctgctgctg ttactgcggt tagtggggag    2220
cagatactaa aagctattgt tgatgctgct ggtgatgcgg atcaggcggg taagaaggct    2280
gctgaggcta agaatccgat tgcagctgcg attgggctga atgctgctga taatgcggcg    2340
gcgtttggta aggatgagat gaagaagagt gataagattg ctgcagctat tgttttgagg    2400
ggggtggcta aggatggaaa gtttgctgtt gctaatgcta atgatgataa gaaggcgagt    2460
gtgaagagtg ctgtggagag tgctgtggat gaggttagca agtggttaga agagatgata    2520
acagctgcta aggaggctgc tacaaagggt ggtactggtg gtaataacga aaagattgga    2580
gattctgatg ctaataatgg tgcgaaggct gatgcgagca gtgttaatgg gattgcgaat    2640
gggataaagg ggattgttga tgctgctggg aaggcttttg gcaaggaggg tagtgcgctg    2700
aaggatgtta aaacagttgc tgctgagaat gaggctaaca aggatgcggg gaagttgttt    2760
gctggtaaga atggtaatgc tgatgctgct gatgctgctg acattgcgaa ggcggctggt    2820
gctgttagtg cggttagtgg ggagcagata ctgaaagcta ttgttgatgg tgctggtgat    2880
gcagctaatc aggcgggtaa aaaggctgct gaggctaaga atccgattgc ggctgcgatt    2940
gggactaatg aagctgggc ggagtttggt gatgatatga agaagagaaa tgataagatt    3000
gctgcggcta ttgttttgag gggggtggct aaggatggaa agtttgctgt tgctaatgct    3060
gctgctgata atagtaaggc gagtgtgaag agtgctgttg atgaggttag caagtggtta    3120
gaagagatga taaaggctgc tgatgaggct gctacaaagg gtggtgatgc tggtggtggt    3180
gctgataaga ttggggatgc tggtgataag ggtgctgtag ctgatgcgag cagtgttaag    3240
gagattgcga atgggataaa ggggattgtt gatgctgctg gaaggctttt tggcaaggag    3300
ggtagtgcgc tgaaggatgt taaaacagtt gctgctgaga atgaggctaa caaggatgcg    3360
gggaagttgt ttgctggtaa tgctggtaat ggtgctgctg atgacattgc gaaggcggct    3420
gctgctgtta ctgcggttag tggggagcag atactgaaag ctattgttga tgctgctggt    3480
gataaggcta atcaggatgg taaaaaggct gcggatgcta agaatccgat tgcggctgcg    3540
attgggctg ctgatgctgg tgctgcggcg gcgtttaatg agaatgatat gaagaagagt    3600
gataagattg ctgcagctat tgttttgagg ggggtggcta aggatggaaa gtttgctgct    3660
gctgatgctg atgctaataa tagtaaggcg agcgtgaaga gtgctgttgg tgaggttagc    3720
aagtggttag aagagatgat aaaagctgct ggtgaggctg caaaagttgg tggtactggt    3780
ggtagcgaaa agattgggga tgctgataat aataagggtg ctgtagctga tgcgagcagt    3840
gttaatggga ttgcgaatgg gataaagggg attgttgatg ctgctgggaa ggcttttggt    3900
aaggatggtg cgctggcagg tgttgcagct gctgctgaga atgatgataa gaaggatgcg    3960
gggaagttgt ttgctggtaa gaatggtggt gctggtgctg ctgatgcgat tgggaaggcg    4020
gctgctgctg ttactgcggt tagtggggag cagatactga aagctattgt tgatgctgct    4080
ggtgctgcag ctaatcaggc gggtaaaaag gctgcggatg ctaagaatcc gattgcggct    4140
gcgattggga ctgctgatga tggggcggag tttaaggatg atatgaagaa gagtgataat    4200
```

```
attgctgcgg ctattgtttt gagggggtg gctaaggatg gaaagtttgc tgttgctaat    4260
gctgatgata ataaggcgag tgtgaagagt gctgtggaga gtgctgttga tgaggttagc    4320
aagtggttag aagagatgat aacagctgct ggtgaggctg caaaagttgg tgctggtggt    4380
ggtgctgata agattgggga tgctgctaat aatcagggtg cgaaggctga tgagagcagt    4440
gttaatggaa ttgcaaaggg gataaagggg attgttgatg ctgctgggaa ggcttttggc    4500
aaggagggta gtgcgctgaa ggatgttgca aaagttgctg atgatgataa caaggatgcg    4560
gggaagttgt ttgctggtaa tgctggtggt ggtgctggtg ctgatattgc gaaggcggct    4620
gctgctgtta ctgcgttag tggggagcag atactgaaag ctattgttga tgctgctggt    4680
gctgcggatc aggcgggtgc agctgctggt gcggctaaga atccgattgc ggctgcgatt    4740
ggggctgatg ctggtgctgc ggaggagttt aaggatgaga tgaagaagag tgataagatt    4800
gctgcggcta ttgttttgag gggggtggct aagggtggaa agtttgctgt tgctgctaat    4860
gatgctgcaa atgtgaagag tgctgtggag agtgctgttg gtgaggttag cgcatggtta    4920
gaagagatga taacagctgc tagtgaggct gctacaaagg gtggtactgg tggtactggt    4980
ggtgatagtg aaaagattgg ggattctgat gctaataatg gtgctgtagc tgatgcgagc    5040
agtgttaagg agattgcgaa ggggataaag gggattgttg atgctgctgg gaaggctttt    5100
ggtaaggatg gtaatgcgct gaaggatgtt gcagaagttg ctgatgatga ggctaacgcg    5160
gatgcgggga agttgtttgc tggtaatgct ggtaatgctc tgctgctga cgttgcgaag    5220
gcggctggtg ctgttactgc ggttagtggg gagcagatac tgaaagctat tgttgatgct    5280
gctggtgctg cggatcaggc gggtgcaaag gctgatgcgg ctaagaatcc gattgcagct    5340
gcgattggga ctaatgaagc tggggcggcg tttaaggatg gaatgaagaa gagaaatgat    5400
aatattgctg cggctattgt tttgagggg gtggctaaga gtggaaagtt tgctgttgct    5460
gctgctgatg ctggtaaggc gagagtgtga agagtgctgt ggagagtgct gttgatgagg    5520
ttagcaagtg gttagaagag atgataacag ctgctagtga ggctgcaaaa gttggtgctg    5580
gtggtgatga taagattggg gattctgcta ataatggtgc tgtagctgat gcgggcagtg    5640
ttaagggaat tgcgaagggg ataaaggga ttgttgatgc tgctgggaag gcttttggta    5700
aggagggtga tgcgctgaag gatgttgcaa aagttgctga tgagaatggg gataacaagg    5760
atgcggggaa gttgtttgct ggtgagaatg taatgctgg tggtgctgct gatgctgaca    5820
ttgcgaaggc ggctgctgct gttactgcgg ttagtgggga gcagatactg aaagctattg    5880
ttgaggctgc tggtgctggt gatgcagcta atcaggcggg taagaaggct gatgaggcta    5940
agaatccgat tgcggctgcg attgggactg atgatgctgg ggcggcgttt ggtcaggatg    6000
atatgaagaa gagaaatgat aatattgctg cggctattgt tttgagggg gtggctaagg    6060
gtggaaagtt tgctgttgct aatgctgcta atgatagtaa ggcgagtgtg aagagtgctg    6120
tggagagtgc tgttgatgag gttagcaagt ggttagaaga gataataaca gctactggga    6180
aggcttttgg taaggatggt aatgcgctgg caggtgttgc aaaagttgct gatgatgagg    6240
ctaacgcgga tgcggggaag ttgtttgctg gtgagaatgg taatgctggt gctgctgcga    6300
ttgggaaggc ggctgctgct gttactgcgg ttagtgggga gcagatactg aaagctattg    6360
ttgatgctgc tggtggtgcg gctcaggtgg gtgctggtgc tggtgcggct acgaatccga    6420
ttgcagctgc gattgggct gctggtgatg gtgcggattt tggtaaggat gagatgaaga    6480
agagaaatga taagattgct gcggctattg ttttgagggg gtggctaag gatggaaagt    6540
tgctgctgc tgctaatgat agtaaggcga gtgtgaagag tgctgtggag agtgctgttg    6600
```

```
atgaggttag caagtggtta gaagagatga taacagctgc tgatgctgct gctgctaaag    6660
ttggcgatgc tggtggtggt gctgataaga ttggggatgt tggtgctgct aataagggtg    6720
cgaaggctga tgcgagcagt gttaaggaga ttgcgaaggg gataaagggg attgttgatg    6780
ctgctgggaa ggcttttggt ggtgatgcgc tgaaggatgt taaagctgct ggtgatgata    6840
acaaggaggc agggaagttg tttgctggtg ctaatggtaa tgctggtgct aatgctgctg    6900
ctgctgatga cattgcgaag gcggctggtg ctgttagtgc ggttagtggg agcagatac    6960 tgaaagctat tgttgaggcg gctggtgctg cggatcaggc gggtgtaaag gctgaggagg    7020
ctaagaatcc gattgcagct gcgattggga ctgatgatgc tggtgcggcg gagtttggtg    7080
agaatgatat gaagaagaat gataatattg ctgcggctat tgttttgagg ggggtggcta    7140
agagtggaaa gtttgctgct aatgctaatg atgctggtaa gaaggagagt gtgaagagtg    7200
ctgtggatga ggctagcaag tggttagaag agatgataac agctgctggt gaggctgcta    7260
caaagggtgg tactggtgaa gctagcgaaa gattgggga tgttggtgat aataatcatg    7320
gtgctgtagc tgatgcggac agtgttaagg ggattgcgaa ggggataaag gggattgttg    7380
atgctgctgg gaaggctttt ggtaaggatg gtgcgctgaa ggatgttgca gctgctgctg    7440
gtgatgaggc taacaaggat gcggggaagt tgtttgctgg tcaggatggt ggtggtgctg    7500
atggtgacat tgcgaaggcg gctgctgctg ttactgcggt tagtggggag cagatactga    7560
aagctattgt tgaggctgct ggtgataagg ctaatcaggt gggtgtaaag gctgctggtg    7620
cggctacgaa tccgattgca gctgcgattg ggactgatga tgataatgcg gcggcgtttg    7680
ataaggatga gatgaagaag agtaatgata agattgctgc ggctattgtt ttgagggggg    7740
tggctaagga tggaaagttt gctgctaatg ctaatgataa tagtaaggcg agtgtgaaga    7800
gtgctgtgga tgaggttagc aagtggttag aagagatgat aacagctgct agtgatgctg    7860
ctacaaaggg tggtactggt gaagctagcg aaaagattgg ggattctgat gctaataagg    7920
gtgctggtgc tggggcggcg tttggtgaga atgatatgaa gaagagaaat gataatattg    7980
ctgcagctat tgttttgagg ggggtggcta aggatgaaa gtttgctgtt aaggaggatt    8040
attgaactca gctttatagg ggaacagcaa ttcgctagaa atgattaaa agcttaact    8100 tcgactggtt cttgccttaa ttttattcct ttgttattat ttatcaatta aattcacttc    8160
ggtttgcttt taaattaatt ctggtatact atgtatacta gatacacaaa ttaaggagaa    8220
gtgaaatgga aaaatagaa aatttaaaa acaaatgtca acataaacta caacataaac    8280
taatcgtatt agtatcaaca ctttgctata taaacaataa aaataaaaaa tattcacaaa    8340
gcaacatcct ttattatttt aatgaaaatt taaaagaaa tgggcaaacc cctattaaaa    8400
taaaaacatt acaaaactat ctttataaac tggaaaaaga atttgaagta caactaatt    8460 attataaaca cttgggggtt aattgtggaa ccgaaattta ctataaactt aaatatcaaa    8520
aacaaaaatg ctatcataaa ataaaccaat attttaaaaa gaaaaagaa attaaattta    8580 acttaagagt aagtgcattt tttaataaaa aacactcaaa aaagggagt gtagaattaa    8640 aggaatgtaa taataataat aataataaag agaaagaaac atcccaaaaa attgaaattt    8700
tacaaacaaa agtctatgcc aaaaaatgta aattttgac aaactactat actaaaattt    8760
ta                                                                  8762
```

<210> SEQ ID NO 58
<211> LENGTH: 606
<212> TYPE: DNA

```
<213> ORGANISM: Borrelia afzelii
<220> FEATURE:
<221> NAME/KEY: CDS
<222> LOCATION: (1)..(606)

<400> SEQUENCE: 58 gag agt gct gtt gat ggg gtt agc aag tgg tta gaa gag atg ata aaa      48
Glu Ser Ala Val Asp Gly Val Ser Lys Trp Leu Glu Glu Met Ile Lys
1               5                   10                  15 gct gct aag gag gct gct aca aag ggt ggt act ggt ggt ggt agc gaa      96
Ala Ala Lys Glu Ala Ala Thr Lys Gly Gly Thr Gly Gly Gly Ser Glu
                20                  25                  30 aag att ggg gat gtt ggt gct gct aat aat cag ggt gct gta gct gat     144
Lys Ile Gly Asp Val Gly Ala Ala Asn Asn Gln Gly Ala Val Ala Asp
            35                  40                  45 aag gac agt gtt aag ggg att gcg aag ggg ata aag ggg att gtt gat     192
Lys Asp Ser Val Lys Gly Ile Ala Lys Gly Ile Lys Gly Ile Val Asp
        50                  55                  60 gct gct ggg aag gct ttt ggt aag gat ggt aat gcg ctg aca ggt gta     240
Ala Ala Gly Lys Ala Phe Gly Lys Asp Gly Asn Ala Leu Thr Gly Val
65                  70                  75                  80 aaa gaa gtt gct gat gag gct ggg gct aac gag gat gcg ggg aag ttg     288
Lys Glu Val Ala Asp Glu Ala Gly Ala Asn Glu Asp Ala Gly Lys Leu
                85                  90                  95 ttt gct ggt aat gct ggt aat gct gct gct gct gac att gcg aag gcg     336
Phe Ala Gly Asn Ala Gly Asn Ala Ala Ala Ala Asp Ile Ala Lys Ala
                100                 105                 110 gct ggt gct gtt act gcg gtt agt ggg gag cag ata ctg aaa gct att     384
Ala Gly Ala Val Thr Ala Val Ser Gly Glu Gln Ile Leu Lys Ala Ile
            115                 120                 125 gtt gat ggt gct ggt ggt gcg gct caa gat ggt aaa aag gct gcg gag     432
Val Asp Gly Ala Gly Gly Ala Ala Gln Asp Gly Lys Lys Ala Ala Glu
        130                 135                 140 gct aag aat ccg att gca gct gcg att ggg gct gat gct gct ggt gcg     480
Ala Lys Asn Pro Ile Ala Ala Ala Ile Gly Ala Asp Ala Ala Gly Ala
145                 150                 155                 160 gat ttt ggt gat gat atg aag aag agt gat aag att gct gcg gct att     528
Asp Phe Gly Asp Asp Met Lys Lys Ser Asp Lys Ile Ala Ala Ala Ile
                165                 170                 175 gtt ttg agg ggg gtg gct aag agt gga aag ttt gct gtt gct aat gct     576
Val Leu Arg Gly Val Ala Lys Ser Gly Lys Phe Ala Val Ala Asn Ala
            180                 185                 190 gct aag aag gag agt gtg aag agt gct gtg                             606
Ala Lys Lys Glu Ser Val Lys Ser Ala Val
        195                 200

<210> SEQ ID NO 59
<211> LENGTH: 202
<212> TYPE: PRT
<213> ORGANISM: Borrelia afzelii

<400> SEQUENCE: 59

Glu Ser Ala Val Asp Gly Val Ser Lys Trp Leu Glu Glu Met Ile Lys
1               5                   10                  15

Ala Ala Lys Glu Ala Ala Thr Lys Gly Gly Thr Gly Gly Gly Ser Glu
                20                  25                  30

Lys Ile Gly Asp Val Gly Ala Ala Asn Asn Gln Gly Ala Val Ala Asp
            35                  40                  45

Lys Asp Ser Val Lys Gly Ile Ala Lys Gly Ile Lys Gly Ile Val Asp
        50                  55                  60
```

```
Ala Ala Gly Lys Ala Phe Gly Lys Asp Gly Asn Ala Leu Thr Gly Val
 65                  70                  75                  80

Lys Glu Val Ala Asp Glu Ala Gly Ala Asn Glu Asp Ala Gly Lys Leu
                 85                  90                  95

Phe Ala Gly Asn Ala Gly Asn Ala Ala Ala Asp Ile Ala Lys Ala
            100                 105                 110

Ala Gly Ala Val Thr Ala Val Ser Gly Glu Gln Ile Leu Lys Ala Ile
        115                 120                 125

Val Asp Gly Ala Gly Gly Ala Gln Asp Gly Lys Lys Ala Ala Glu
    130                 135                 140

Ala Lys Asn Pro Ile Ala Ala Ile Gly Ala Asp Ala Ala Gly Ala
145                 150                 155                 160

Asp Phe Gly Asp Asp Met Lys Lys Ser Asp Lys Ile Ala Ala Ile
                165                 170                 175

Val Leu Arg Gly Val Ala Lys Ser Gly Lys Phe Ala Val Ala Asn Ala
        180                 185                 190

Ala Lys Lys Glu Ser Val Lys Ser Ala Val
        195                 200

<210> SEQ ID NO 60
<211> LENGTH: 621
<212> TYPE: DNA
<213> ORGANISM: Borrelia afzelii
<220> FEATURE:
<221> NAME/KEY: CDS
<222> LOCATION: (1)..(621)

<400> SEQUENCE: 60 gag agt gct gtt gat gag gtt agc aag tgg tta gaa gag atg ata aaa      48
Glu Ser Ala Val Asp Glu Val Ser Lys Trp Leu Glu Glu Met Ile Lys
1               5                  10                  15 gct gct ggt ggg gct gct aag ggt ggt act ggt ggt aat aac gaa aag      96
Ala Ala Gly Gly Ala Ala Lys Gly Gly Thr Gly Gly Asn Asn Glu Lys
            20                  25                  30 att ggg gat tct gat aat aat aag ggt gct gta gct gat aag gac agt     144
Ile Gly Asp Ser Asp Asn Asn Lys Gly Ala Val Ala Asp Lys Asp Ser
        35                  40                  45 gtt aag ggg att gcg aag ggg ata aag ggg att gtt gat gct gct ggg     192
Val Lys Gly Ile Ala Lys Gly Ile Lys Gly Ile Val Asp Ala Ala Gly
    50                  55                  60 aag gct ttt ggt aag gat ggt aat gcg ctg aag gat gtt gca aaa gtt     240
Lys Ala Phe Gly Lys Asp Gly Asn Ala Leu Lys Asp Val Ala Lys Val
65                  70                  75                  80 gct gat gat gcg gct ggg gct aac gcg aat gca ggg aag ttg ttt gct     288
Ala Asp Asp Ala Ala Gly Ala Asn Ala Asn Ala Gly Lys Leu Phe Ala
                85                  90                  95 ggt aat gct gct ggt ggt gcc gct gat gct gat gat gct aac att gcg     336
Gly Asn Ala Ala Gly Gly Ala Ala Asp Ala Asp Asp Ala Asn Ile Ala
            100                 105                 110 aag gcg gct ggt gct gtt agt gcg gtt agt ggg gag cag ata ctg aaa     384
Lys Ala Ala Gly Ala Val Ser Ala Val Ser Gly Glu Gln Ile Leu Lys
        115                 120                 125 gct att gtt gat gct gct ggt gct gct gct aat cag gat ggt aag aag     432
Ala Ile Val Asp Ala Ala Gly Ala Ala Ala Asn Gln Asp Gly Lys Lys
    130                 135                 140 gct gcg gat gct aag aat ccg att gca gct gcg att ggg act aat gat     480
Ala Ala Asp Ala Lys Asn Pro Ile Ala Ala Ala Ile Gly Thr Asn Asp
145                 150                 155                 160 gat ggg gcg gag ttt aag gat gga atg aag aag agt gat aat att gct     528
```

```
                                      -continued
Asp Gly Ala Glu Phe Lys Asp Gly Met Lys Lys Ser Asp Asn Ile Ala
            165                 170                 175 gca gct att gtt ttg agg ggg gtg gct aag ggt gga aag ttt gct gtt      576
Ala Ala Ile Val Leu Arg Gly Val Ala Lys Gly Gly Lys Phe Ala Val
        180                 185                 190 gct aat gct gct aat gat agt aag gcg agt gtg aag agt gct gtg          621
Ala Asn Ala Ala Asn Asp Ser Lys Ala Ser Val Lys Ser Ala Val
        195                 200                 205

<210> SEQ ID NO 61
<211> LENGTH: 207
<212> TYPE: PRT
<213> ORGANISM: Borrelia afzelii

<400> SEQUENCE: 61

Glu Ser Ala Val Asp Glu Val Ser Lys Trp Leu Glu Glu Met Ile Lys
1               5                  10                  15

Ala Ala Gly Gly Ala Ala Lys Gly Gly Thr Gly Gly Asn Asn Glu Lys
            20                  25                  30

Ile Gly Asp Ser Asp Asn Asn Lys Gly Ala Val Ala Asp Lys Asp Ser
        35                  40                  45

Val Lys Gly Ile Ala Lys Gly Ile Lys Gly Ile Val Asp Ala Ala Gly
    50                  55                  60

Lys Ala Phe Gly Lys Asp Gly Asn Ala Leu Lys Asp Val Ala Lys Val
65                  70                  75                  80

Ala Asp Asp Ala Ala Gly Ala Asn Ala Asn Ala Gly Lys Leu Phe Ala
                85                  90                  95

Gly Asn Ala Ala Gly Gly Ala Ala Asp Ala Asp Ala Asn Ile Ala
            100                 105                 110

Lys Ala Ala Gly Ala Val Ser Ala Val Ser Gly Glu Gln Ile Leu Lys
        115                 120                 125

Ala Ile Val Asp Ala Ala Gly Ala Ala Asn Gln Asp Gly Lys Lys
    130                 135                 140

Ala Ala Asp Ala Lys Asn Pro Ile Ala Ala Ile Gly Thr Asn Asp
145                 150                 155                 160

Asp Gly Ala Glu Phe Lys Asp Gly Met Lys Lys Ser Asp Asn Ile Ala
            165                 170                 175

Ala Ala Ile Val Leu Arg Gly Val Ala Lys Gly Gly Lys Phe Ala Val
        180                 185                 190

Ala Asn Ala Ala Asn Asp Ser Lys Ala Ser Val Lys Ser Ala Val
    195                 200                 205

<210> SEQ ID NO 62
<211> LENGTH: 618
<212> TYPE: DNA
<213> ORGANISM: Borrelia afzelii
<220

```
                   35                  40                  45
gcg agc agt gtt aag gag att gcg aag ggg ata aag ggg att gtt gat      192
Ala Ser Ser Val Lys Glu Ile Ala Lys Gly Ile Lys Gly Ile Val Asp
        50                  55                  60 gct gct ggg aag gct ttt ggc aag gat ggt aat gcg ctg aag gat gtt      240
Ala Ala Gly Lys Ala Phe Gly Lys Asp Gly Asn Ala Leu Lys Asp Val
 65                  70                  75                  80 gca gaa gtt gct gat gat aag aag gag gcg ggg aag ttg ttt gct ggt      288
Ala Glu Val Ala Asp Asp Lys Lys Glu Ala Gly Lys Leu Phe Ala Gly
                 85                  90                  95 aat gct ggt ggt gct gtt gct gat gct gct gcg att ggg aag gcg gct      336
Asn Ala Gly Gly Ala Val Ala Asp Ala Ala Ala Ile Gly Lys Ala Ala
            100                 105                 110 ggt gct gtt act gcg gtt agt ggg gag cag ata ctg aaa gct att gtt      384
Gly Ala Val Thr Ala Val Ser Gly Glu Gln Ile Leu Lys Ala Ile Val
        115                 120                 125 gat gct gct ggt ggt gcg gat cag gcg ggt aag aag gct gat gcg gct      432
Asp Ala Ala Gly Gly Ala Asp Gln Ala Gly Lys Lys Ala Asp Ala Ala
130                 135                 140 aag aat ccg att gca gct gcg att ggg gct gat gct gct ggt gct ggt      480
Lys Asn Pro Ile Ala Ala Ala Ile Gly Ala Asp Ala Ala Gly Ala Gly
145                 150                 155                 160 gcg gat ttt ggt aat gat atg aag aag aga aat gat aag att gtt gcg      528
Ala Asp Phe Gly Asn Asp Met Lys Lys Arg Asn Asp Lys Ile Val Ala
                165                 170                 175 gct att gtt ttg agg ggg gtg gct aag gat gga aag ttt gct gct gct      576
Ala Ile Val Leu Arg Gly Val Ala Lys Asp Gly Lys Phe Ala Ala Ala
            180                 185                 190 gct aat gat gat aat agt aag gcg agt gtg aag agt gct gtg              618
Ala Asn Asp Asp Asn Ser Lys Ala Ser Val Lys Ser Ala Val
        195                 200                 205

<210> SEQ ID NO 63
<211> LENGTH: 206
<212> TYPE: PRT
<213> ORGANISM: Borrelia afzelii

<400> SEQUENCE: 63

Glu Ser Ala Val Asp Glu Val Ser Lys Trp Leu Glu Glu Met Ile Thr
 1               5                  10                  15

Ala Ala Gly Glu Ala Ala Thr Lys Gly Gly Asp Ala Gly Gly Gly Ala
            20                  25                  30

Asp Lys Ile Gly Asp Val Gly Ala Ala Asn Asn Gly Ala Val Ala Asp
        35                  40                  45

Ala Ser Ser Val Lys Glu Ile Ala Lys Gly Ile Lys Gly Ile Val Asp
    50                  55                  60

Ala Ala Gly Lys Ala Phe Gly Lys Asp Gly Asn Ala Leu Lys Asp Val
65                  70                  75                  80

Ala Glu Val Ala Asp Asp Lys Lys Glu Ala Gly Lys Leu Phe Ala Gly
                85                  90                  95

Asn Ala Gly Gly Ala Val Ala Asp Ala Ala Ala Ile Gly Lys Ala Ala
            100                 105                 110

Gly Ala Val Thr Ala Val Ser Gly Glu Gln Ile Leu Lys Ala Ile Val
        115                 120                 125

Asp Ala Ala Gly Gly Ala Asp Gln Ala Gly Lys Lys Ala Asp Ala Ala
    130                 135                 140

Lys Asn Pro Ile Ala Ala Ala Ile Gly Ala Asp Ala Ala Gly Ala Gly
145                 150                 155                 160
```

```
Ala Asp Phe Gly Asn Asp Met Lys Lys Arg Asn Asp Lys Ile Val Ala
                165                 170                 175

Ala Ile Val Leu Arg Gly Val Ala Lys Asp Gly Lys Phe Ala Ala Ala
            180                 185                 190

Ala Asn Asp Asp Asn Ser Lys Ala Ser Val Lys Ser Ala Val
        195                 200                 205
```

<210> SEQ ID NO 64
<211> LENGTH: 630
<212> TYPE: DNA
<213> ORGANISM: Borrelia afzelii
<220> FEATURE:
<221> N

```
<211> LENGTH: 210
<212> TYPE: PRT
<213> ORGANISM: Borrelia afzelii

<400> SEQUENCE: 65

Glu Ser Ala Val Asp Gl

| | | | | | | | | | | | | | | | | |
|---|---|---|---|---|---|---|---|---|---|---|---|---|---|---|---|---|
| gtt | gct | gct | gag | aat | gag | gct | aac | aag | gat | gcg | ggg | aag | ttg | ttt | gct | 288 |
| Val | Ala | Ala | Glu | Asn | Glu | Ala | Asn | Lys | Asp | Ala | Gly | Lys | Leu | Phe | Ala | |
| | | | 85 | | | | | 90 | | | | | 95 | | | |
| ggt | aag | aat | ggt | aat | gct | gat | gct | gct | gat | gct | gct | gac | att | gcg | aag | 336 |
| Gly | Lys | Asn | Gly | Asn | Ala | Asp | Ala | Ala | Asp | Ala | Ala | Asp | Ile | Ala | Lys | |
| | | | 100 | | | | 105 | | | | | 110 | | | | |
| gcg | gct | ggt | gct | gtt | agt | gcg | gtt | agt | ggg | gag | cag | ata | ctg | aaa | gct | 384 |
| Ala | Ala | Gly | Ala | Val | Ser | Ala | Val | Ser | Gly | Glu | Gln | Ile | Leu | Lys | Ala | |
| | | 115 | | | | | 120 | | | | | 125 | | | | |
| att | gtt | gat | ggt | gct | ggt | gat | gca | gct | aat | cag | gcg | ggt | aaa | aag | gct | 432 |
| Ile | Val | Asp | Gly | Ala | Gly | Asp | Ala | Ala | Asn | Gln | Ala | Gly | Lys | Lys | Ala | |
| | 130 | | | | | 135 | | | | | 140 | | | | | |
| gct | gag | gct | aag | aat | ccg | att | gcg | gct | gcg | att | ggg | act | aat | gaa | gct | 480 |
| Ala | Glu | Ala | Lys | Asn | Pro | Ile | Ala | Ala | Ala | Ile | Gly | Thr | Asn | Glu | Ala | |
| 145 | | | | | 150 | | | | | 155 | | | | | 160 | |
| ggg | gcg | gag | ttt | ggt | gat | gat | atg | aag | aag | aga | aat | gat | aag | att | gct | 528 |
| Gly | Ala | Glu | Phe | Gly | Asp | Asp | Met | Lys | Lys | Arg | Asn | Asp | Lys | Ile | Ala | |
| | | | | 165 | | | | | 170 | | | | | 175 | | |
| gcg | gct | att | gtt | ttg | agg | ggg | gtg | gct | aag | gat | gga | aag | ttt | gct | gtt | 576 |
| Ala | Ala | Ile | Val | Leu | Arg | Gly | Val | Ala | Lys | Asp | Gly | Lys | Phe | Ala | Val | |
| | | | 180 | | | | | 185 | | | | | 190 | | | |
| gct | aat | gct | gct | gct | gat | aat | agt | aag | gcg | agt | gtg | | | | | 612 |
| Ala | Asn | Ala | Ala | Ala | Asp | Asn | Ser | Lys | Ala | Ser | Val | | | | | |
| | | | 195 | | | | | 200 | | | | | | | | |

```
<210> SEQ ID NO 67
<211> LENGTH: 204
<212> TYPE: PRT
<213> ORGANISM: Borrelia afzelii

<400> S

<210> SEQ ID NO 68
<211> LENGTH: 609
<212> TYPE: DNA
<213> ORGANISM: Borrelia afzelii
<220> FEATURE:
<221> NAME/KEY: CDS
<222> LOCATION: (1)..(609)

<400> SEQUENCE: 68

| | | | | | | | | | | | | | | | | |
|---|---|---|---|---|---|---|---|---|---|---|---|---|---|---|---|---|
| aag | agt | gct | gtt | gat | gag | gtt | agc | aag | tgg | tta | gaa | gag | atg | ata | aag | 48 |
| Lys | Ser | Ala | Val | Asp | Glu | Val | Ser | Lys | Trp | Leu | Glu | Glu | Met | Ile | Lys | |
| 1 | | | | 5 | | | | | 10 | | | | | 15 | | |
| gct | gct | ggt | gag | gct | gct | aca | aag | ggt | ggt | gat | gct | ggt | ggt | ggt | gct | 96 |
| Ala | Ala | Gly | Glu | Ala | Ala | Thr | Lys | Gly | Gly | Asp | Ala | Gly | Gly | Gly | Ala | |
| | | | 20 | | | | | 25 | | | | | 30 | | | |
| gat | aag | att | ggg | gat | gct | ggt | gat | aag | ggt | gct | gta | gct | gat | gcg | agc | 144 |
| Asp | Lys | Ile | Gly | Asp | Ala | Gly | Asp | Lys | Gly | Ala | Val | Ala | Asp | Ala | Ser | |
| | | 35 | | | | | 40 | | | | | 45 | | | | |
| agt | gtt | aag | gag | att | gcg | aat | ggg | ata | aag | ggg | att | gtt | gat | gct | gct | 192 |
| Ser | Val | Lys | Glu | Ile | Ala | Asn | Gly | Ile | Lys | Gly | Ile | Val | Asp | Ala | Ala | |
| 50 | | | | | 55 | | | | | 60 | | | | | | |
| ggg | aag | gct | ttt | ggc | aag | gag | ggt | agt | gcg | ctg | aag | gat | gtt | aaa | aca | 240 |
| Gly | Lys | Ala | Phe | Gly | Lys | Glu | Gly | Ser | Ala | Leu | Lys | Asp | Val | Lys | Thr | |
| 65 | | | | 70 | | | | | 75 | | | | | 80 | | |
| gtt | gct | gct | gag | aat | gag | gct | aac | aag | gat | gcg | ggg | aag | ttg | ttt | gct | 288 |
| Val | Ala | Ala | Glu | Asn | Glu | Ala | Asn | Lys | Asp | Ala | Gly | Lys | Leu | Phe | Ala | |
| | | | | 85 | | | | | 90 | | | | | 95 | | |
| ggt | aat | gct | ggt | aat | ggt | gct | gct | gat | gac | att | gcg | aag | gcg | gct | gct | 336 |
| Gly | Asn | Ala | Gly | Asn | Gly | Ala | Ala | Asp | Asp | Ile | Ala | Lys | Ala | Ala | Ala | |
| | | | 100 | | | | | 105 | | | | | 110 | | | |
| gct | gtt | act | gcg | gtt | agt | ggg | gag | cag | ata | ctg | aaa | gct | att | gtt | gat | 384 |
| Ala | Val | Thr | Ala | Val | Ser | Gly | Glu | Gln | Ile | Leu | Lys | Ala | Ile | Val | Asp | |
| | | 115 | | | | | 120 | | | | | 125 | | | | |
| gct | gct | ggt | gat | aag | gct | aat | cag | gat | ggt | aaa | aag | gct | gcg | gat | gct | 432 |
| Ala | Ala | Gly | Asp | Lys | Ala | Asn | Gln | Asp | Gly | Lys | Lys | Ala | Ala | Asp | Ala | |
| 130 | | | | | 135 | | | | | 140 | | | | | | |
| aag | aat | ccg | att | gcg | gct | gcg | att | ggg | gct | gct | gat | gct | ggt | gct | gcg | 480 |
| Lys | Asn | Pro | Ile | Ala | Ala | Ala | Ile | Gly | Ala | Ala | Asp | Ala | Gly | Ala | Ala | |
| 145 | | | | 150 | | | | | 155 | | | | | 160 | | |
| gcg | gcg | ttt | aat | gag | aat | gat | atg | aag | aag | agt | gat | aag | att | gct | gca | 528 |
| Ala | Ala | Phe | Asn | Glu | Asn | Asp | Met | Lys | Lys | Ser | Asp | Lys | Ile | Ala | Ala | |
| | | | | 165 | | | | | 170 | | | | | 175 | | |
| gct | att | gtt | ttg | agg | ggg | gtg | gct | aag | gat | gga | aag | ttt | gct | gct | gct | 576 |
| Ala | Ile | Val | Leu | Arg | Gly | Val | Ala | Lys | Asp | Gly | Lys | Phe | Ala | Ala | Ala | |
| | | | 180 | | | | | 185 | | | | | 190 | | | |
| gat | gct | gat | gct | aat | aat | agt | aag | gcg | agc | gtg | | | | | | 609 |
| Asp | Ala | Asp | Ala | Asn | Asn | Ser | Lys | Ala | Ser | Val | | | | | | |
| | | 195 | | | | | 200 | | | | | | | | | |

<210> SEQ ID NO 69
<211> LENGTH: 203
<212> TYPE: PRT
<213> ORGANISM: Borrelia afzelii

<400> SEQUENCE: 69

Lys Ser Ala Val Asp Glu Val Ser Lys Trp Leu Glu Glu Met Ile Lys
1               5                   10                  15

Ala Ala Gly Glu Ala Ala Thr Lys Gly Gly Asp Ala Gly Gly Gly Ala
            20                  25                  30

Asp Lys Ile Gly Asp Ala Gly Asp Lys Gly Ala Val Ala Asp Ala Ser
        35                  40                  45

```
Ser Val Lys Glu Ile Ala Asn Gly Ile Lys Gly Ile Val Asp Ala Ala
    50                  55                  60

Gly Lys Ala Phe Gly Lys Glu Gly Ser Ala Leu Lys Asp Val Lys Thr
65                  70                  75                  80

Val Ala Ala Glu Asn Glu Ala Asn Lys Asp Ala Gly Lys Leu Phe Ala
                85                  90                  95

Gly Asn Ala Gly Asn Gly Ala Ala Asp Asp Ile Ala Lys Ala Ala Ala
                100                 105                 110

Ala Val Thr Ala Val Ser Gly Glu Gln Ile Leu Lys Ala Ile Val Asp
            115                 120                 125

Ala Ala Gly Asp Lys Ala Asn Gln Asp Gly Lys Lys Ala Ala Asp Ala
        130                 135                 140

Lys Asn Pro Ile Ala Ala Ile Gly Ala Ala Asp Ala Gly Ala Ala
145                 150                 155                 160

Ala Ala Phe Asn Glu Asn Asp Met Lys Lys Ser Asp Lys Ile Ala Ala
                165                 170                 175

Ala Ile Val Leu Arg Gly Val Ala Lys Asp Gly Lys Phe Ala Ala Ala
                180                 185                 190

Asp Ala Asp Ala Asn Asn Ser Lys Ala Ser Val
            195                 200

<210> SEQ ID NO 70
<211> LENGTH: 600
<212> TYPE: DNA
<213> ORGANISM: Borrelia afzelii
<220> FEATURE:
<221> NAME/KEY: CDS
<222> LOCATION: (1)..(600)

<400> SEQUENCE: 70 aag agt gct gtt ggt gag gtt agc aag tgg tta gaa gag atg ata aaa      48
Lys Ser Ala Val Gly Glu Val Ser Lys Trp Leu Glu Glu Met Ile Lys
1               5                   10                  15 gct gct ggt gag gct gca aaa gtt ggt ggt act ggt ggt agc gaa aag      96
Ala Ala Gly Glu Ala Ala Lys Val Gly Gly Thr Gly Gly Ser Glu Lys
            20                  25                  30 att ggg gat gct gat aat aat aag ggt gct gta gct gat gcg agc agt     144
Ile Gly Asp Ala Asp Asn Asn Lys Gly Ala Val Ala Asp Ala Ser Ser
        35                  40                  45 gtt aat ggg att gcg aat ggg ata aag ggg att gtt gat gct gct ggg     192
Val Asn Gly Ile Ala Asn Gly Ile Lys Gly Ile Val Asp Ala Ala Gly
    50                  55                  60 aag gct ttt ggt aag gat ggt gcg ctg gca ggt gtt gca gct gct gct     240
Lys Ala Phe Gly Lys Asp Gly Ala Leu Ala Gly Val Ala Ala Ala Ala
65                  70                  75                  80 gag aat gat gat aag aag gat gcg ggg aag ttg ttt gct ggt aag aat     288
Glu Asn Asp Asp Lys Lys Asp Ala Gly Lys Leu Phe Ala Gly Lys Asn
                85                  90                  95 ggt ggt gct ggt gct gct gat gcg att ggg aag gcg gct gct gct gtt     336
Gly Gly Ala Gly Ala Ala Asp Ala Ile Gly Lys Ala Ala Ala Ala Val
                100                 105                 110 act gcg gtt agt ggg gag cag ata ctg aaa gct att gtt gat gct gct     384
Thr Ala Val Ser Gly Glu Gln Ile Leu Lys Ala Ile Val Asp Ala Ala
            115                 120                 125 ggt gct gca gct aat cag gcg ggt aaa aag gct gcg gat gct aag aat     432
Gly Ala Ala Ala Asn Gln Ala Gly Lys Lys Ala Ala Asp Ala Lys Asn
        130                 135                 140 ccg att gcg gct gcg att ggg act gct gat gat ggg gcg gag ttt aag     480
```

```
Pro Ile Ala Ala Ala Ile Gly Thr Ala Asp Asp Gly Ala Glu Phe Lys
145                 150                 155                 160 gat gat atg aag aag agt gat aat att gct gcg gct att gtt ttg agg     528
Asp Asp Met Lys Lys Ser Asp Asn Ile Ala Ala Ala Ile Val Leu Arg
                165                 170                 175 ggg gtg gct aag gat gga aag ttt gct gtt gct aat gct gat gat aat     576
Gly Val Ala Lys Asp Gly Lys Phe Ala Val Ala Asn Ala Asp Asp Asn
            180                 185                 190 aag gcg agt gtg aag agt gct gtg                                     600
Lys Ala Ser Val Lys Ser Ala Val
        195                 200
```

<210> SEQ ID NO 71
<211> LENGTH: 200
<212> TYPE: PRT
<213> ORGANISM: Borrelia afzelii

<400> SEQUENCE: 71

```
Lys Ser Ala Val Gly Glu Val Ser Lys Trp Leu Glu Glu Met Ile Lys
1               5                   10                  15

Ala Ala Gly Glu Ala Ala Lys Val Gly Gly Thr Gly Gly Ser Glu Lys
            20                  25                  30

Ile Gly Asp Ala Asp Asn Asn Lys Gly Ala Val Ala Asp Ala Ser Ser
        35                  40                  45

Val Asn Gly Ile Ala Asn Gly Ile Lys Gly Ile Val Asp Ala Ala Gly
50                  55                  60

Lys Ala Phe Gly Lys Asp Gly Ala Leu Ala Gly Val Ala Ala Ala Ala
65                  70                  75                  80

Glu Asn Asp Asp Lys Lys Asp Ala Gly Lys Leu Phe Ala Gly Lys Asn
                85                  90                  95

Gly Gly Ala Gly Ala Ala Asp Ala Ile Gly Lys Ala Ala Ala Ala Val
            100                 105                 110

Thr Ala Val Ser Gly Glu Gln Ile Leu Lys Ala Ile Val Asp Ala Ala
        115                 120                 125

Gly Ala Ala Ala Asn Gln Ala Gly Lys Lys Ala Ala Asp Ala Lys Asn
    130                 135                 140

Pro Ile Ala Ala Ala Ile Gly Thr Ala Asp Asp Gly Ala Glu Phe Lys
145                 150                 155                 160

Asp Asp Met Lys Lys Ser Asp Asn Ile Ala Ala Ile Val Leu Arg
                165                 170                 175

Gly Val Ala Lys Asp Gly Lys Phe Ala Val Ala Asn Ala Asp Asp Asn
            180                 185                 190

Lys Ala Ser Val Lys Ser Ala Val
        195                 200
```

<210> SEQ ID NO 72
<211> LENGTH: 592
<212> TYPE: DNA
<213> ORGANISM: Borrelia afzelii
<220> FEATURE:
<221> NAME/KEY: CDS
<222> LOCATION: (1)..(591)

<400> SEQUENCE: 72

```
gag agt gct gtt gat gag gtt agc aag tgg tta gaa gag atg ata aca      48
Glu Ser Ala Val Asp Glu Val Ser Lys Trp Leu Glu Glu Met Ile Thr
1               5                   10                  15 gct gct ggt gag gct gca aaa gtt ggt gct ggt ggt ggt gct gat aag      96
Ala Ala Gly Glu Ala Ala Lys Val Gly Ala Gly Gly Gly Ala Asp Lys
```

```
att ggg gat gct gct aat aat cag ggt gcg aag gct gat gag agc agt      144
Ile Gly Asp Ala Ala Asn Asn Gln Gly Ala Lys Ala Asp Glu Ser Ser
         35                  40                  45 gtt aat gga att gca aag ggg ata aag ggg att gtt gat gct gct ggg      192
Val Asn Gly Ile Ala Lys Gly Ile Lys Gly Ile Val Asp Ala Ala Gly
 50                  55                  60 aag gct ttt ggc aag gag ggt agt gcg ctg aag gat gtt gca aaa gtt      240
Lys Ala Phe Gly Lys Glu Gly Ser Ala Leu Lys Asp Val Ala Lys Val
 65                  70                  75                  80 gct gat gat gat aac aag gat gcg ggg aag ttg ttt gct ggt aat gct      288
Ala Asp Asp Asp Asn Lys Asp Ala Gly Lys Leu Phe Ala Gly Asn Ala
                 85                  90                  95 ggt ggt ggt gct ggt gct gat att gcg aag gcg gct gct gtt act           336
Gly Gly Gly Ala Gly Ala Asp Ile Ala Lys Ala Ala Ala Val Thr
        100                 105                 110 gcg gtt agt ggg gag cag ata ctg aaa gct att gtt gat gct gct ggt      384
Ala Val Ser Gly Glu Gln Ile Leu Lys Ala Ile Val Asp Ala Ala Gly
        115                 120                 125 gct gcg gat cag gcg ggt gca gct gct ggt gcg gct aag aat ccg att      432
Ala Ala Asp Gln Ala Gly Ala Ala Ala Gly Ala Ala Lys Asn Pro Ile
130                 135                 140 gcg gct gcg att ggg gct gat gct ggt gct gcg gag gag ttt aag gat      480
Ala Ala Ala Ile Gly Ala Asp Ala Gly Ala Ala Glu Glu Phe Lys Asp
145                 150                 155                 160 gag atg aag aag agt gat aag att gct gcg gct att gtt ttg agg ggg      528
Glu Met Lys Lys Ser Asp Lys Ile Ala Ala Ala Ile Val Leu Arg Gly
                165                 170                 175 gtg gct aag ggt gga aag ttt gct gtt gct gct aat gat gct gca aat      576
Val Ala Lys Gly Gly Lys Phe Ala Val Ala Ala Asn Asp Ala Ala Asn
        180                 185                 190 gtg aag agt gct gtg g                                                 592
Val Lys Ser Ala Val
        195
```

<210> SEQ ID NO 73
<211> LENGTH: 197
<212> TYPE: PRT
<213> ORGANISM: Borrelia afzelii

<400> SEQUENCE: 73

```
Glu Ser Ala Val Asp Glu Val Ser Lys Trp Leu Glu Glu Met Ile Thr
 1               5                  10                  15

Ala Ala Gly Glu Ala Ala Lys Val Gly Ala Gly Gly Ala Asp Lys
            20                  25                  30

Ile Gly Asp Ala Ala Asn Asn Gln Gly Ala Lys Ala Asp Glu Ser Ser
        35                  40                  45

Val Asn Gly Ile Ala Lys Gly Ile Lys Gly Ile Val Asp Ala Ala Gly
 50                  55                  60

Lys Ala Phe Gly Lys Glu Gly Ser Ala Leu Lys Asp Val Ala Lys Val
 65                  70                  75                  80

Ala Asp Asp Asp Asn Lys Asp Ala Gly Lys Leu Phe Ala Gly Asn Ala
                 85                  90                  95

Gly Gly Gly Ala Gly Ala Asp Ile Ala Lys Ala Ala Ala Val Thr
        100                 105                 110

Ala Val Ser Gly Glu Gln Ile Leu Lys Ala Ile Val Asp Ala Ala Gly
        115                 120                 125

Ala Ala Asp Gln Ala Gly Ala Ala Ala Gly Ala Ala Lys Asn Pro Ile
```

```
                    130                 135                 140
Ala Ala Ala Ile Gly Ala Asp Ala Gly Ala Ala Glu Glu Phe Lys Asp
145                 150                 155                 160

Glu Met Lys Lys Ser Asp Lys Ile Ala Ala Ile Val Leu Arg Gly
                165                 170                 175

Val Ala Lys Gly Gly Lys Phe Ala Val Ala Ala Asn Asp Ala Ala Asn
                180                 185                 190

Val Lys Ser Ala Val
            195

<210> SEQ ID NO 74
<211> LENGTH: 597
<212> TYPE: DNA
<213> ORGANISM: Borrelia afzelii
<220> FEATURE:
<221> NAME/KEY: CD
<211> LENGTH: 199
<212> TYPE: PRT
<213> ORGANISM: Borrelia afzelii

<400> SEQUENCE: 75

```
Glu Ser Ala Val Gly Glu Val Ser Ala Trp Leu Glu Glu Met Ile Thr
1               5                   10                  15

Ala Ala Ser Glu Ala Ala Thr Lys Gly Gly Thr Gly Thr Gly Gly
            20                  25                  30

Asp Ser Glu Lys Ile Gly Asp Ser Asp Ala Asn Asn Gly Ala Val Ala
        35                  40                  45

Asp Ala Ser Ser Val Lys Glu Ile Ala Lys Gly Ile Lys Gly Ile Val
50                  55                  60

Asp Ala Ala Gly Lys Ala Phe Gly Lys Asp Gly Asn Ala Leu Lys Asp
65                  70                  75                  80

Val Ala Glu Val Ala Asp Asp Glu Ala Asn Ala Asp Ala Gly Lys Leu
                85                  90                  95

Phe Ala Gly Asn Ala Gly Asn Ala Ala Ala Asp Val Ala Lys Ala
                100                 105                 110

Ala Gly Ala Val Thr Ala Val Ser Gly Glu Gln Ile Leu Lys Ala Ile
            115                 120                 125

Val Asp Ala Ala Gly Ala Ala Asp Gln Ala Gly Ala Lys Ala Asp Ala
130                 135                 140

Ala Lys Asn Pro Ile Ala Ala Ala Ile Gly Thr Asn Glu Ala Gly Ala
145                 150                 155                 160

Ala Phe Lys Asp Gly Met Lys Lys Arg Asn Asp Asn Ile Ala Ala Ala
                165                 170                 175

Ile Val Leu Arg Gly Val Ala Lys Ser Gly Lys Phe Ala Val Ala Ala
                180                 185                 190

Ala Asp Ala Gly Lys Ala Arg
            195
```

<210> SEQ ID NO 76
<211> LENGTH: 621
<212> TYPE: DNA
<213> ORGANISM: Borrelia afzelii
<220> FEATURE:
<221> NAME/KEY: CDS
<222> LOCATION: (1)..(621)

<400> SEQUENCE: 76

```
gag agt gct gtt gat gag gtt agc aag tgg tta gaa gag atg ata aca    48
Glu Ser Ala Val Asp Glu Val Ser Lys Trp Leu Glu Glu Met Ile Thr
1               5                   10                  15 gct gct agt gag gct gca aaa gtt ggt gct ggt ggt gat gat aag att    96
Ala Ala Ser Glu Ala Ala Lys Val Gly Ala Gly Gly Asp Asp Lys Ile
            20                  25                  30 ggg gat tct gct aat aat ggt gct gta gct gat gcg ggc agt gtt aag   144
Gly Asp Ser Ala Asn Asn Gly Ala Val Ala Asp Ala Gly Ser Val Lys
        35                  40                  45 gga att gcg aag ggg ata aag ggg att gtt gat gct gct ggg aag gct   192
Gly Ile Ala Lys Gly Ile Lys Gly Ile Val Asp Ala Ala Gly Lys Ala
50                  55                  60 ttt ggt aag gag ggt gat gcg ctg aag gat gtt gca aaa gtt gct gat   240
Phe Gly Lys Glu Gly Asp Ala Leu Lys Asp Val Ala Lys Val Ala Asp
65                  70                  75                  80 gag aat ggg gat aac aag gat gcg ggg aag ttg ttt gct ggt gag aat   288
Glu Asn Gly Asp Asn Lys Asp Ala Gly Lys Leu Phe Ala Gly Glu Asn
                85                  90                  95
```

```
ggt aat gct ggt ggt gct gct gat gct gac att gcg aag gcg gct gct      336
Gly Asn Ala Gly Gly Ala Ala Asp Ala Asp Ile Ala Lys Ala Ala Ala
        100                 105                 110 gct gtt act gcg gtt agt ggg gag cag ata ctg aaa gct att gtt gag      384
Ala Val Thr Ala Val Ser Gly Glu Gln Ile Leu Lys Ala Ile Val Glu
    115                 120                 125 gct gct ggt gct ggt gat gca gct aat cag gcg ggt aag aag gct gat      432
Ala Ala Gly Ala Gly Asp Ala Ala Asn Gln Ala Gly Lys Lys Ala Asp
130                 135                 140 gag gct aag aat ccg att gcg gct gcg att ggg act gat gat gct ggg      480
Glu Ala Lys Asn Pro Ile Ala Ala Ala Ile Gly Thr Asp Asp Ala Gly
145                 150                 155                 160 gcg gcg ttt ggt cag gat gat atg aag aag aga aat gat aat att gct      528
Ala Ala Phe Gly Gln Asp Asp Met Lys Lys Arg Asn Asp Asn Ile Ala
            165                 170                 175 gcg gct att gtt ttg agg ggg gtg gct aag ggt gga aag ttt gct gtt      576
Ala Ala Ile Val Leu Arg Gly Val Ala Lys Gly Gly Lys Phe Ala Val
        180                 185                 190 gct aat gct gct aat gat agt aag gcg agt gtg aag agt gct gtg          621
Ala Asn Ala Ala Asn Asp Ser Lys Ala Ser Val Lys Ser Ala Val
    195                 200                 205

<210> SEQ ID NO 77
<211> LENGTH: 207
<212> TYPE: PRT
<213> ORGANISM: Borrelia afzelii

<400> SEQUENCE: 77

Glu Ser Ala Val Asp Glu Val Ser Lys Trp Leu Glu Glu Met Ile Thr
1               5                   10                  15

Ala Ala Ser Glu Ala Ala Lys Val G

```
<212> TYPE: DNA
<213> ORGANISM: Borrelia afzelii
<220> FEATURE:
<221> NAME/KEY: CDS
<222> LOCATION: (1

Ile Val Leu Arg Gly Val Ala Lys Asp Gly Lys Phe Ala Ala Ala
    130                 135                 140

Asn Asp Ser Lys Ala Ser Val Lys Ser
145                 150

```
<210> SEQ ID NO 80
<211> LENGTH: 612
<212> TYPE: DNA
<213> ORGANISM: Borrelia afzelii
<220> FEATURE:
<221> NAME/KEY: CDS
<222> LOCATION: (1)..(612)

<400> SEQUENCE: 80
```

| | | | | | | | | | | | | | | | | |
|---|---|---|---|---|---|---|---|---|---|---|---|---|---|---|---|---|
| gct | gtg | gag | agt | gct | gtt | gat | gag | gtt | agc | aag | tgg | tta | gaa | gag | atg | 48 |
| Ala | Val | Glu | Ser | Ala | Val | Asp | Glu | Val | Ser | Lys | Trp | Leu | Glu | Glu | Met | |
| 1 | | | | 5 | | | | | 10 | | | | | 15 | | |
| ata | aca | gct | gct | gat | gct | gct | gct | gct | aaa | gtt | ggc | gat | gct | ggt | ggt | 96 |
| Ile | Thr | Ala | Ala | Asp | Ala | Ala | Ala | Ala | Lys | Val | Gly | Asp | Ala | Gly | Gly | |
| | | | 20 | | | | | 25 | | | | | 30 | | | |
| ggt | gct | gat | aag | att | ggg | gat | gtt | ggt | gct | gct | aat | aag | ggt | gcg | aag | 144 |
| Gly | Ala | Asp | Lys | Ile | Gly | Asp | Val | Gly | Ala | Ala | Asn | Lys | Gly | Ala | Lys | |
| | | 35 | | | | | 40 | | | | | 45 | | | | |
| gct | gat | gcg | agc | agt | gtt | aag | gag | att | gcg | aag | ggg | ata | aag | ggg | att | 192 |
| Ala | Asp | Ala | Ser | Ser | Val | Lys | Glu | Ile | Ala | Lys | Gly | Ile | Lys | Gly | Ile | |
| | 50 | | | | | 55 | | | | | 60 | | | | | |
| gtt | gat | gct | gct | ggg | aag | gct | ttt | ggt | ggt | gat | gcg | ctg | aag | gat | gtt | 240 |
| Val | Asp | Ala | Ala | Gly | Lys | Ala | Phe | Gly | Gly | Asp | Ala | Leu | Lys | Asp | Val | |
| 65 | | | | | 70 | | | | | 75 | | | | | 80 | |
| aaa | gct | gct | ggt | gat | gat | aac | aag | gag | gca | ggg | aag | ttg | ttt | gct | ggt | 288 |
| Lys | Ala | Ala | Gly | Asp | Asp | Asn | Lys | Glu | Ala | Gly | Lys | Leu | Phe | Ala | Gly | |
| | | | | 85 | | | | | 90 | | | | | 95 | | |
| gct | aat | ggt | aat | gct | ggt | gct | aat | gct | gct | gct | gct | gat | gac | att | gcg | 336 |
| Ala | Asn | Gly | Asn | Ala | Gly | Ala | Asn | Ala | Ala | Ala | Ala | Asp | Asp | Ile | Ala | |
| | | | 100 | | | | | 105 | | | | | 110 | | | |
| aag | gcg | gct | ggt | gct | gtt | agt | gcg | gtt | agt | ggg | gag | cag | ata | ctg | aaa | 384 |
| Lys | Ala | Ala | Gly | Ala | Val | Ser | Ala | Val | Ser | Gly | Glu | Gln | Ile | Leu | Lys | |
| | | 115 | | | | | 120 | | | | | 125 | | | | |
| gct | att | gtt | gag | gcg | gct | ggt | gct | gcg | gat | cag | gcg | ggt | gta | aag | gct | 432 |
| Ala | Ile | Val | Glu | Ala | Ala | Gly | Ala | Ala | Asp | Gln | Ala | Gly | Val | Lys | Ala | |
| | 130 | | | | | 135 | | | | | 140 | | | | | |
| gag | gag | gct | aag | aat | ccg | att | gca | gct | gcg | att | ggg | act | gat | gat | gct | 480 |
| Glu | Glu | Ala | Lys | Asn | Pro | Ile | Ala | Ala | Ala | Ile | Gly | Thr | Asp | Asp | Ala | |
| 145 | | | | | 150 | | | | | 155 | | | | | 160 | |
| ggt | gcg | gcg | gag | ttt | ggt | gag | aat | gat | atg | aag | aag | aat | gat | aat | att | 528 |
| Gly | Ala | Ala | Glu | Phe | Gly | Glu | Asn | Asp | Met | Lys | Lys | Asn | Asp | Asn | Ile | |
| | | | | 165 | | | | | 170 | | | | | 175 | | |
| gct | gcg | gct | att | gtt | ttg | agg | ggg | gtg | gct | aag | agt | gga | aag | ttt | gct | 576 |
| Ala | Ala | Ala | Ile | Val | Leu | Arg | Gly | Val | Ala | Lys | Ser | Gly | Lys | Phe | Ala | |
| | | | 180 | | | | | 185 | | | | | 190 | | | |
| gct | aat | gct | aat | gat | gct | ggt | aag | aag | gag | agt | gtg | | | | | 612 |
| Ala | Asn | Ala | Asn | Asp | Ala | Gly | Lys | Lys | Glu | Ser | Val | | | | | |
| | | | 195 | | | | | 200 | | | | | | | | |

```
<210> SEQ ID NO 81
<211> LENGTH: 204
<212> TYPE: PRT
<213> ORGANISM: Borrelia afzelii

<400> SEQUENCE: 81
```

Ala Val Glu Ser Ala Val Asp Glu Val Ser Lys Trp Leu Glu Glu Met

```
         1               5                  10                 15
       Ile Thr Ala Ala Asp Ala Ala Ala Lys Val Gly Asp Ala Gly Gly
                     20                 25                 30
       Gly Ala Asp Lys Ile Gly Asp Val Gly Ala Asn Lys Gly Ala Lys
                     35                 40                 45
       Ala Asp Ala Ser Ser Val Lys Glu Ile Ala Lys Gly Ile Lys Gly Ile
          50                 55                 60
       Val Asp Ala Ala Gly Lys Ala Phe Gly Gly Asp Ala Leu Lys Asp Val
        65                 70                 75                 80
       Lys Ala Ala Gly Asp Asp Asn Lys Glu Ala Gly Lys Leu Phe Ala Gly
                     85                 90                 95
       Ala Asn Gly Asn Ala Gly Ala Asn Ala Ala Ala Asp Asp Ile Ala
                     100                105                110
       Lys Ala Ala Gly Ala Val Ser Ala Val Ser Gly Glu Gln Ile Leu Lys
                     115                120                125
       Ala Ile Val Glu Ala Ala Gly Ala Ala Asp Gln Ala Gly Val Lys Ala
                     130                135                140
       Glu Glu Ala Lys Asn Pro Ile Ala Ala Ile Gly Thr Asp Asp Ala
        145                150                155                160
       Gly Ala Ala Glu Phe Gly Glu Asn Asp Met Lys Lys Asn Asp Asn Ile
                     165                170                175
       Ala Ala Ala Ile Val Leu Arg Gly Val Ala Lys Ser Gly Lys Phe Ala
                     180                185                190
       Ala Asn Ala Asn Asp Ala Gly Lys Lys Glu Ser Val
                     195                200

<210> SEQ ID NO 82
<211> LENGTH: 603
<212> TYPE: DNA
<213> ORGANISM: Borrelia afzelii
<220> FEATURE:
<221> NAME/KEY: CDS
<222> LOCATION: (1)..(603)

<400> SEQUENCE: 82 aag agt gct gtg gat gag gct agc aag tgg tta gaa gag atg ata aca    48
Lys Ser Ala Val Asp Glu Ala Ser Lys Trp Leu Glu Glu Met Ile Thr
 1               5                  10                 15 gct gct ggt gag gct gct aca aag ggt ggt act ggt gaa gct agc gaa    96
Ala Ala Gly Glu Ala Ala Thr Lys Gly Gly Thr Gly Glu Ala Ser Glu
                 20                 25                 30 aag att ggg gat gtt ggt gat aat aat cat ggt gct gta gct gat gcg   144
Lys Ile Gly Asp Val Gly Asp Asn Asn His Gly Ala Val Ala Asp Ala
             35                 40                 45 gac agt gtt aag ggg att gcg aag ggg ata aag ggg att gtt gat gct   192
Asp Ser Val Lys Gly Ile Ala Lys Gly Ile Lys Gly Ile Val Asp Ala
         50                 55                 60 gct ggg aag gct ttt ggt aag gat ggt gcg ctg aag gat gtt gca gct   240
Ala Gly Lys Ala Phe Gly Lys Asp Gly Ala Leu Lys Asp Val Ala Ala
 65                 70                 75                 80 gct gct ggt gat gag gct aac aag gat gcg ggg aag ttg ttt gct ggt   288
Ala Ala Gly Asp Glu Ala Asn Lys Asp Ala Gly Lys Leu Phe Ala Gly
                 85                 90                 95 cag gat ggt ggt ggt gct gat ggt gac att gcg aag gcg gct gct gct   336
Gln Asp Gly Gly Gly Ala Asp Gly Asp Ile Ala Lys Ala Ala Ala Ala
             100                105                110 gtt act gcg gtt agt ggg gag cag ata ctg aaa gct att gtt gag gct   384
Val Thr Ala Val Ser Gly Glu Gln Ile Leu Lys Ala Ile Val Glu Ala
```

```
                115                 120                 125
gct ggt gat aag gct aat cag gtg ggt gta aag gct gct ggt gcg gct       432
Ala Gly Asp Lys Ala Asn Gln Val Gly Val Lys Ala Ala Gly Ala Ala
        130                 135                 140 acg aat ccg att gca gct gcg att ggg act gat gat gat aat gcg gcg       480
Thr Asn Pro Ile Ala Ala Ala Ile Gly Thr Asp Asp Asp Asn Ala Ala
145                 150                 155                 160 gcg ttt gat aag gat gag atg aag aag agt aat gat aag att gct gcg       528
Ala Phe Asp Lys Asp Glu Met Lys Lys Ser Asn Asp Lys Ile Ala Ala
                165                 170                 175 gct att gtt ttg agg ggg gtg gct aag gat gga aag ttt gct gct aat       576
Ala Ile Val Leu Arg Gly Val Ala Lys Asp Gly Lys Phe Ala Ala Asn
        180                 185                 190 gct aat gat aat agt aag gcg agt gtg                                   603
Ala Asn Asp Asn Ser Lys Ala Ser Val
        195                 200
```

<210> SEQ ID NO 83
<211> LENGTH: 201
<212> TYPE: PRT
<213> ORGANISM: Borrelia afzelii

<400> SEQUENCE: 83

```
Lys Ser Ala Val Asp Glu Ala Ser Lys Trp Leu Glu Glu Met Ile Thr
1               5                   10                  15

Ala Ala Gly Glu Ala Ala Thr Lys Gly Gly Thr Gly Glu Ala Ser Glu
            20                  25                  30

Lys Ile Gly Asp Val Gly Asp Asn Asn His Gly Ala Val Ala Asp Ala
        35                  40                  45

Asp Ser Val Lys Gly Ile Ala Lys Gly Ile Lys Gly Ile Val Asp Ala
    50                  55                  60

Ala Gly Lys Ala Phe Gly Lys Asp Gly Ala Leu Lys Asp Val Ala Ala
65                  70                  75                  80

Ala Ala Gly Asp Glu Ala Asn Lys Asp Ala Gly Lys Leu Phe Ala Gly
                85                  90                  95

Gln Asp Gly Gly Gly Ala Asp Gly Asp Ile Ala Lys Ala Ala Ala Ala
            100                 105                 110

Val Thr Ala Val Ser Gly Glu Gln Ile Leu Lys Ala Ile Val Glu Ala
        115                 120                 125

Ala Gly Asp Lys Ala Asn Gln Val Gly Val Lys Ala Ala Gly Ala Ala
    130                 135                 140

Thr Asn Pro Ile Ala Ala Ala Ile Gly Thr Asp Asp Asp Asn Ala Ala
145                 150                 155                 160

Ala Phe Asp Lys Asp Glu Met Lys Lys Ser Asn Asp Lys Ile Ala Ala
                165                 170                 175

Ala Ile Val Leu Arg Gly Val Ala Lys Asp Gly Lys Phe Ala Ala Asn
            180                 185                 190

Ala Asn Asp Asn Ser Lys Ala Ser Val
        195                 200
```

<210> SEQ ID NO 84
<211> LENGTH: 249
<212> TYPE: DNA
<213> ORGANISM: Borrelia afzelii
<220> FEATURE:
<221> NAME/KEY: CDS
<222> LOCATION: (1)..(249)

<400> SEQUENCE: 84

```
aag agt gct gtg gat gag gtt agc aag tgg tta gaa gag atg ata aca    48
Lys Ser Ala Val Asp Glu Val Ser Lys Trp Leu Glu Glu Met Ile Thr
1               5                   10                  15 gct gct agt gat gct gct aca aag ggt ggt act ggt gaa gct agc gaa    96
Ala Ala Ser Asp Ala Ala Thr Lys Gly Gly Thr Gly Glu Ala Ser Glu
            20                  25                  30 aag att ggg gat tct gat gct aat aag ggt ggt gct ggg gcg gcg       144
Lys Ile Gly Asp Ser Asp Ala Asn Lys Gly Gly Ala Gly Ala Ala
        35                  40                  45 ttt ggt gag aat gat atg aag aag aga aat gat aat att gct gca gct   192
Phe Gly Glu Asn Asp Met Lys Lys Arg Asn Asp Asn Ile Ala Ala Ala
50                  55                  60 att gtt ttg agg ggg gtg gct aag gat gga aag ttt gct gtt aag gag   240
Ile Val Leu Arg Gly Val Ala Lys Asp Gly Lys Phe Ala Val Lys Glu
65              70                  75                  80 gat tat tga                                                       249
Asp Tyr

<210> SEQ ID NO 85
<211> LENGTH: 82
<212> TYPE: PRT
<213> ORGANISM: Borrelia afzelii

<400> SEQUENCE: 85

Lys Ser Ala Val Asp Glu Val Ser Lys Trp Leu Glu Glu Met Ile Thr
1               5                   10                  15

Ala Ala Ser Asp Ala Ala Thr Lys Gly Gly Thr Gly Gl

```
aaa cac ttg ggg gtt aat tgt gga acc gaa att tac tat aaa ctt aaa      288
Lys His Leu Gly Val Asn Cys Gly Thr Glu Ile Tyr Tyr Lys Leu Lys
                 85                  90                  95 tat caa aaa caa aaa tgc tat cat aaa ata aac caa tat ttt aaa aag      336
Tyr Gln Lys Gln Lys Cys Tyr His Lys Ile Asn Gln Tyr Phe Lys Lys
            100                 105                 110 aaa aaa gaa att aaa ttt aac tta aga gta agt gca ttt ttt aat aaa      384
Lys Lys Glu Ile Lys Phe Asn Leu Arg Val Ser Ala Phe Phe Asn Lys
        115                 120                 125 aaa cac tca aaa aaa ggg agt gta gaa tta aag gaa tgt aat aat aat      432
Lys His Ser Lys Lys Gly Ser Val Glu Leu Lys Glu Cys Asn Asn Asn
    130                 135                 140 aat aat aat aaa gag aaa gaa aca tcc caa aaa att gaa att tta caa      480
Asn Asn Asn Lys Glu Lys Glu Thr Ser Gln Lys Ile Glu Ile Leu Gln
145                 150                 155                 160 aca aaa gtc tat gcc aaa aaa tgt aaa ttt ttg aca aac tac tat act      528
Thr Lys Val Tyr Ala Lys Lys Cys Lys Phe Leu Thr Asn Tyr Tyr Thr
                165                 170                 175 aaa att tta                                                          537
Lys Ile Leu <210> SEQ ID NO 87
<211> LENGTH: 179
<212> TYPE: PRT
<213> ORGANISM: Borrelia afzelii

<400> SEQUENCE: 87

Met Glu Lys Ile Glu Lys Phe Lys Asn Lys Cys Gln His Lys Leu Gln
1               5                   10                  15

His Lys Leu Ile Val Leu Val Ser Thr Leu Cys Tyr Ile Asn Asn Lys
            20                  25                  30

Asn Lys Lys Tyr Ser Gln Ser Asn Ile Leu Tyr Tyr Phe Asn Glu Asn
        35                  40                  45

Leu Lys Arg Asn Gly Gln Thr Pro Ile Lys Ile Lys Thr Leu Gln Asn
    50                  55                  60

Tyr Leu Tyr Lys Leu Glu Lys Glu Phe Glu Val Thr Thr Asn Tyr Tyr
65                  70                  75                  80

Lys His Leu Gly Val Asn Cys Gly Thr Glu Ile Tyr Tyr Lys Leu Lys
                85                  90                  95

Tyr Gln Lys Gln Lys Cys Tyr His Lys Ile Asn Gln Tyr Phe Lys Lys
            100                 105                 110

Lys Lys Glu Ile Lys Phe Asn Leu Arg Val Ser Ala Phe Phe Asn Lys
        115                 120                 125

Lys His Ser Lys Lys Gly Ser Val Glu Leu Lys Glu Cys Asn Asn Asn
    130                 135                 140

Asn Asn Asn Lys Glu Lys Glu Thr Ser Gln Lys Ile Glu Ile Leu Gln
145                 150                 155                 160

Thr Lys Val Tyr Ala Lys Lys Cys Lys Phe Leu Thr Asn Tyr Tyr Thr
                165                 170                 175

Lys Ile Leu

<210> SEQ ID NO 88
<211> LENGTH: 2775
<212> TYPE: DNA
<213> ORGANISM: Borrelia garinii

<400> SEQUENCE: 88
```

```
cggaaatcaa gccacctaaa acaacttccc aaaagtttct caaaaaatat tatattcagc    60
agtaaattct ataagtcatt aattatttaa tactattcaa cagtaaattc tataagtcat   120
taattattta atactattca gcagtaaatt ctataagtca ttaattattt aatactattc   180
agcagtaaat tctataagtc attaattatt taatactatt cagcagtaaa ttctataagt   240
cattaattat ttaatactat tcagcagtaa attctataag tcattaatta tttaatacta   300
ttcagcagta aattctataa gtcattaatt caattaggta acggattctt agatgtattc   360
acctcttttg gtggattagt tgcagatgca ttggggttta aagctgatcc aaaaaaatct   420
gatgtaaaaa cttattttga atctctagct aaaaaattag aagaaacaaa agatggttta   480
actaagttgt ccaaaggtaa tgacggtgat actggaaagg ctggtgatgc tggtggggct   540
ggtggtggcg ctagtgctgc aggtggcgct ggtgggattg agggcgctat aacagagatt   600
agcaaatggt tagatgatat ggcaaaagct gctgcggaag ctgcaagtgc tgctactggt   660
aatgcagcaa ttggggatgt tgttaatggt aatggtggag cagcaaaagg tggtgatgcg   720
gagagtgtta atgggattgc taaggggata aaggggattg ttgatgctgc tgagaaggct   780
gatgcgaagg aagggaagtt ggatgtggct ggtgatgctg gtggggctgg tggtggcgct   840
ggtgctgcag gtgcgctgg tgggattgag gcgctataa cagagattag caaatggtta   900
gatgatatgg caaaagctgc tgcggttgct gcaagtgctg caagtgctgc tactggtaat   960
gcagcaattg gggatgttgt taatggtaat gatggagcag caaaaggtgg tgatgcggcg  1020
agtgttaatg ggattgctaa ggggataaag gggattgttg atgctgctga aaggctgat  1080 gcgaaggaag ggaagttgga tgtggctggt gatgctggtg agggtaacaa ggatgctggg  1140
aagctgtttg tgaagaagaa tgctggtgat gagggtggtg aagcaaatga tgctgggaag  1200
gctgctgctg cggttgctgc tgttagtggg gagcagatat aaaagcgat tgttgatgct  1260 gctgagggtg atgataagca gggtaagaag gctgcggatg ctacaaatcc gattgaggcg  1320
gctattgggg gtgcggatgc gggtgctaat gctgaggcgt ttaataagat gaagaaggat  1380
gatcagattg ctgctgctat ggttctgagg ggaatggcta aggatgggca gtttgctttg  1440
aaggatgatg ctgctgctca tgaagggact gttaagaatg ctgttgatat ggcaaaggcc  1500
gctgcggaag ctgcaagtgc tgcaagtgct gctactggta gtacaacgat tggagatgtt  1560
gttaagagtg tgaggcaaa agatggtgat gcggcgagtg ttaatgggat tgctaagggg  1620
ataaagggga ttgttgatgc tgctgagaag gctgatgcga aggaagggaa gttggatgtg  1680
gctggtgctg ctggtacgac taacgtgaat gttgggaagt gtttgtgaa gaataatggt  1740 aatgagggtg gtgatgcaag tgatgctggg aaagctgctg ctgcggttgc tgctgttagt  1800
ggggagcaga tattaaaagc gattgttgat gctgctaaag atggtgataa gcagggggtt  1860
actgatgtaa aggatgctac aaatccgatt gaggcggcta ttggggtac aaatgataat  1920 gatgctgcgg cgtttgctac tatgaagaag gatgatcaga ttgctgctgc tatggttctg  1980
aggggaatgg ctaaggatgg gcagtttgct ttgaaggatg atgctgctaa ggatggtgat  2040
aaaacggggg ttgctgcgga tgctgaaaat ccgattgacg cggctattgg gggtgcggat  2100
gctgatgctg cggcgtttaa taaggagggg atgaagaagg atgatcagat tgctgctgct  2160
atggttctga ggggaatggc taaggatggg cagtttgctt tgacgaataa tgctgctgct  2220
catgaaggga ctgttaagaa tgctgttgat atggcaaaag ctgctgcggt tgctgcaagt  2280
gctgctactg gcaatgcagc aattggggat gttgttaaga gtaatggtgg agcagcagca  2340
aaaggtggtg atgcggcgag tgttaatggg attgctaagg ggataaaggg gattgttgat  2400
```

```
gctgctgaga aggctgatgc gaaggaaggg aagttggatg tggctggtgc tgctggtgaa    2460
actaacaagg atgctgggaa gttgtttgtg aagaagaatg tgatgatgg tggtgatgca    2520 ggtgatgctg ggaaggctgc tgctgcggtt gctgctgtta gtggggagca gatattaaaa    2580
gcgattgttg atgctgctaa agatggtgat aagacggggg ttactgatgt aaaggatgct    2640
acaaatccga ttgacgcggc tattgggggg agtgcggatg ctaatgctga ggcgtttgat    2700
aagatgaaga aggatgatca gattgctgct gctatggttc tgaggggaat ggctaaggat    2760
gggcagtttg ctttg                                                    2775

<210> SEQ ID NO 89
<211> LENGTH: 2075
<212> TYPE: DNA
<213> ORGANISM: Borrelia garinii

<400> SEQUENCE: 89
ataaagggga ttgttgatgc tgctgagaag gctgatgcga aggaagggaa gttggatgtg      60
gctggtgatg ctggtgaaac taacaaggat gctgggaagt tgtttgtgaa gaacaatggt     120
aatgagggtg gtgatgcaga tgatgctggg aaggctgctg ctgcggttgc tgctgttagt     180
ggggagcaga tattaaaagc gattgttgat gctgctaagg tggtgataa acgggtaag       240 ataatgtga aggatgctga aaatccgatt gaggcggcta ttgggagtag tcggatgct       300 gatgctgcgg cgtttaataa ggaggggatg aagaaggatg atcagattgc tgctgctatg     360
gttctgaggg gaatggctaa ggatgggcag tttgctttga cgaatgatgc tgctgctcat     420
gaagggactg ttaagaatgc tgttgggagt gcaacaaata agaccgttgt tgctttggct     480
aacttggttc gaaagaccgt gcaagctggg ttgaagaagg ttggggatgt tgttaagaat     540
agtgaggcaa aagatggtga tgcggcgagt gttaatggga ttgctaaggg gataaagggg     600
attgttgatg ctgctgagaa ggctgatgcg aaggaaggga agttggatgt ggctggtgct     660
gctggtgaaa ctaacaagga tgctgggaag ttgtttgtga agaagaataa tgagggtggt     720
gaagcaaatg atgctgggaa ggctgctgct gcggttgctg ctgttagtgg ggagcagata     780
ttaaaagcga ttgttgatgc tgctaaggat ggtgatgata agcagggtaa gaaggctgag     840
gatgctacaa atccgattga cgcggctatt ggggtgcag gtgcgggtgc taatgctgct     900
gcggcgttta ataatatgaa gaaggatgat cagattgctg ctgctatggt tctgagggga     960
atggctaagg atgggcagtt tgctttgacg aataatgctc atactaatca taggggact    1020 gttaagaatg ctgttgatat gacaaaagct gctgcgttg ctgcaagtgc tgcaagtgct    1080
gctactggta atgcagcaat tggggatgtt gttaatggta atgatggagc agcaaaaggt    1140 ggtgatgcg cgagtgttaa tgggattgct aaggggataa aggggattgt tgatgctgct    1200
gagaaggctg atgcgaagga agggaagttg aatgtggctg gtgctgctgg tgctgagggt    1260
aacgaggctg ctgggaagct gtttgtgaag aagaatgctg tgatcatgg tggtgaagca    1320 ggtgatgctg ggaggctgc tgctgcggtt gctgctgtta gtggggagca gatattaaaa    1380
gcgattgttg atgctgctaa ggatggtggt gataagcagg gtaagaaggc tgaggatgct    1440
gaaaatccga ttgacgcggc tattgggagt acgggtgcgg atgataatgc tgctgaggcg    1500
tttgctacta tgaagaagga tgatcagatt gctgctgcta tggttctgag gggaatggct    1560
aaggatgggc agtttgctttt gaaggatgct gctcatgata atcataaggg gactgttaag    1620
aatgctgttg atataataaa ggctactgcg gttgctgcaa gtgctgctac tggtagtaca    1680
```

-continued

```
acgattgggg atgttgttaa aatggtgag gcaaaaggtg gtgaggcgaa gagtgttaat    1740
gggattgcta agggataaa gggattgtt gatgctgctg gaaaggctga tgcgaaggaa    1800
gggaagttga atgtggctgg tgctgctggt gagggtaacg aggctgctgg gaagctgttt    1860
gtgtaaatta ctataggatt agaactagtg tacgatatga gtcctttggt tattttgcag    1920
ctgctaatga atttgaaata agtgaagtta aaattgcgga tgttaatgga acacatttta    1980
ttgctacaaa agagaaagaa atattatatg attcacttga tttaagggct cgtggaaaaa    2040
tatttgaaat aacttcaaag cgaatgttta agctt                              2075
```

<210> SEQ ID NO 90
<211> LENGTH: 552
<212> TYPE: DNA
<213> ORGANISM: Borrelia garinii
<220> FEATURE:
<221> NAME/KEY: CDS
<222> LOCATION: (1)..(552)

<400> SEQUENCE: 90

```
gaa ggg act gtt aag aat gct gtt gat atg gca aaa gct gct gcg gtt      48
Glu Gly Thr Val Lys Asn Ala Val Asp Met Ala Lys Ala Ala Ala Val
1               5                   10                  15 gct gca agt gct gct act ggc aat gca gca att ggg gat gtt gtt aag      96
Ala Ala Ser Ala Ala Thr Gly Asn Ala Ala Ile Gly Asp Val Val Lys
            20                  25                  30 agt aat ggt gga gca gca gca aaa ggt ggt gat gcg gcg agt gtt aat     144
Ser Asn Gly Gly Ala Ala Ala Lys Gly Gly Asp Ala Ala Ser Val Asn
        35                  40                  45 ggg att gct aag ggg ata aag ggg att gtt gat gct gct gag aag gct     192
Gly Ile Ala Lys Gly Ile Lys Gly Ile Val Asp Ala Ala Glu Lys Ala
    50                  55                  60 gat gcg aag gaa ggg aag ttg gat gtg gct ggt gct gct ggt gaa act     240
Asp Ala Lys Glu Gly Lys Leu Asp Val Ala Gly Ala Ala Gly Glu Thr
65                  70                  75                  80 aac aag gat gct ggg aag ttg ttt gtg aag aag aat ggt gat gat ggt     288
Asn Lys Asp Ala Gly Lys Leu Phe Val Lys Lys Asn Gly Asp Asp Gly
                85                  90                  95 ggt gat gca ggt gat gct ggg aag gct gct gct gcg gtt gct gct gtt     336
Gly Asp Ala Gly Asp Ala Gly Lys Ala Ala Ala Ala Val Ala Ala Val
            100                 105                 110 agt ggg gag cag ata tta aaa gcg att gtt gat gct gct aaa gat ggt     384
Ser Gly Glu Gln Ile Leu Lys Ala Ile Val Asp Ala Ala Lys Asp Gly
        115                 120                 125 gat aag acg ggg gtt act gat gta aag gat gct aca aat ccg att gac     432
Asp Lys Thr Gly Val Thr Asp Val Lys Asp Ala Thr Asn Pro Ile Asp
    130                 135                 140 gcg gct att ggg ggg agt gcg gat gct aat gct gag gcg ttt gat aag     480
Ala Ala Ile Gly Gly Ser Ala Asp Ala Asn Ala Glu Ala Phe Asp Lys
145                 150                 155                 160 atg aag aag gat gat cag att gct gct gct atg gtt ctg agg gga atg     528
Met Lys Lys Asp Asp Gln Ile Ala Ala Ala Met Val Leu Arg Gly Met
                165                 170                 175 gct aag gat ggg cag ttt gct ttg                                     552
Ala Lys Asp Gly Gln Phe Ala Leu
            180
```

<210> SEQ ID NO 91
<211> LENGTH: 184
<212> TYPE: PRT
<213> ORGANISM: Borrelia garinii

<400> SEQUENCE: 91

| Glu | Gly | Thr | Val | Lys | Asn | Ala | Val | Asp | Met | Ala | Lys | Ala | Ala | Ala | Val |
|---|---|---|---|---|---|---|---|---|---|---|---|---|---|---|---|
| 1 | | | | 5 | | | | | 10 | | | | | 15 | |

| Ala | Ala | Ser | Ala | Ala | Thr | Gly | Asn | Ala | Ala | Ile | Gly | Asp | Val | Val | Lys |
|---|---|---|---|---|---|---|---|---|---|---|---|---|---|---|---|
| | | | 20 | | | | | 25 | | | | | 30 | | |

| Ser | Asn | Gly | Gly | Ala | Ala | Lys | Gly | Gly | Asp | Ala | Ala | Ser | Val | Asn |
|---|---|---|---|---|---|---|---|---|---|---|---|---|---|---|
| | | 35 | | | | | 40 | | | | | 45 | | |

| Gly | Ile | Ala | Lys | Gly | Ile | Lys | Gly | Ile | Val | Asp | Ala | Ala | Glu | Lys | Ala |
|---|---|---|---|---|---|---|---|---|---|---|---|---|---|---|---|
| | 50 | | | | | 55 | | | | | 60 | | | | |

| Asp | Ala | Lys | Glu | Gly | Lys | Leu | Asp | Val | Ala | Gly | Ala | Ala | Gly | Glu | Thr |
|---|---|---|---|---|---|---|---|---|---|---|---|---|---|---|---|
| 65 | | | | | 70 | | | | | 75 | | | | | 80 |

| Asn | Lys | Asp | Ala | Gly | Lys | Leu | Phe | Val | Lys | Lys | Asn | Gly | Asp | Asp | Gly |
|---|---|---|---|---|---|---|---|---|---|---|---|---|---|---|---|
| | | | | 85 | | | | | 90 | | | | | 95 | |

| Gly | Asp | Ala | Gly | Asp | Ala | Gly | Lys | Ala | Ala | Ala | Val | Ala | Ala | Val |
|---|---|---|---|---|---|---|---|---|---|---|---|---|---|---|
| | | | 100 | | | | | 105 | | | | | 110 | |

| Ser | Gly | Glu | Gln | Ile | Leu | Lys | Ala | Ile | Val | Asp | Ala | Ala | Lys | Asp | Gly |
|---|---|---|---|---|---|---|---|---|---|---|---|---|---|---|---|
| | | | 115 | | | | | 120 | | | | | 125 | | |

| Asp | Lys | Thr | Gly | Val | Thr | Asp | Val | Lys | Asp | Ala | Thr | Asn | Pro | Ile | Asp |
|---|---|---|---|---|---|---|---|---|---|---|---|---|---|---|---|
| | 130 | | | | | 135 | | | | | 140 | | | | |

| Ala | Ala | Ile | Gly | Gly | Ser | Ala | Asp | Ala | Asn | Ala | Glu | Ala | Phe | Asp | Lys |
|---|---|---|---|---|---|---|---|---|---|---|---|---|---|---|---|
| 145 | | | | | 150 | | | | | 155 | | | | | 160 |

| Met | Lys | Lys | Asp | Asp | Gln | Ile | Ala | Ala | Met | Val | Leu | Arg | Gly | Met |
|---|---|---|---|---|---|---|---|---|---|---|---|---|---|---|
| | | | | 165 | | | | | 170 | | | | | 175 |

| Ala | Lys | Asp | Gly | Gln | Phe | Ala | Leu |
|---|---|---|---|---|---|---|---|
| | | | 180 | | | | |

<210> SEQ ID NO 92
<211> LENGTH: 420
<212> TYPE: DNA
<213> ORGANISM: Borrelia garinii
<220> FEATURE:
<221> NAME/KEY: CDS
<222> LOCATION: (1)..(420)

<400> SEQUENCE: 92

| ata | aag | ggg | att | gtt | gat | gct | gct | gag | aag | gct | gat | gcg | aag | gaa | ggg | 48 |
|---|---|---|---|---|---|---|---|---|---|---|---|---|---|---|---|---|
| Ile | Lys | Gly | Ile | Val | Asp | Ala | Ala | Glu | Lys | Ala | Asp | Ala | Lys | Glu | Gly | |
| 1 | | | | 5 | | | | | 10 | | | | | 15 | | |

| aag | ttg | gat | gtg | gct | ggt | gat | gct | ggt | gaa | act | aac | aag | gat | gct | ggg | 96 |
|---|---|---|---|---|---|---|---|---|---|---|---|---|---|---|---|---|
| Lys | Leu | Asp | Val | Ala | Gly | Asp | Ala | Gly | Glu | Thr | Asn | Lys | Asp | Ala | Gly | |
| | | | 20 | | | | | 25 | | | | | 30 | | | |

| aag | ttg | ttt | gtg | aag | aac | aat | ggt | aat | gag | ggt | ggt | gat | gca | gat | gat | 144 |
|---|---|---|---|---|---|---|---|---|---|---|---|---|---|---|---|---|
| Lys | Leu | Phe | Val | Lys | Asn | Asn | Gly | Asn | Glu | Gly | Gly | Asp | Ala | Asp | Asp | |
| | | 35 | | | | | 40 | | | | | 45 | | | | |

| gct | ggg | aag | gct | gct | gct | gcg | gtt | gct | gct | gtt | agt | ggg | gag | cag | ata | 192 |
|---|---|---|---|---|---|---|---|---|---|---|---|---|---|---|---|---|
| Ala | Gly | Lys | Ala | Ala | Ala | Ala | Val | Ala | Ala | Val | Ser | Gly | Glu | Gln | Ile | |
| | 50 | | | | | 55 | | | | | 60 | | | | | |

| tta | aaa | gcg | att | gtt | gat | gct | gct | aag | ggt | ggt | gat | aag | acg | ggt | aag | 240 |
|---|---|---|---|---|---|---|---|---|---|---|---|---|---|---|---|---|
| Leu | Lys | Ala | Ile | Val | Asp | Ala | Ala | Lys | Gly | Gly | Asp | Lys | Thr | Gly | Lys | |
| 65 | | | | | 70 | | | | | 75 | | | | | 80 | |

| aat | aat | gtg | aag | gat | gct | gaa | aat | ccg | att | gag | gcg | gct | att | ggg | agt | 288 |
|---|---|---|---|---|---|---|---|---|---|---|---|---|---|---|---|---|
| Asn | Asn | Val | Lys | Asp | Ala | Glu | Asn | Pro | Ile | Glu | Ala | Ala | Ile | Gly | Ser | |
| | | | | 85 | | | | | 90 | | | | | 95 | | |

| agt | gcg | gat | gct | gat | gct | gcg | gcg | ttt | aat | aag | gag | ggg | atg | aag | aag | 336 |
|---|---|---|---|---|---|---|---|---|---|---|---|---|---|---|---|---|
| Ser | Ala | Asp | Ala | Asp | Ala | Ala | Ala | Phe | Asn | Lys | Glu | Gly | Met | Lys | Lys | |
| | | | 100 | | | | | 105 | | | | | 110 | | | |

| gat | gat | cag | att | gct | gct | gct | atg | gtt | ctg | agg | gga | atg | gct | aag | gat | 384 |
|---|---|---|---|---|---|---|---|---|---|---|---|---|---|---|---|---|
| Asp | Asp | Gln | Ile | Ala | Ala | Ala | Met | Val | Leu | Arg | Gly | Met | Ala | Lys | Asp | |

```
        115                 120                 125
ggg cag ttt gct ttg acg aat gat gct gct gct cat                        420
Gly Gln Phe Ala Leu Thr Asn Asp Ala Ala Ala His
    130                 135                 140

<210> SEQ ID NO 93
<211> LENGTH: 140
<212> TYPE: PRT
<213> ORGANISM: Borrelia garinii

<400> SEQUENCE: 93

Ile Lys Gly Ile Val Asp Ala Ala Glu Lys Ala Asp Ala Lys Glu Gly
1               5                   10                  15

Lys Leu Asp Val Ala Gly Asp Ala Gly Glu Thr Asn Lys Asp Ala Gly
            20                  25                  30

Lys Leu Phe Val Lys Asn Asn Gly Asn Glu Gly Gly Asp Ala Asp Asp
        35                  40                  45

Ala Gly Lys Ala Ala Ala Ala Val Ala Ala Val Ser Gly Glu Gln Ile
    50                  55                  60

Leu Lys Ala Ile Val Asp Ala Ala Lys Gly Gly Asp Lys Thr Gly Lys
65                  70                  75                  80

Asn Asn Val Lys Asp Ala Glu Asn Pro Ile Glu Ala Ala Ile Gly Ser
                85                  90                  95

Ser Ala Asp Ala Asp Ala Ala Ala Phe Asn Lys Glu Gly Met Lys Lys
            100                 105                 110

Asp Asp Gln Ile Ala Ala Ala Met Val Leu Arg Gly Met Ala Lys Asp
        115                 120                 125

Gly Gln Phe Ala Leu Thr Asn Asp Ala Ala Ala His
    130                 135                 140

<210> SEQ ID NO 94
<211> LENGTH: 942
<212> TYPE: DNA
<213> ORGANISM: Borrelia garinii

<400> SEQUENCE: 94
atgagaggat cgcatcacca tcaccatcac ggatccaagg ggactgttaa gaatgctgtt        60
gatatgacaa aagctgctgc ggttgctgca agtgctgcaa gtgctgctac tggtaatgca       120
gcaattgggg atgttgttaa tggtaatgat ggagcagcaa aaggtggtga tcggcgagt        180 gttaatggga ttgctaaggg gataaagggg attgttgatg ctgctgagaa ggctgatgcg       240
aaggaaggga agttgaatgt ggctggtgct gctggtgctg agggtaacga ggctgctggg       300
aagctgtttg tgaagaagaa tgctggtgat catggtggtg aagcaggtga tgctgggagg       360
gctgctgctg cggttgctgc tgttagtggg gagcagatat taaaagcgat tgttgatgct       420
gctaaggatg gtggtgataa gcagggtaag aaggctgagg atgctgaaaa tccgattgac       480
gcggctattg ggagtacggg tgcggatgat aatgctgctg aggcgtttgc tactatgaag       540
aaggatgatc agattgctgc tgctatggtt ctgaggggaa tggctaagga tgggcagttt       600
gctttgaagg atgctgctca tgataatcat ctgcagccaa gcttaattag ctgagcttgg       660
actcctgttg atagatccag taatgacctc agaactccat ctggatttgt tcagaacgct       720
cggttgccgc cgggcgtttt ttattggtga aatccaagc tagcttggcg agattttcag       780
gagctaagga agctaaaatg gagaaaaaat cactggatat accaccgttg atatatccca       840
atggcatcgt aaagaacatt ttgaggcatt tcagtcagtt gctcaatgta cctataacca       900
```

```
gaccgttcag ctggatatta cggcctttt  aaagaccgta ag                      942
```

<210> SEQ ID NO 95
<211> LENGTH: 217
<212> TYPE: PRT
<213> ORGANISM: Borrelia garinii

<400> SEQUENCE: 95

```
Met Arg Gly Ser His His His His His Gly Ser Lys Gly Thr Val
1               5                   10                  15

Lys Asn Ala Val Asp Met Thr Lys Ala Ala Ala Val Ala Ala Ser Ala
            20                  25                  30

Ala Ser Ala Ala Thr Gly Asn Ala Ala Ile Gly Asp Val Val Asn Gly
            35                  40                  45

Asn Asp Gly Ala Ala Lys Gly Gly Asp Ala Ala Ser Val Asn Gly Ile
50                  55                  60

Ala Lys Gly Ile Lys Gly Ile Val Asp Ala Ala Glu Lys Ala Asp Ala
65              70                  75                  80

Lys Glu Gly Lys Leu Asn Val Ala Gly Ala Gly Ala Glu Gly Asn
            85                  90                  95

Glu Ala Ala Gly Lys Leu Phe Val Lys Lys Asn Ala Gly Asp His Gly
            100                 105                 110

Gly Glu Ala Gly Asp Ala Gly Arg Ala Ala Ala Val Ala Ala Val
        115                 120                 125

Ser Gly Glu Gln Ile Leu Lys Ala Ile Val Asp Ala Ala Lys Asp Gly
130                 135                 140

Gly Asp Lys Gln Gly Lys Lys Ala Glu Asp Ala Glu Asn Pro Ile Asp
145                 150                 155                 160

Ala Ala Ile Gly Ser Thr Gly Ala Asp Asp Asn Ala Ala Glu Ala Phe
                165                 170                 175

Ala Thr Met Lys Lys Asp Asp Gln Ile Ala Ala Ala Met Val Leu Arg
            180                 185                 190

Gly Met Ala Lys Asp Gly Gln Phe Ala Leu Lys Asp Ala Ala His Asp
        195                 200                 205

Asn His Leu Gln Pro Ser Leu Ile Ser
    210                 215
```

<210> SEQ ID NO 96
<211> LENGTH: 663
<212> TYPE: DNA
<213> ORGANISM: Borrelia afzelii

<400> SEQUENCE: 96

```
atgagaggat cgcatcacca tcaccatcac ggatccaaga gtgctgtgga tgaggctagc      60
aagtggttag aagagatgat aacagctgct ggtgaggctg ctacaaaggg tggtactggt     120
gaagctagcg aaaagattgg ggatgttggt gataataatc atggtgctgt agctgatgcg     180
gacagtgtta aggggattgc gaaggggata aaggggattg ttgatgctgc tgggaaggct     240
tttggtaagg atggtgcgct gaaggatgtt gcagctgctg ctggtgatga ggctaacaag     300
gatgcgggga gttgtttgc tggtcaggat ggtggtggtg ctgatggtga cattgcgaag      360
gcggctgctg ctgttactgc ggttagtggg gagcagatac tgaaagctat tgttgaggct     420
gctggtgata aggctaatca ggtgggtgta aaggctgctg gtgcggctac gaatccgatt     480
gcagctgcga ttgggactga tgatgataat gcggcggcgt ttgataagga tgagatgaag     540
aagagtaatg ataagattgc tgcggctatt gttttgaggg gggtggctaa ggatggaaag     600
```

```
tttgctgcta atgctaatga taatagtaag gcgagtgtgc tgcagccaag cttaattagc    660
tga                                                                  663
```

\<210\> SEQ ID NO 97
\<211\> LENGTH: 220
\<212\> TYPE: PRT
\<213\> ORGANISM: Borrelia afzelii

\<400\> SEQUENCE: 97

```
Met Arg Gly Ser His His His His His His Gly Ser Lys Ser Ala Val
1               5                   10                  15

Asp Glu Ala Ser Lys Trp Leu Glu Glu Met Ile Thr Ala Ala Gly Glu
            20                  25                  30

Ala Ala Thr Lys Gly Gly Thr Gly Glu Ala Ser Glu Lys Ile Gly Asp
        35                  40                  45

Val Gly Asp Asn Asn His Gly Ala Val Ala Asp Ala Asp Ser Val Lys
    50                  55                  60

Gly Ile Ala Lys Gly Ile Lys Gly Ile Val Asp Ala Ala Gly Lys Ala
65                  70                  75                  80

Phe Gly Lys Asp Gly Ala Leu Lys Asp Val Ala Ala Ala Gly Asp
                85                  90                  95

Glu Ala Asn Lys Asp Ala Gly Lys Leu Phe Ala Gly Gln Asp Gly Gly
            100                 105                 110

Gly Ala Asp Gly Asp Ile Ala Lys Ala Ala Ala Val Thr Ala Val
        115                 120                 125

Ser Gly Glu Gln Ile Leu Lys Ala Ile Val Glu Ala Ala Gly Asp Lys
    130                 135                 140

Ala Asn Gln Val Gly Val Lys Ala Ala Gly Ala Ala Thr Asn Pro Ile
145                 150                 155                 160

Ala Ala Ala Ile Gly Thr Asp Asp Asn Ala Ala Ala Phe Asp Lys
                165                 170                 175

Asp Glu Met Lys Lys Ser Asn Asp Lys Ile Ala Ala Ala Ile Val Leu
            180                 185                 190

Arg Gly Val Ala Lys Asp Gly Lys Phe Ala Ala Asn Ala Asn Asp Asn
        195                 200                 205

Ser Lys Ala Ser Val Leu Gln Pro Ser Leu Ile Ser
    210                 215                 220
```

\<210\> SEQ ID NO 98
\<211\> LENGTH: 26
\<212\> TYPE: DNA
\<213\> ORGANISM: Artificial Sequence
\<220\> FEATURE:
\<223\> OTHER INFORMATION: Description of Artificial Sequence: Synthetic
      Primer

\<400\> SEQUENCE: 98

```
cggaattcac tcgccttact attatc                                          26
```

\<210\> SEQ ID NO 99
\<211\> LENGTH: 29
\<212\> TYPE: DNA
\<213\> ORGANISM: Artificial Sequence
\<220\> FEATURE:
\<223\> OTHER INFORMATION: Description of Artificial Sequence: Synthetic
      Primer

\<400\> SEQUENCE: 99

```
cgggatccga gagtgctgtt gatgaggtt                                    29

<210> SEQ ID NO 100
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 100
cgggatccaa gagtgctgtg gatgaggcta gcaag                             35

<210> SEQ ID NO 101
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 101
ttctgcagca cactcgcctt actattatca ttagc                             35

<210> SEQ ID NO 102
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 102
cgggatccgc tgttgggagt ygcaac                                       26

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 103
aactgcagat tatcatgagc agcatccttc                                   30

<210> SEQ ID NO 104
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 104
cgggatccaa ggggactgtt aagaatgctg ttg                               33

<210> SEQ ID NO 105
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 105
ttctgcagat gattatcatg agcagcatcc ttca                              34
```

```
<210> SEQ ID NO 106
<211> LENGTH: 17
<212> TYPE: DNA
<213> ORGANISM: Borrelia burgdorferi

<400> SEQUENCE: 106
tgagggggct attaagg                                                    17

<210> SEQ ID NO 107
<211> LENGTH: 12
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 107
ccggaattcc gg                                                         12
```